(12) United States Patent
Proud

(10) Patent No.: US 9,610,030 B2
(45) Date of Patent: Apr. 4, 2017

(54) ROOM MONITORING DEVICE AND SLEEP ANALYSIS METHODS

(71) Applicant: Hello Inc., San Francisco, CA (US)

(72) Inventor: James Proud, San Francisco, CA (US)

(73) Assignee: Hello Inc., San Francisco, CA (US)

( * ) Notice: Subject to any disclaimer, the term of this patent is extended or adjusted under 35 U.S.C. 154(b) by 146 days.

(21) Appl. No.: 14/604,566

(22) Filed: Jan. 23, 2015

(65) Prior Publication Data

US 2016/0213308 A1     Jul. 28, 2016

(51) Int. Cl.
*A61B 5/00*     (2006.01)
*A61B 5/11*     (2006.01)
(Continued)

(52) U.S. Cl.
CPC .......... *A61B 5/1123* (2013.01); *A61B 5/0002* (2013.01); *A61B 5/1118* (2013.01); *A61B 5/4806* (2013.01); *G06F 3/017* (2013.01); *A61B 5/742* (2013.01); *A61B 5/7405* (2013.01); *A61B 2090/309* (2016.02); *A61B 2560/0252* (2013.01); *A61B 2560/0475* (2013.01); *A61B 2562/0204* (2013.01); *A61B 2562/029* (2013.01); *A61B 2562/0219* (2013.01); *A61B 2562/0257* (2013.01); *H04M 2250/12* (2013.01)

(58) Field of Classification Search
CPC ....... A61B 5/11; A61B 5/1112; A61B 5/1113; A61B 5/1115; A61B 5/1123; A61B 5/1118; A61B 5/0002; A61B 5/4806; A61B 5/7405; A61B 5/742; A61B 2250/12; A61B 2562/0257; A61B 2562/0204; A61B 2562/0219; A61B 2560/0252; A61B 2560/0475; A61B 2090/017; A61F 3/017
See application file for complete search history.

(56) References Cited

U.S. PATENT DOCUMENTS 3,127,363 A   3/1964   Nitzsche et al.
3,715,334 A   2/1973   Karstedt
(Continued)

FOREIGN PATENT DOCUMENTS

DE   3839900   5/1990
EP   0183553   6/1986
(Continued)

OTHER PUBLICATIONS

Davida, G.I., et al., "On enabling secure applications through off-line biometric identification", Proceedings of the IEEE Symposium on Security and Privacy (May 1998).
(Continued)

*Primary Examiner* — Max Hindenburg
(74) *Attorney, Agent, or Firm* — Paul Davis

(57) ABSTRACT

A method monitors a person's sleep parameters, sleep activities, sleep state, or awake status sleep. At least one of a person's motion, movement and gesture is detected for determining a person's sleep parameters, sleep activities, sleep state, or awake status. The at least one of a person's motion, movement and gesture is communicated to a user monitoring device that includes at least two elements selected from: a proximity sensor; a temperature sensor/humidity sensor; a particulate sensor; a light sensor; a microphone; a speaker; two RF transmitters (BLE/ANT+WIFI); a memory card; and LED's.

12 Claims, 48 Drawing Sheets

(51) Int. Cl.
  *G06F 3/01*     (2006.01)
  *A61B 90/30*    (2016.01)

(56)          References Cited

U.S. PATENT DOCUMENTS

| | | | |
|---|---|---|---|
| 3,775,452 | A | 11/1973 | Karstedt |
| 3,813,364 | A | 5/1974 | Zuba et al. |
| 3,814,730 | A | 6/1974 | Karstedt |
| 4,394,317 | A | 7/1983 | McAfee et al. |
| 5,057,151 | A | 10/1991 | Schuster et al. |
| 5,187,657 | A | 2/1993 | Forbes |
| 5,348,008 | A | 9/1994 | Bornn et al. |
| 5,564,429 | A | 10/1996 | Bornn et al. |
| 5,576,054 | A | 11/1996 | Brown |
| 6,038,315 | A | 3/2000 | Strait et al. |
| 6,221,012 | B1 | 4/2001 | Maschke et al. |
| 6,323,846 | B1 | 11/2001 | Westerman et al. |
| 6,416,471 | B1 | 7/2002 | Kumar et al. |
| 6,440,067 | B1 | 8/2002 | DeLuca et al. |
| 6,454,708 | B1 | 9/2002 | Ferguson et al. |
| 6,570,557 | B1 | 5/2003 | Westerman et al. |
| 6,661,372 | B1 | 12/2003 | Girerd et al. |
| 6,677,932 | B1 | 1/2004 | Westerman |
| 6,893,396 | B2 | 5/2005 | Schulze et al. |
| 7,113,932 | B2 | 9/2006 | Tayebnejad et al. |
| 7,502,643 | B2 | 3/2009 | Farringdon et al. |
| 7,614,008 | B2 | 11/2009 | Ording |
| 7,633,076 | B2 | 12/2009 | Huppi et al. |
| 7,653,883 | B2 | 1/2010 | Hotelling et al. |
| 7,657,849 | B2 | 2/2010 | Chaudhri et al. |
| 7,663,607 | B2 | 2/2010 | Hotelling et al. |
| 7,844,914 | B2 | 11/2010 | Andre et al. |
| 7,957,762 | B2 | 6/2011 | Herz et al. |
| 7,959,567 | B2 | 6/2011 | Stivoric et al. |
| 8,006,002 | B2 | 8/2011 | Kalayjian et al. |
| 8,033,996 | B2 | 10/2011 | Behar |
| 8,044,363 | B2 | 10/2011 | Ales et al. |
| 8,126,729 | B2 | 2/2012 | Dicks et al. |
| 8,157,731 | B2 | 4/2012 | Teller et al. |
| 8,204,786 | B2 | 6/2012 | LeBoeuf et al. |
| 8,239,784 | B2 | 8/2012 | Hotelling et al. |
| 8,279,180 | B2 | 10/2012 | Hotelling et al. |
| 8,328,718 | B2 | 12/2012 | Tran |
| 8,352,211 | B2 | 1/2013 | Vock et al. |
| 8,369,936 | B2 | 2/2013 | Farringdon et al. |
| 8,378,811 | B2 | 2/2013 | Crump et al. |
| 8,381,135 | B2 | 2/2013 | Hotelling et al. |
| 8,389,627 | B2 | 3/2013 | Rubinsztajn et al. |
| 8,390,463 | B2 | 3/2013 | Munthe-Kaas et al. |
| 8,398,538 | B2 * | 3/2013 | Dothie .............. A61B 5/11 600/26 |
| 8,398,546 | B2 | 3/2013 | Pacione et al. |
| 8,479,122 | B2 | 7/2013 | Hotelling et al. |
| 8,882,684 | B2 * | 11/2014 | Halperin .......... A61B 5/002 600/300 |
| 9,204,806 | B2 * | 12/2015 | Stivoric ........... A61B 5/0008 |
| 9,326,364 | B2 * | 4/2016 | Maeda ............ H05B 37/0281 |
| 9,345,433 | B1 * | 5/2016 | Shinozuka ......... A61B 5/1115 |
| 9,360,351 | B2 * | 6/2016 | Van Thienen ...... G01D 5/353 |
| 2002/0015024 | A1 | 2/2002 | Westerman et al. |
| 2003/0121033 | A1 | 6/2003 | Peev et al. |
| 2004/0172290 | A1 | 9/2004 | Leven |
| 2005/0113650 | A1 | 5/2005 | Pacione et al. |
| 2005/0190059 | A1 | 9/2005 | Wehrenberg |
| 2006/0017692 | A1 | 1/2006 | Wehrenberg et al. |
| 2006/0026536 | A1 | 2/2006 | Hotelling et al. |
| 2006/0030891 | A1 | 2/2006 | Saltzstein et al. |
| 2006/0033724 | A1 | 2/2006 | Chaudhri et al. |
| 2006/0159645 | A1 | 7/2006 | Miller et al. |
| 2006/0197753 | A1 | 9/2006 | Hotelling |
| 2008/0012701 | A1 | 1/2008 | Kass et al. |
| 2009/0023428 | A1 | 1/2009 | Behzad et al. |
| 2009/0182208 | A1 | 7/2009 | Cho et al. |
| 2009/0255122 | A1 | 10/2009 | Azrielant |
| 2010/0153269 | A1 | 6/2010 | McCabe |
| 2012/0146795 | A1 | 6/2012 | Margon et al. |
| 2012/0170521 | A1 | 7/2012 | Vogedes et al. |
| 2012/0194419 | A1 | 8/2012 | Osterhout et al. |
| 2012/0205373 | A1 | 8/2012 | Caldwell |
| 2012/0225719 | A1 | 9/2012 | Nowozin et al. |
| 2012/0226639 | A1 | 9/2012 | Burdick et al. |
| 2012/0229270 | A1 | 9/2012 | Morley et al. |
| 2012/0253489 | A1 | 10/2012 | Dugan |
| 2013/0022659 | A1 | 1/2013 | Roberts |
| 2013/0127980 | A1 | 5/2013 | Haddick et al. |
| 2013/0175732 | A1 | 7/2013 | Lust et al. |
| 2013/0326790 | A1 | 12/2013 | Cauwels et al. |
| 2014/0266939 | A1 | 9/2014 | Baringer et al. |

FOREIGN PATENT DOCUMENTS

| | | |
|---|---|---|
| EP | 0271423 | 6/1988 |
| EP | 0369255 | 5/1990 |
| EP | 371004 | 5/1990 |
| EP | 0477681 | 4/1992 |
| EP | 0567253 | 10/1993 |
| EP | 0640663 | 3/1995 |
| EP | 0654497 | 5/1995 |
| EP | 1094091 | 4/2001 |
| EP | 1113042 | 7/2001 |
| EP | 1133936 | 9/2001 |
| EP | 1172414 | 1/2002 |
| EP | 1217042 | 6/2002 |
| EP | 1371004 | 8/2002 |
| EP | 1367534 | 12/2003 |
| EP | 1555297 | 7/2005 |
| EP | 1595676 | 11/2005 |
| EP | 1785454 | 5/2007 |
| EP | 1792944 | 6/2007 |
| EP | 2063555 | 5/2009 |
| EP | 2428774 | 3/2012 |
| EP | 1883798 | 5/2012 |
| EP | 2052352 | 5/2012 |
| EP | 2582116 | 4/2013 |
| EP | 2614945 | 7/2013 |
| GB | 1278798 | 6/1972 |
| GB | 1381933 | 1/1975 |
| GB | 2460890 | 12/2009 |
| WO | 8704449 | 7/1987 |
| WO | 9500992 | 1/1995 |
| WO | 9956922 | 11/1999 |
| WO | 02063555 | 8/2002 |
| WO | 2006127726 | 11/2006 |
| WO | 2008050951 | 5/2008 |
| WO | 2012170305 | 12/2012 |
| WO | 2013076676 | 5/2013 |
| WO | 2013081447 | 6/2013 |

OTHER PUBLICATIONS

Juels, A., et al., "A Fuzzy Vault Scheme", Proceedings of the 2002 IEEE Symposium on Information Theory (Jun. 2002).

Yang, S., et al., "Secure fuzzy vault fingerprint verification system", Asilomar Conf. on Signals, Systems and Comp., vol. 1, pp. 577-581 (Nov. 2004).

Uludag, U., et al., "Fuzzy fingerprint vault", Proc. Workshop: Biometrics: Challenges arising from theory to practice, pp. 13-16 (Aug. 2004).

* cited by examiner

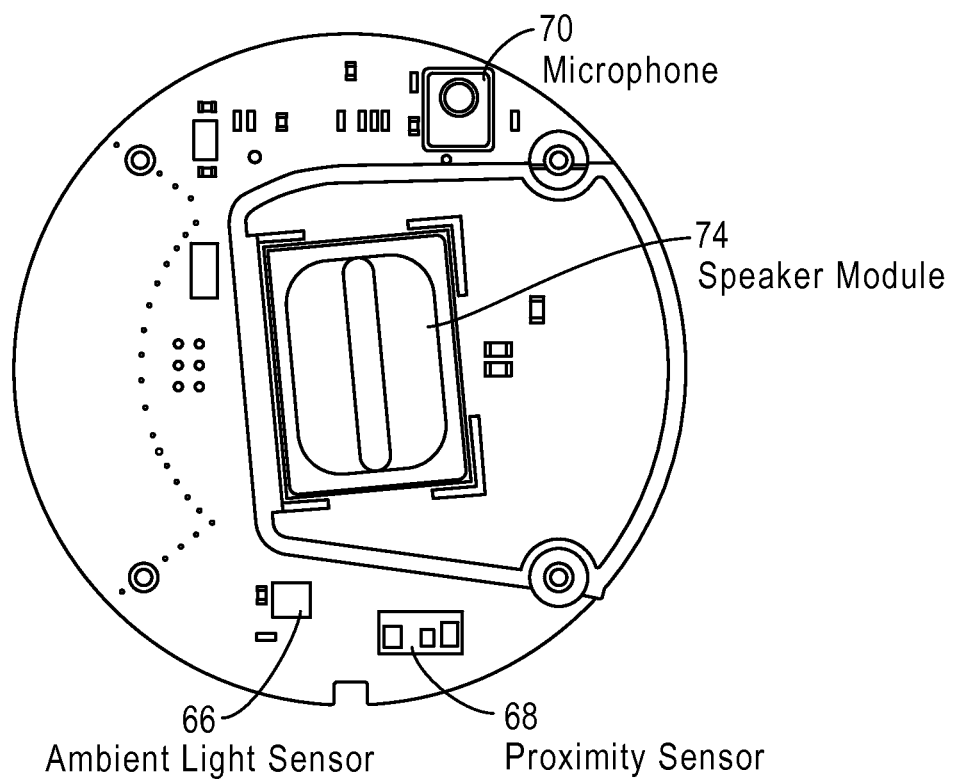
FIG. 1C1
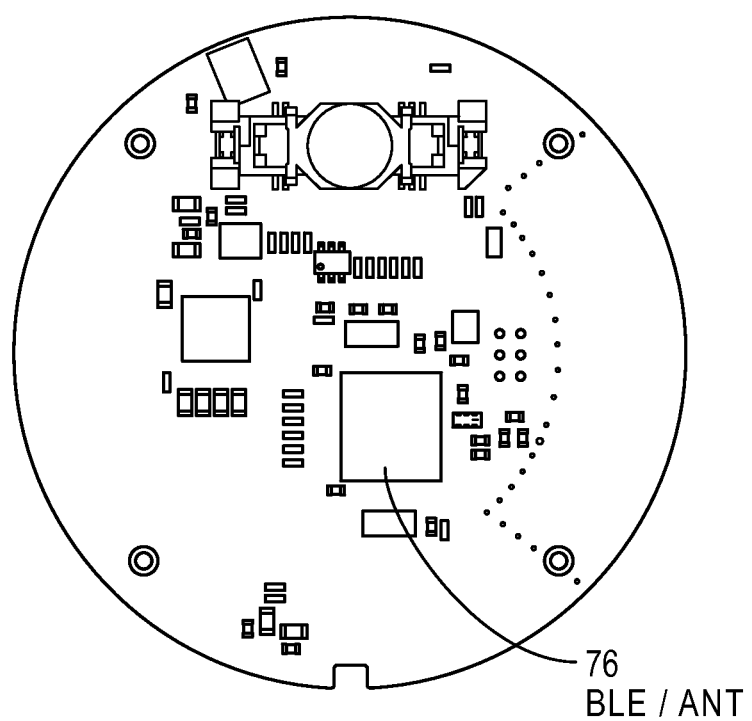
FIG. 1C2

FRONT

BACK

ROOM MONITORING DEVICE AND SLEEP ANALYSIS METHODS

BACKGROUND

Field of the Invention

The present invention is generally to methods using room monitoring devices, and more particularly to methods that provide monitoring of a person's sleep activity and/or sleep parameter, disorder, condition and the like.

Description of the Related Art

Methods are known for sensing body movement or non-movement as well as, for sensing body movement over time, which is commonly used to determine comparative levels of activity of a monitored body.

Tracking of a movement of one or more body parts such as a head, eye, or other parts may be performed by analysis of a series of images captured by an imager and detection of a movement of one or more of such body parts. Such tracking may activate one or more functions of a device or other functions.

Nearly one in seven people in the United States suffer from some type of chronic sleep disorder, and only fifty percent (50%) of people are estimated to get the recommended seven (7) to eight (8) hours of sleep each night. It is further estimated that sleep deprivation and its associated medical and social costs (loss of productivity, industrial accidents, etc) exceed $150 billion dollars per year. Excessive sleepiness can deteriorate the quality of life and is a major cause of morbidity and mortality due to its role in industrial and transportation accidents. Sleepiness further has undesirable effects on motor vehicle driving, employment, higher earning and job promotion opportunities, education, recreation, and personal life.

Excessive daytime sleepiness (EDS) is a symptom describing an increased propensity to fall asleep, often during monotonous or sedentary activities. Though sometimes difficult, EDS vs. fatigue need to be differentiated. Fatigue or lethargy is where a subject senses a lack of energy or physical weakness and may not have an increased propensity to fall asleep at an inappropriate time. The underlying etiology of EDS generally falls into three categories: chronic sleep deprivation, circadian disorders (shift work), and sleep disorders. EDS is currently diagnosed via two general methods. The first is via subjective methods such as the Epworth and Standford Sleepiness Scale, which generally involves questionnaires where the patients answer a series of qualitative questions regarding their sleepiness during the day. With these methods, however, it is found that the patients usually underestimate their level of sleepiness or they deliberately falsify their responses because of their concern regarding punitive action, or as an effort to obtain restricted stimulant medication.

The second is via physiological based evaluations such as all night polysomnography to evaluate the patients sleep architecture (e.g., obtaining respiratory disturbance index to diagnose sleep apnea) followed by an all day test such as the Multiple Sleep Latency Test (MSLT) or its modified version, Maintenance of Wakefulness Test (MWT). The MSLT consists of four (4) to five (5) naps and is considered the most reliable objective measure of sleepiness to date. The MSLT involves monitoring the patient during twenty (20) to forty (40) minute nap periods in two-hour intervals one and one half hour (1.5 hrs) to three hours (3 hrs) after awakenings to examine the sleep latency and the sleep stage that the patient achieves during these naps, i.e., the time it takes for the patient to fall asleep. A sleep disorder such as narcolepsy for example is diagnosed when the patient has a restful night sleep the night before but undergoes rapid eye movement sleep (REM sleep) within five (5) minutes of the MSLT naps. The MWT is a variation of the MSLT. The MWT provides an objective measure of the ability of an individual to stay awake.

While the MSLT and MWT are more objective and therefore don't have the same limitations as mentioned for the subjective tests, the MSLT and MWT have their own limitations. Both the MSLT and MWT require an all-day stay at a specialized sleep clinic and involve monitoring a number of nap opportunities at two hour intervals throughout the day. Further, the MSLT mean sleep latency is only meaningful if it is extremely short in duration (e.g., to diagnose narcolepsy), and only if the overnight polysomnogram does not show any sleep disordered breathing. Another problem with the MSLT mean sleep latency is the so-called "floor effect" where the sleep latency in the pathologically sleepy patients can be almost zero (0) minutes, i.e., the patient falls asleep almost immediately following turning off the light in the MSLT test. This type of result has a tendency to limit the diagnostic resolution of the test. Finally, studies have shown that the MSLT is not particularly suited for gauging the effects of therapeutic intervention.

In recent years there have been a number of efforts to develop systems for detecting alertness and drowsiness by attempting to quantify the brain waves of a subject. Most of these systems have been aimed at the alertness monitoring field for alertness critical applications. One system discloses a device for monitoring and maintaining an alert state of consciousness for a subject wearing the device. With this device an alert mental state is maintained through monitoring of brain wave patterns to detect if a transition from an alert to a non-alert mental state is about to occur, or has occurred. If so, the device provides a stimulus until such time as an alert mental state, as assessed by the brain wave activity, is restored. Another system discloses a method of classifying individual EEG patterns along an alertness-drowsiness classification continuum. The results of the multi-level classification system are applied in real-time to provide feedback to the user via an audio or visual alarm, or are recorded for subsequent off-line analysis.

Most of the methods, systems or devices currently on the market either provide a qualitative means for analyzing for excessive daytime sleepiness or more specifically for sleep disorders, or a semi-quantitative means for classifying a subjects state of alertness.

SUMMARY

An object of the present invention is to provide methods that provide monitoring of a person's sleep activity and/or sleep parameter.

Another object of the present invention is to provide methods that provide sensing of a person's movement/motion/gesture for determining a sleep parameter.

Yet another object of the present invention is to provide methods that provide sensing of a person's movement/motion/gesture uses for determining a person's sleep parameters or activities.

A further object of the present invention is to provide methods that provide sensing of a person's activities relative to one or more sleep parameters.

These and other objects of the present invention are achieved in a method for monitoring a person's sleep parameters, sleep activities, sleep state, or awake status sleep. At least one of a person's motion, movement and gesture is detected for determining a person's sleep parameters, sleep activities, sleep state, or awake status. The at least one of a person's motion, movement and gesture is communicated to a user monitoring device that includes at least two elements selected from: a proximity sensor; a temperature sensor/humidity sensor; a particulate sensor; a light sensor; a microphone; a speaker; two RF transmitters (BLE/ANT+WIFI); a memory card; and LED's.

BRIEF DESCRIPTION OF THE DRAWINGS

FIG. 1(c) illustrates one embodiment of a top board of the FIG. 1(a) user monitoring device with an ambient light sensor, a proximity sensor, a speak module and a microphone.

DETAILED DESCRIPTION

Figure 1A:
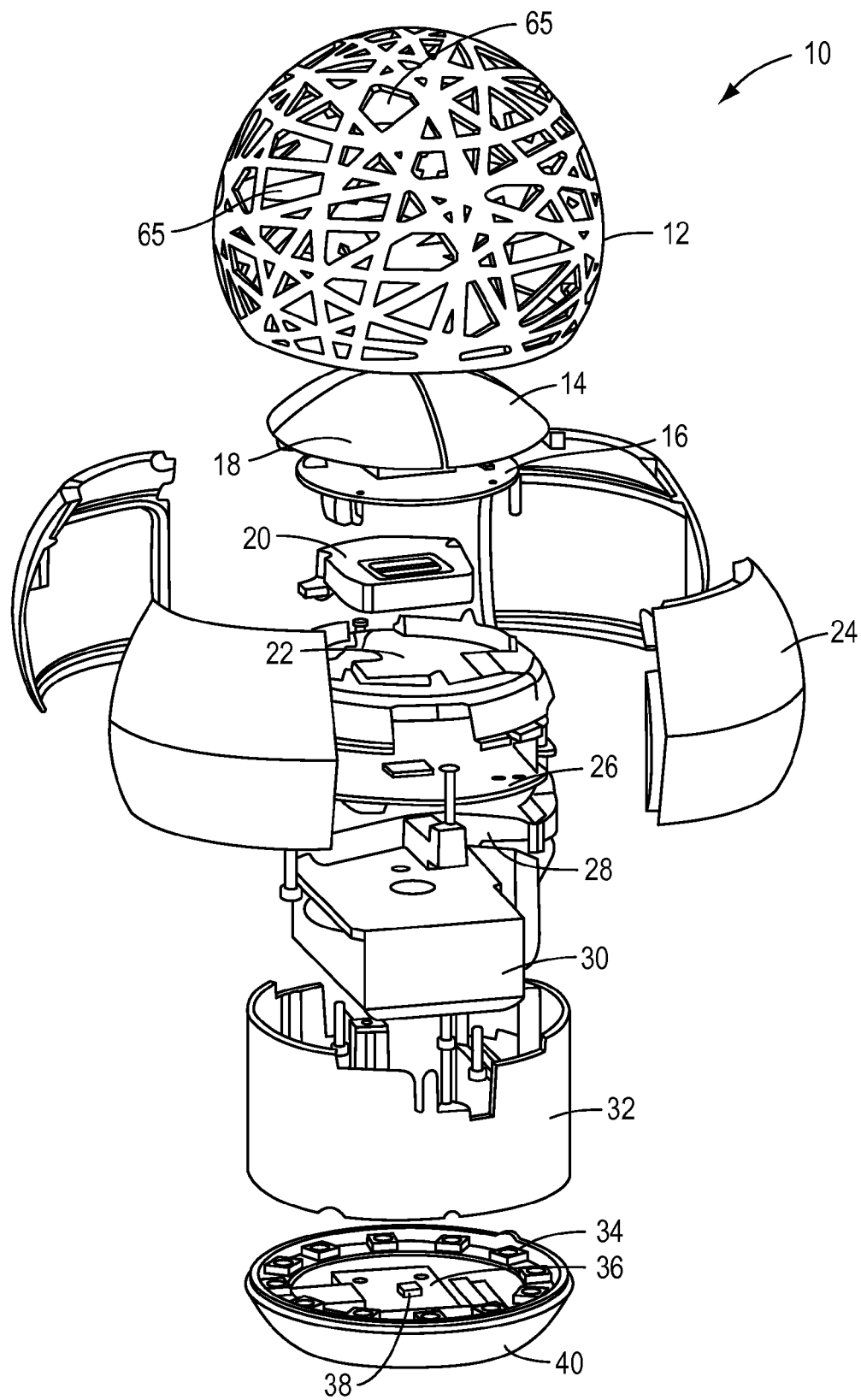
FIG. 1(a) is an exploded view of one embodiment of a user monitoring device of the present invention.

As used herein, the term engine refers to software, firmware, hardware, or other component that can be used to effectuate a purpose. The engine will typically include software instructions that are stored in non-volatile memory (also referred to as secondary memory) and a processor with instructions to execute the software. When the software instructions are executed, at least a subset of the software instructions can be loaded into memory (also referred to as primary memory) by a processor. The processor then executes the software instructions in memory. The processor may be a shared processor, a dedicated processor, or a combination of shared or dedicated processors. A typical program will include calls to hardware components (such as I/O devices), which typically requires the execution of drivers. The drivers may or may not be considered part of the engine, but the distinction is not critical.

As used herein, the term database is used broadly to include any known or convenient means for storing data, whether centralized or distributed, relational or otherwise.

As used herein a mobile device includes, but is not limited to, a cell phone, such as Apple's iPhone®, other portable electronic devices, such as Apple's iPod Touches®, Apple's iPads®, and mobile devices based on Google's Android® operating system, and any other portable electronic device that includes software, firmware, hardware, or a combination thereof that is capable of at least receiving a wireless signal, decoding if needed, and exchanging information with a server. Typical components of mobile device may include but are not limited to persistent memories like flash ROM, random access memory like SRAM, a camera, a battery, LCD driver, a display, a cellular antenna, a speaker, a BLUETOOTH® circuit, and WIFI circuitry, where the persistent memory may contain programs, applications, and/or an operating system for the mobile device. For purposes of this application, a mobile device is also defined to include a fob, and its equivalents.

As used herein, the term "computer" is a general purpose device that can be programmed to carry out a finite set of arithmetic or logical operations. Since a sequence of operations can be readily changed, the computer can solve more than one kind of problem. A computer can include of at least one processing element, typically a central processing unit (CPU) and some form of memory. The processing element carries out arithmetic and logic operations, and a sequencing and control unit that can change the order of operations based on stored information. Peripheral devices allow information to be retrieved from an external source, and the result of operations saved and retrieved. Computer also includes a graphic display medium.

As used herein, the term "internet" is a global system of interconnected computer networks that use the standard Network Systems protocol suite (TCP/IP) to serve billions of users worldwide. It is a network of networks that consists of millions of private, public, academic, business, and government networks, of local to global scope, that are linked by a broad array of electronic, wireless and optical networking technologies. The internet carries an extensive range of information resources and services, such as the inter-linked hypertext documents of the World Wide Web (WWW) and the infrastructure to support email. The communications infrastructure of the internet consists of its hardware components and a system of software layers that control various aspects of the architecture.

As used herein, the term "extranet" is a computer network that allows controlled access from the outside. An extranet can be an extension of an organization's intranet that is extended to users outside the organization in isolation from all other internet users. An extranet can be an intranet mapped onto the public internet or some other transmission system not accessible to the general public, but managed by more than one company's administrator(s). Examples of extranet-style networks include but are not limited to:

LANs or WANs belonging to multiple organizations and interconnected and accessed using remote dial-up LANs or WANs belonging to multiple organizations and interconnected and accessed using dedicated lines Virtual private network (VPN) that is comprised of LANs or WANs belonging to multiple organizations, and that extends usage to remote users using special "tunneling" software that creates a secure, usually encrypted network connection over public lines, sometimes via an ISP.

As used herein, the term "Intranet" is a network that is owned by a single organization that controls its security policies and network management. Examples of intranets include but are not limited to:

A LAN

A Wide-area network (WAN) that is comprised of a LAN that extends usage to remote employees with dial-up access A WAN that is comprised of interconnected LANs using dedicated communication lines A Virtual private network (VPN) that is comprised of a LAN or WAN that extends usage to remote employees or networks using special "tunneling" software that creates a secure, usually encrypted connection over public lines, sometimes via an Internet Service Provider (ISP).

For purposes of the present invention, the Internet, extranets and intranets collectively are referred to as ("Network Systems").

As used herein "Cloud Application" refers to cloud application services or "software as a service" (SaaS) which deliver software over the Network Systems eliminating the need to install and run the application on a device.

As used herein "Cloud Platform" refers to a cloud platform services or "platform as a service" (PaaS) which deliver a computing platform and/or solution stack as a service, and facilitates the deployment of applications without the cost and complexity of obtaining and managing the underlying hardware and software layers.

As used herein "Cloud System" refers to cloud infrastructure services or "infrastructure as a service" (IAAS) which deliver computer infrastructure as a service with raw block storage and networking.

As used herein "Server" refers to server layers that consist of computer hardware and/or software products specifically designed for the delivery of cloud services.

As used herein, the term "user monitoring" includes: (i) cardiac monitoring, which generally refers to continuous electrocardiography with assessment of the user's condition relative to their cardiac rhythm. A small monitor worn by an ambulatory user for this purpose is known as a Holter monitor. Cardiac monitoring can also involve cardiac output monitoring via an invasive Swan-Ganz catheter (ii) Hemodynamic monitoring, which monitors the blood pressure and blood flow within the circulatory system. Blood pressure can be measured either invasively through an inserted blood pressure transducer assembly, or noninvasively with an inflatable blood pressure cuff. (iii) Respiratory monitoring, such as: pulse oximetry which involves measurement of the saturated percentage of oxygen in the blood, referred to as SpO2, and measured by an infrared finger cuff, capnography, which involves CO2 measurements, referred to as EtCO2 or end-tidal carbon dioxide concentration. The respiratory rate monitored as such is called AWRR or airway respiratory rate). (iv) respiratory rate monitoring through a thoracic transducer belt, an ECG channel or via capnography, (v) Neurological monitoring, such as of intracranial pressure. Special user monitors can incorporate the monitoring of brain waves electroencephalography, gas anesthetic concentrations, bispectral index (BIS), and the like, (vi) blood glucose monitoring using glucose sensors. (vii) childbirth monitoring with sensors that monitor various aspects of childbirth. (viii) body temperature monitoring which in one embodiment is through an adhesive pad containing a thermoelectric transducer. (ix) stress monitoring that can utilize sensors to provide warnings when stress levels signs are rising before a human can notice it and provide alerts and suggestions. (x) epilepsy monitoring. (xi) toxicity monitoring, (xii) general lifestyle parameters, (xiii) sleep, including but not limited to: sleep patterns, type of sleep, sleep disorders, movement during sleep, waking up, falling asleep, problems with sleep, habits during, before and after sleep, time of sleep, length sleep in terms of the amount of time for each sleep sleep, body activities during sleep, brain patterns during sleep and the like (xiv) body gesture, movement and motion (xv) body habits, (xvi) and the like.

In various embodiments, the present invention provides systems and methods for monitoring and reporting human physiological information, life activities data of the individual, generate data indicative of one or more contextual parameters of the individual, monitor the degree to which an individual has followed a routine and the like, along with providing feedback to the individual.

In certain embodiments, the suggested routine may include a plurality of categories, including but not limited to, body movement/motion/gesture, habits, health parameters, activity level, mind centering, sleep, daily activities, exercise and the like.

In general, according to the present invention, data relating to any or all of the above is collected and transmitted, either subsequently or in real-time, to a site, the cloud and the like that can be remote from the individual, where it is analyzed, stored, utilized, and the like via Network System. Contextual parameters as used herein means parameters relating any of the above, including the environment, surroundings and location of the individual, air quality, sound quality, ambient temperature, global positioning and the like, as well as anything relative to the categories mentioned above.

In various embodiments, the present invention provides a user monitoring device 10. As illustrated in FIG. 1(a) monitoring device 10 can include an outer shell 12, a protective cover 14, a top circuit board 16, a microphone 18, a speaker module 20, a circuit board support structure 22, a protective quadrant 24, a middle circuit board 26, a particular air duct 28, a particulate sensor 30, a center support structure 32, a light emitter 34, a bottom circuit board 36, a temperature sensor 38, FIG. 1(b) and a base 40.

Figure 1B:
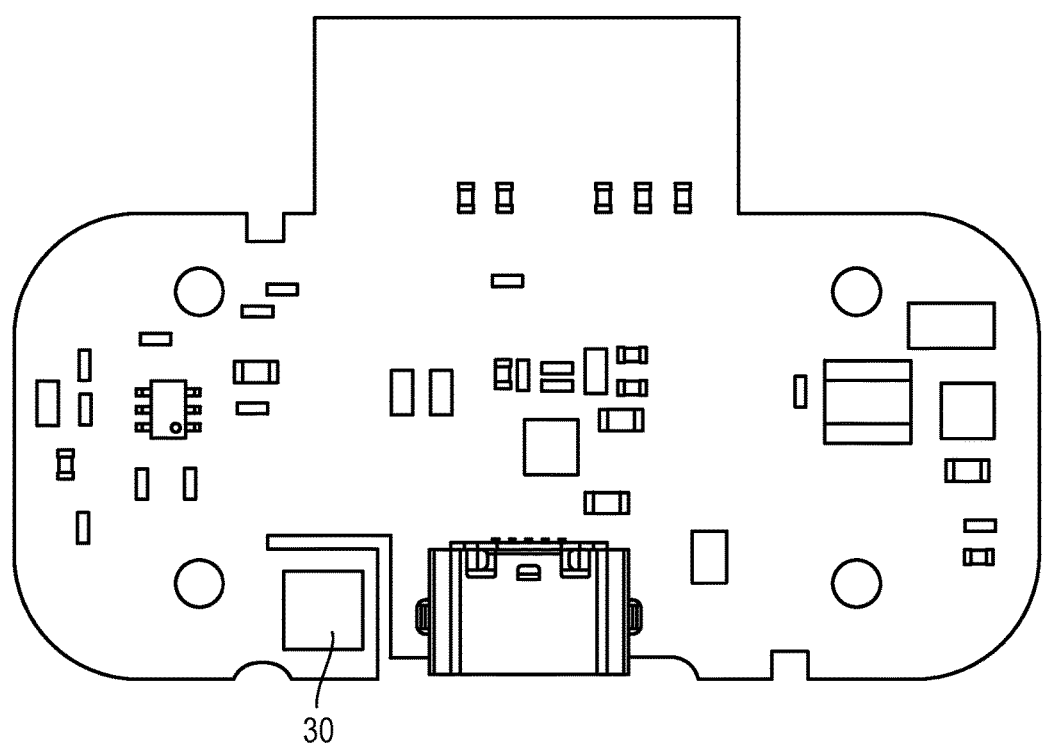
FIG. 1(b) illustrates one embodiment of a bottom board of the FIG. 1(a) user monitoring device with a temperature and humidity sensor.
Figure 1D:
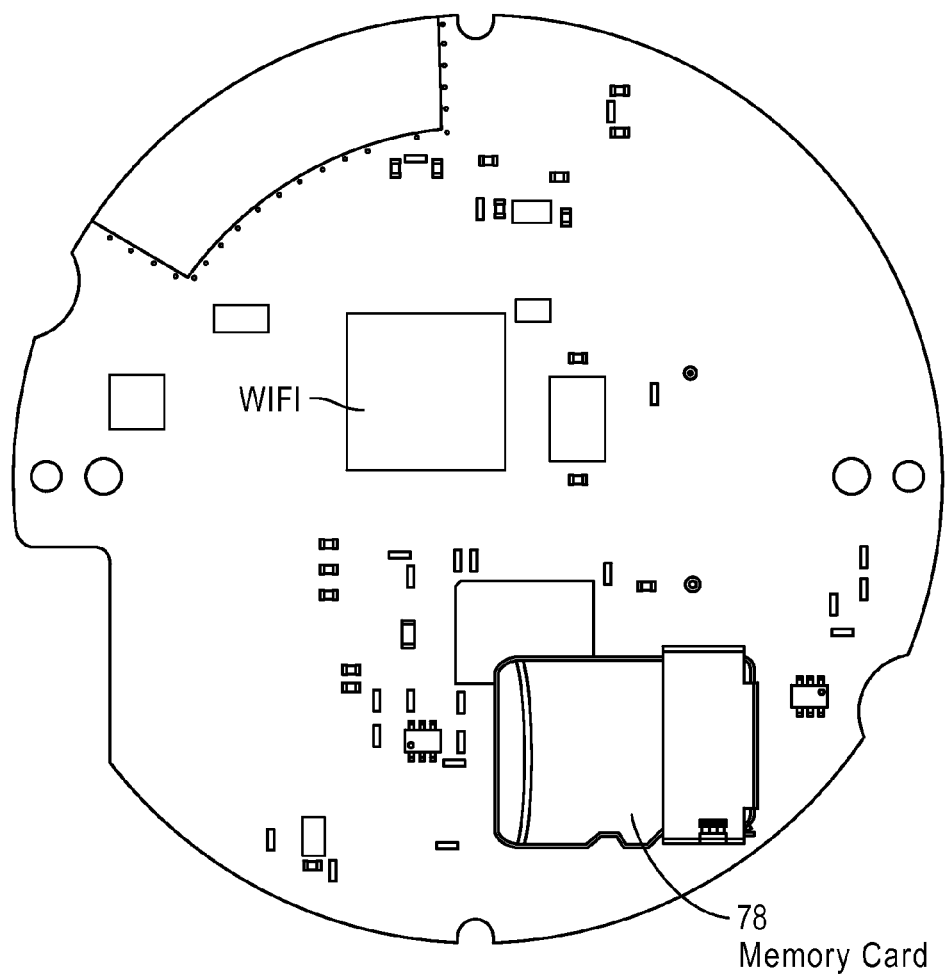
FIG. 1(d) illustrates one embodiment of a middle board of the FIG. 1(a) user monitoring device.
Figure 1E:
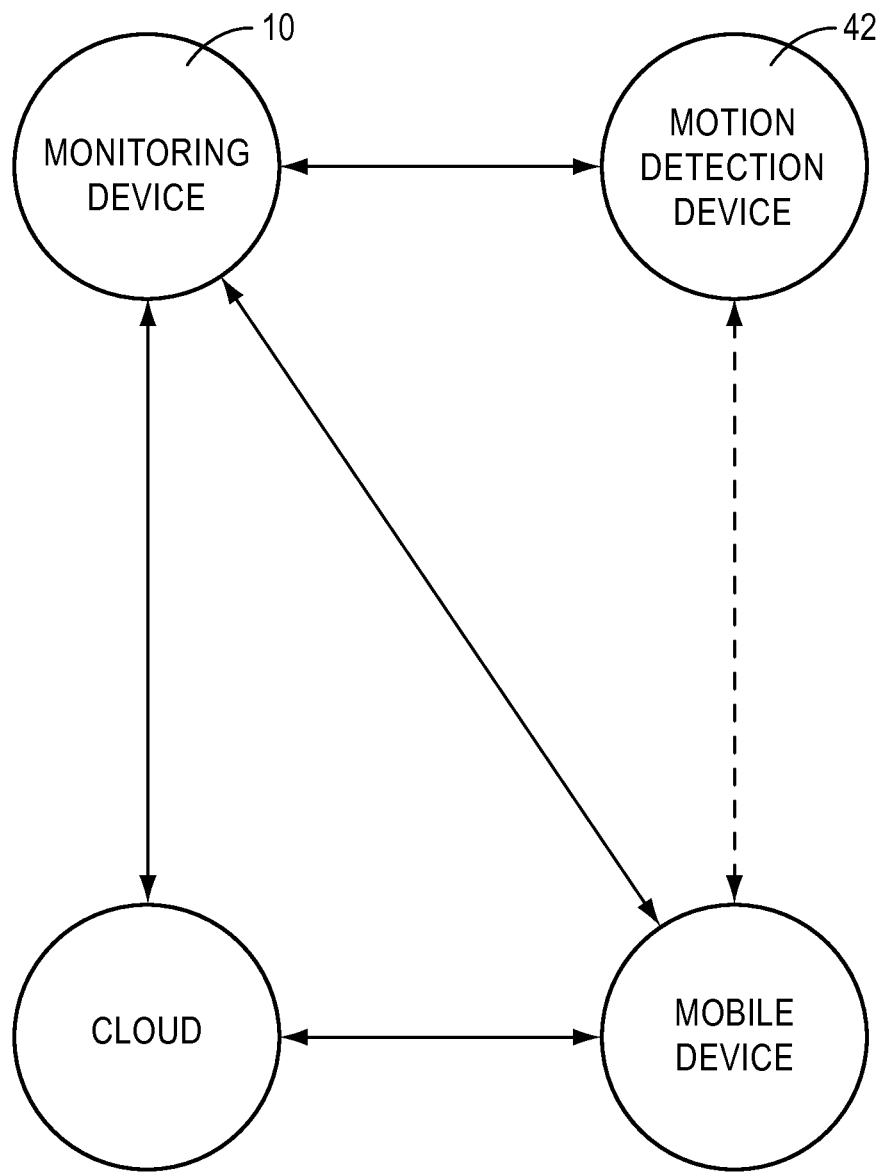
FIG. 1(e) illustrates the communication between the cloud, client or mobile device, monitoring device 10 and motion detection device 42.

FIG. 1(e) illustrates the communication between the cloud, client or mobile device, monitoring device 10 and motion detection device 42.

Figure 2A:
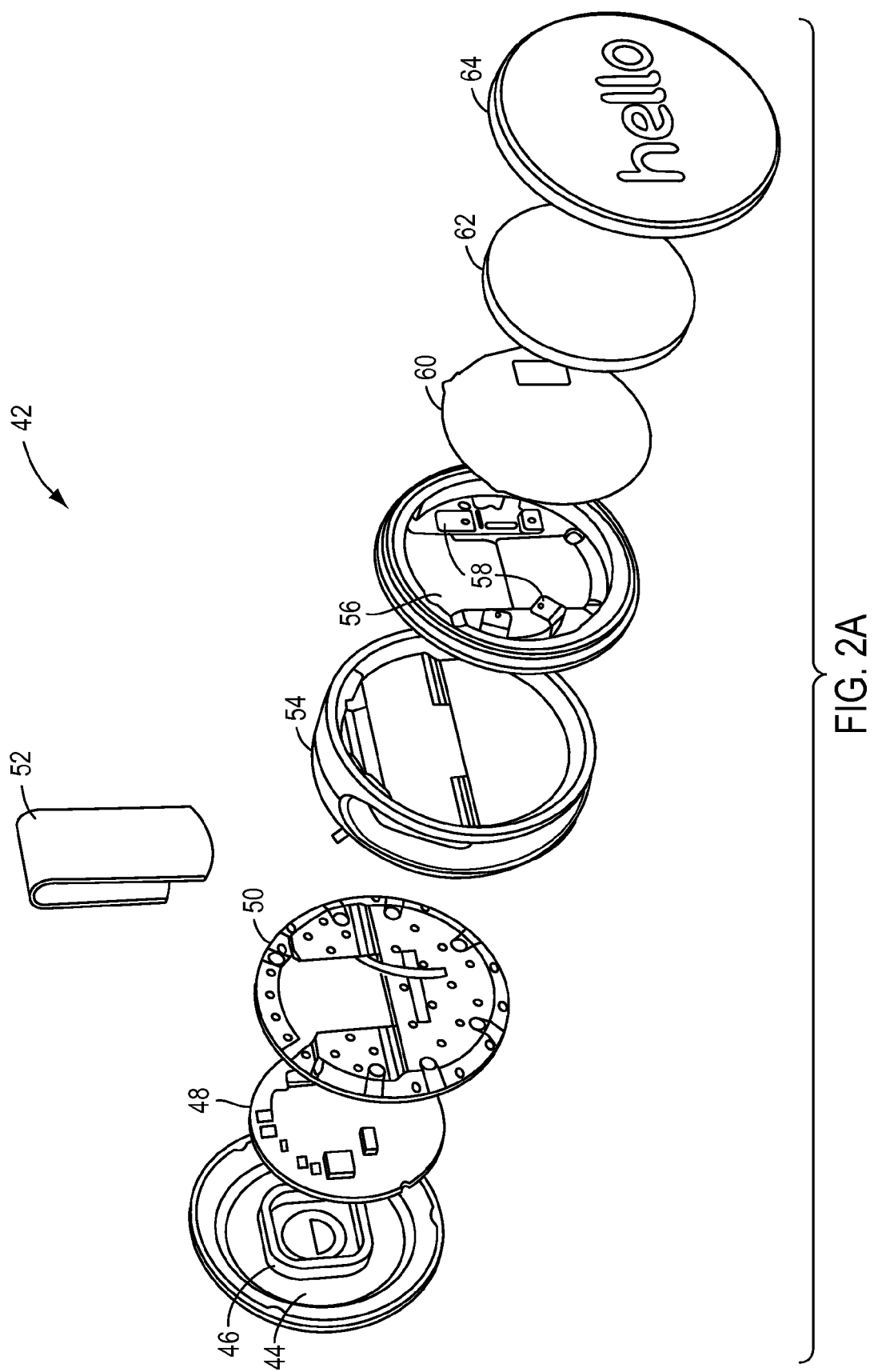
FIG. 2(a) is an exploded view of one embodiment of a motion/movement/gesture detective device of the present invention.

FIG. 2(a) illustrates one embodiment of a detection device, (hereafter motion/movement/gesture detective device 42). In one embodiment motion/movement/gesture/detection device 42 includes a front shell 44, an emitter gasket 46, a circuit board 48, a front support structure 50, a spring steel 52, an elastomer foot 54, a rear support structure 56, a battery terminal 58, a terminal insulting film 60, a coin cell battery 62 and a back shell 64.

The monitor device 10 can include a plurality of ports, generally denoted as 65, that: (i) allow light to be transmitted from an interior of the monitor device to the user for visual feedback, (ii) a port 65 for the proximity sensor 68, and (iii) one or more ports 65 that allows for the introduction of air. In one embodiment the ports 65 for the introduction for air are located at a bottom portion of monitor device 10.

As illustrated in FIGS. 1(b), 1 (c) and 1(d) in one embodiment the monitor device 10 includes four different printed circuit boards (PCBs). In one embodiment a top PCB includes an ambient light sensor 66, a proximity sensor 70, a microphone 72 and speaker module 74. These are utilized for user interaction and also to pick up the most data. There are no sensors on the middle PCB. In one embodiment the bottom PCB has one temperature/humidity sensor 76 as the USB for wall charging. A battery pact is optional. Air ducting inside the monitor device 10 is provided to direct particulates, including but not limited to dust, towards the particulate sensor 30.

In one embodiment the monitor device 10 includes one or more of a housing with a plurality of ports 65, and one or more of the following elements: proximity sensor; temperature sensor/humidity sensor; particulate sensor 30; light sensor 66; microphone 70; speaker 74; two RF transmitters 76 (BLE/ANT+WIFI); a memory card 78; and LED's 80.

In one embodiment the monitor device 10 lights up to indicate either that the user is alarmed, that something is wrong, or if everything is ok. This provides quick feedback to the user.

Figure 2B:
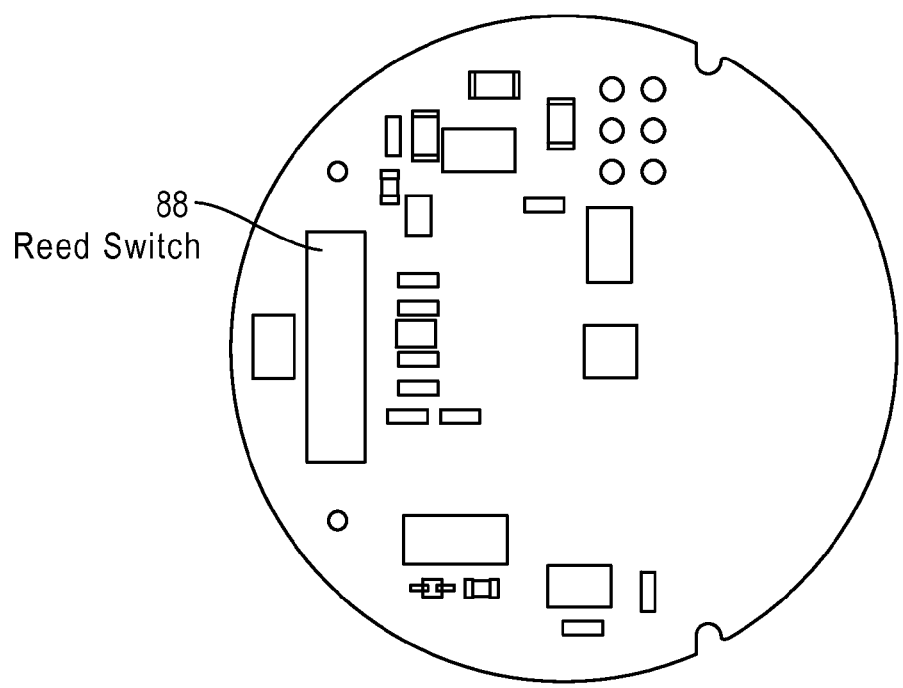
FIGS. 2(b) and 2(c) illustrate front and back surfaces of a board from the FIG. 2(a) motion/movement/gesture detection device with a reed switch and an accelerator.
Figure 2C:
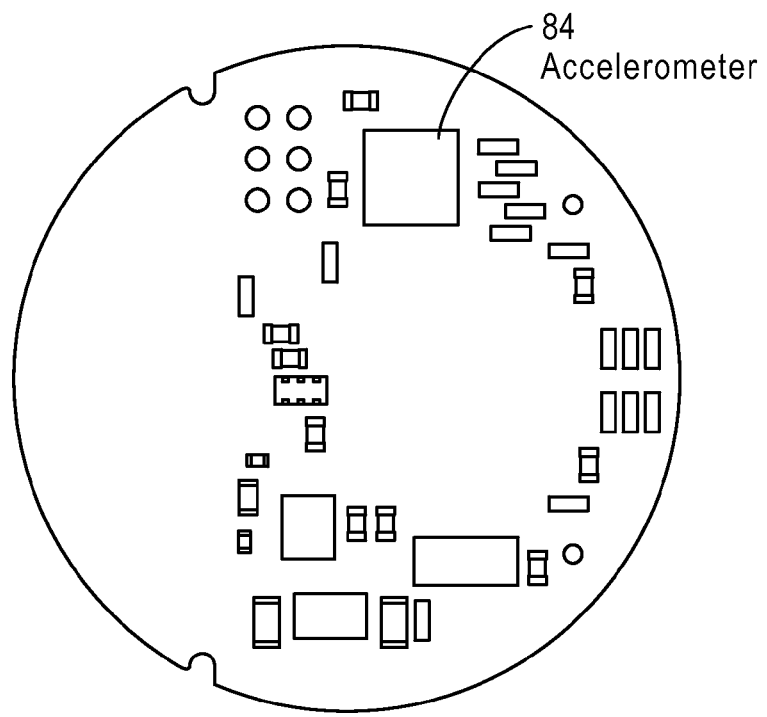

In one embodiment, illustrated in FIGS. 2(b) and 2(c) the motion/movement/gesture detection device 42 is provided that is located external to a monitor device 10 that includes one or more sensors. In one embodiment the motion/movement/gesture detection device 42 includes: an RF transmitter (BLE/ANT) 82, motion/movement/gesture detection detector 84; a central processing unit (CPU) 86, an RGB LED 88 and a reed switch 90. As a non-limiting example, motion/movement/gesture detection device 42 is attached to a pillow, bed cover, bed sheet, bedspread, and the like, in close enough proximity to the person being monitored that monitor device can detect signals from motion/movement/gesture detection device 42, and can be in the same room or a different room where the monitored person is.

In one embodiment the motion/movement/gesture detection device 42 is configured to detect motion, movement and the like, of a person over a certain threshold. When motion is detected, it wakes up the CPU 86 which processes the data emitted by the motion/movement/gesture detection device 42. The CPU 86 can optionally encrypt the data. The CPU 86 can broadcast the data collected through the RF transmitter.

In one embodiment the motion/movement/gesture detection device 42 is a position sensing device that is an accelerometer 84 which detects motion, movement/gesture and the like, of a person. As a non-limiting example, the accelerometer 84 provides a voltage output that is proportional to a detected acceleration. Suitable accelerometers are disclosed in, U.S. Pat. No. 8,347,720, U.S. Pat. No. 8,544, 326, U.S. Pat. No. 8,542,189, U.S. Pat. No. 8,522,596. EP0486657B1, EP 2428774 A1, incorporated herein by reference. In one embodiment the accelerometer reports X, Y, and X axis information.

In certain embodiments other motion/movement gesture sensing devices 42 can be utilized including but not limited to: position sensing devices including but not limited to, optical encoders, magnetic encoders, mechanical encoders, Hall Effect sensors, potentiometers, contacts with ticks and the like.

The motion/movement/gesture detection device 84 provides one or more outputs. In one embodiment the output is a single value that detects the most interesting motion of the person within a defined time period. As a non-limiting example, this can be 60 seconds. The interesting motion is defined as that which provides the most information relative to movement/motion/gesture, and the like, of the person, that is different from a normal pattern of movement/motion/gesture and the like, that are not common occurrences of the person's movement/motion and gesture.

The motion/movement/gesture detection device 42 communicates with the monitor device 10 over the ANT protocol. The data collected by the motion/movement/gesture detection device 42 can be is encrypted before being broadcasted. Any motion/movement/gesture detection device can 42 safely connect to any monitor device to transmit data.

In one embodiment the monitor device 10 can also communicate with the motion/movement/gesture detection device 42 to exchange configuration information.

The monitor device 10 communicates with a Cloud System 110. The monitor device uploads data to the Cloud System at some interval controlled by the Cloud System 110. In one embodiment the data uploaded contains information collected from all sensors that are included in the monitor device, including but not limited to, temperature, humidity, particulates, sound, light, proximity, motion/movement/gesture detection device data, as well as system information including the monitor device's unique identifier (mac address), remaining storage capacity, system logs, and the like. To verify integrity and authenticity of the data, a cryptographic hash is included in the data.

In one embodiment monitor device receives commands and data from the Cloud System after each upload. As non-limiting examples the commands can include but are not limited to: light commands (color, pattern, duration); sound commands (sound, pattern, duration); personalized data which again as a non-limiting example can include ideal temperature, humidity, particulate level and the like; and custom configuration for algorithms running on monitor device.

Values generated by the monitor device elements, e.g, sensors and other elements in the monitor device, are collected over a selected time period. As a non-limiting example, this time period can be one minute. Data is also accumulated from the motion/movement/gesture detection device. The combination of the motion/movement/gesture detection device and the monitor device data and the combination of the two is then synchronized at a server. As a non-limiting example, the server can be at the Cloud System 110. Following the synchronization the server communicates instructions to the monitor device.

In one embodiment a person's mobile device communicates with monitor device over Bluetooth Low Energy (BLE). As non-limiting examples, the mobile device can send command information directed to one or more of: securely sharing WiFi credentials; activating sensors, including but not limited to light, sound and the like; exchanges system state information; communicates maintenance operations; and the like.

In one embodiment mobile devices communicate securely to the Cloud System through mobile applications. As non-limiting examples these applications provide the ability to create an account, authenticate, access the data uploaded by monitor device, and perform other actions (set alarm, and the like) that are not typical of the environment where the client is.

In one embodiment the Cloud System pushes information to mobile devices when notification is needed.

In one embodiment monitor device performs audio classification and similarity detection to identify sounds and extra sound characteristics on the most interesting sounds that are not common occurrences.

In one embodiment algorithms are used to detect start, end, duration and quality of sleep activity. In one embodiment additional algorithms are used to detect motion events caused by another motion/movement/gesture detection device user sharing a same bed.

In one embodiment the Cloud System includes three subsystems which can communicate asynchronously. This can include one or more of a: (i) synchronization system that is responsible for receiving data uploaded by monitor device, verifying authenticity and integrity of the data uploaded, sending commands to monitor device 10. The data received is then queued for processing; (ii) processing service which is responsible for data analysis, persistence and transformation, visualization; and a presentation service for presenting data to the authenticated users.

In one embodiment the motion/movement/gesture detection device 42 analyzes motion data collected in real-time by an accelerometer. An algorithm processes the data and extract the most statistically interesting readings. At a predefined interval, the data collected is broadcasted to a monitor device.

In one embodiment the motion/movement/gesture detection device 42 is a three axis accelerometer. As a non-limiting example, the three axis accelerometer is modeled as $$zk=ak+gk+bk+vA;k$$

Where zk is the sensor output at time k, ak corresponds to the accelerations due to linear and rotational movement, bk is the o_set of the sensor, and vA; k is the observed noise. Accelerometer In one embodiment of the present invention, illustrated in FIG. 3, the motion/movement/gesture detection device 42 includes an accelerometer 110 generally mounted on a circuit board 130 within the motion/movement/gesture detection device 42. The accelerometer 110 may be a single axis accelerometer (x axis), a dual axis accelerometer (x, y axes) or a tri-axis accelerometer (x, y, z axes). The electronic device may have multiple accelerometers that each measure 1, 2 or 3 axes of acceleration. The accelerometer 110 continuously measures acceleration producing a temporal acceleration signal. The temporal acceleration signal may contain more than one separate signal. For example, the temporal acceleration signal may include 3 separate acceleration signals, i.e. one for each axis. In certain embodiments, the accelerometer includes circuitry to determine if a tap and or shake have occurred by taking the derivative of the acceleration signal. In some embodiments, the accelerometer includes a computation module for comparing the derivative values to a threshold to determine if a tap and or shake have occurred. In other embodiments, the accelerometer outputs a temporal acceleration signal and the computation module takes the first derivative of the acceleration signal produce a plurality of derivative values. The computation module can then compare the first derivative values to a predetermined threshold value that is stored in a memory of the computation module to determine if a tap and or shake have occurred.

Figure 4:
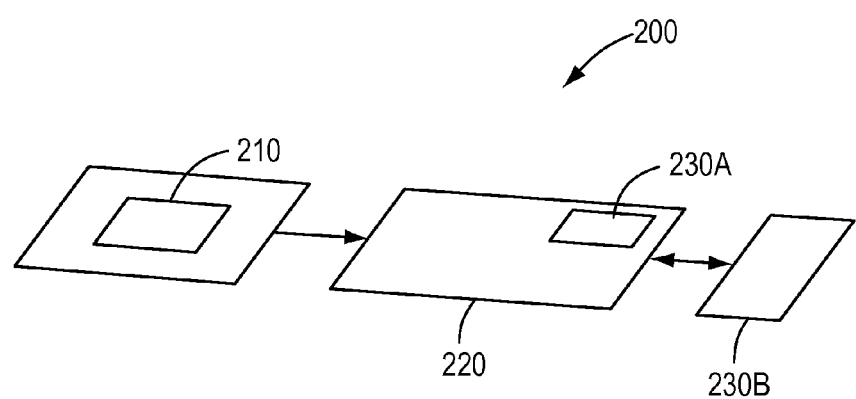
FIG. 4 is a first embodiment of a tap and or shake detection system.

FIG. 4 shows a first embodiment of the tap and or shake detection system 200 that includes a computation module 220 and the accelerometer 210. The accelerometer output signal is received by a computation module 220 that is electrically coupled to the accelerometer 210 and that is running (executing/interpreting) software code. It should be understood by one of ordinary skill in the art that the software code could be implemented in hardware, for example as an ASIC chip or in an FPGA or a combination of hardware and software code. The computation module running the software receives as input the data from the accelerometer and takes the derivative of the signal. For example, the accelerometer may produce digital output values for a given axis that are sampled at a predetermined rate. The derivative of the acceleration values or "jerk" can be determined by subtracting the N and N-1 sampled values. The acceleration values may be stored in memory 230A, 230B either internal to or external to the computation module 220 during the calculation of the derivative of acceleration.

Other methods/algorithms may also be used for determining the derivative of the acceleration. The jerk value can then be compared to a threshold. The threshold can be fixed or user-adjustable. If the jerk value exceeds the threshold then a tap and or shake is detected. In some embodiments, two threshold values may be present: a first threshold value for tap and or shakes about the measured axis in a positive direction and a second threshold for tap and or shakes about the axis in a negative direction. It should be recognized by one of ordinary skill in the art that the absolute value of the accelerometer output values could be taken and a single threshold could be employed for accelerations in both a positive and negative direction along an axis. When a tap and or shake have been detected, the computation unit can then forward a signal or data indicative of a tap and or shake as an input for another application/process. The application/process may use the detection of a tap and or shake as an input signal to perform an operation. For example, a tap and or shake may indicate that a device should be activated or deactivated (on/off). Thus, the tap and or shake detection input causes a program operating on the device to take a specific action. Other uses for tap and or shake detection include causing a cellular telephone to stop audible ringing when a tap and or shake is detected or causing a recording device to begin recording. These examples should not be viewed as limiting the scope of the invention and are exemplary only.

Figure 5:
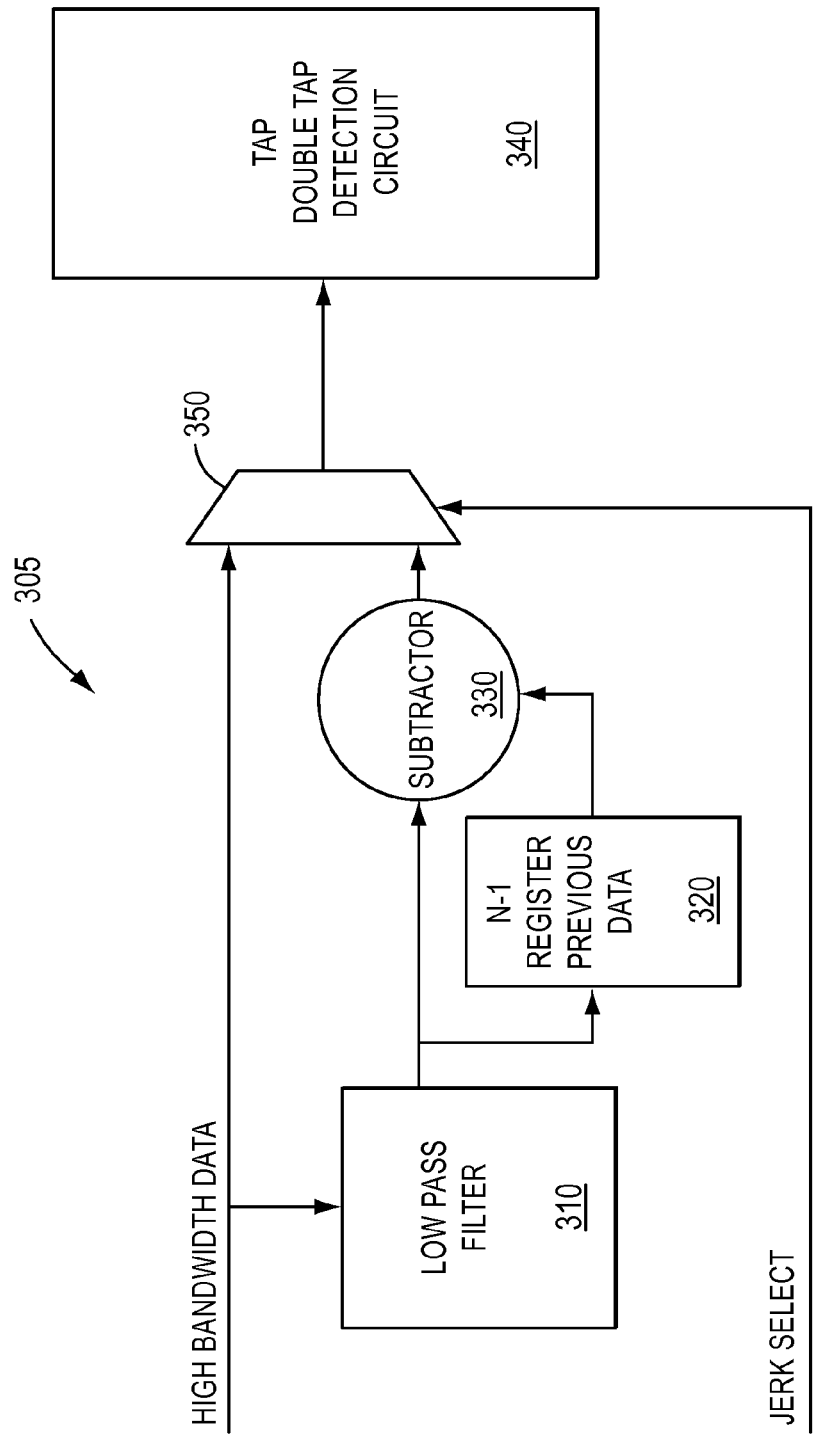
FIG. 5 is a second embodiment of a tap and or shake detection system that includes a subtraction circuit.

FIG. 5 shows a second embodiment of the tap and or shake detection system that uses a buffer for storing a temporal acceleration value along with a subtraction circuit. This embodiment can be used to retrofit an electronic device that already has a tap and or shake detection algorithm without needing to alter the algorithm. For purposes of this discussion, it will be assumed that the high bandwidth acceleration data is for a single axis. The acceleration data may include data from a multi-axis accelerometer.

The circuit shows high bandwidth data 300 from an accelerometer unit being used as input to the tap and or shake detection system 305. The high-bandwidth data 300 is fed to a multiplexor 350 and also to a low pass filter 310. The high bandwidth data 300 from the accelerometer is low pass filtered in order to reduce the data rate, so that the data rate will be compatible with the other circuit elements of the tap and or shake detection system 305. Therefore, the low pass filter is an optional circuit element if the data rate of the accelerometer is compatible with the other circuit elements. Once the acceleration data is filtered, the sampled data (N-1) is stored in a register 320. The next sampled data value (N) is passed to the subtraction circuit 330 along with the sampled value that is stored in the register (N-1) 320. As the N-1 data is moved to the subtraction circuit 330, the N data value replaces the N-1 value in the register 320. Not shown in the figure is a clock circuit that provides timing signals to the low pass filter 310, the register 320, and the subtraction circuit 330. The clock circuit determines the rate at which data is sampled and passed through the circuit elements. If the accelerometer samples at a different rate than the clock rate, the low pass filter can be used to make the accelerometer's output data compatible with the clock rate. The subtraction circuit 330 subtracts the N-1 value from the N value and outputs the resultant value. The resultant value is passed to the tap and or shakes detection circuit 340 when the jerk select command to the multiplexor is active. The acceleration data may also be passed directly to the tap and or shake detection circuit when there is no jerk select command. In certain embodiments of the invention, the accelerometer unit along with the register, subtraction circuit, and multiplexor are contained within the accelerometer package.

The tap and or shake detection circuit 340 may be a computation module with associated memory that stores the threshold jerk values within the memory. The tap and or shake detection circuit may be either internal to the accelerometer packaging or external to the accelerometer packaging. For example, in a cell phone that includes one or more processors, a processor can implement the functions of a computation module. The computation module 340 compares the resultant jerk value to the one or more threshold jerk values. In one embodiment, there is a positive and a negative threshold jerk value. If the resultant value exceeds the threshold for a tap and or shake in a positive direction or is below the threshold for a tap and or shake in a negative direction, the tap and or shake detection circuit indicates that a tap and or shake has occurred. The tap and or shake identification can be used as a signal to cause an action to be taken in a process or application. For example, if the electronic device is a cell phone and a tap and or shake are detected, the tap and or shake may cause the cell phone to mute its ringer.

In other embodiments, the computation module determines if a tap and or shake occurs and then can store this information along with timing information. When a second tap and or shake occurs, the computation module can compare the time between tap and or shakes to determine if a double tap and or shake has occurred. Thus, a temporal threshold between tap and or shakes would be indicative of a double tap and or shake. This determination could be similar to the double tap and or shake algorithms that are used for computer input devices. For example, a double click of a computer mouse is often required to cause execution of a certain routine within a computer program. Thus, the double tap and or shake could be used in a similar fashion.

Figure 6:
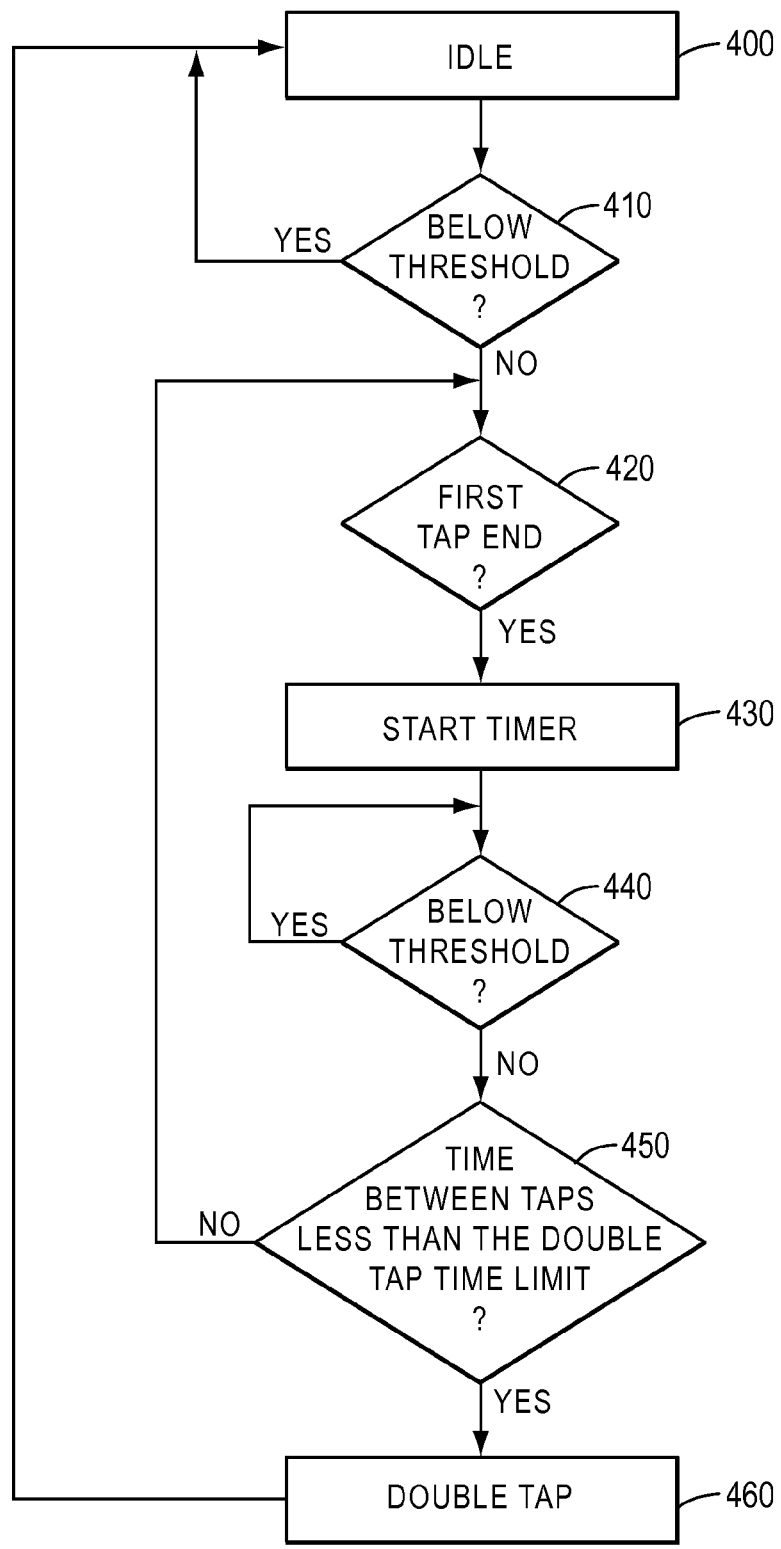
FIG. 6 is a flow chart that shows a method for detecting when a double tap and or shake has occurred.

FIG. 6 shows a flow chart for determining if a double tap and or shake have occurred. The system is initially at idle and the acceleration derivative values (jerk values) are below the threshold value 400. Each jerk value is compared to a threshold value 410. When the threshold value is exceeded, a first click or tap and or shake are identified. The system waits either a predetermined length or time or determines when the jerk value goes below the threshold to signify that the first tap and or shake has ended 420. A timer then starts and measures the time from the end of the first tap and or shake and the system waits for a second tap and or shake 430. The system checks each jerk value to see if the jerk value has exceeded the threshold 440. If the jerk value does not exceed the threshold the system waits. When the threshold is exceeded, the system determines the time between tap and or shakes and compares the time between tap and or shakes to a double tap and or shake limit 440. If the time between tap and or shakes is less than the double tap and or shake time limit, a double tap and or shake is recognized 450. If a double tap and or shake is not recognized, the present tap and or shake becomes the first tap and or shake and the system waits for the end of the first tap and or shake. When a second tap and or shake occurs, an identifier of the second tap and or shake i.e. a data signal, flag or memory location is changed and this information may be provided as input to a process or program. Additionally, when a double tap and or shake have been monitored, the methodology loops back to the beginning and waits for a new tap and or shake.

Figure 3:
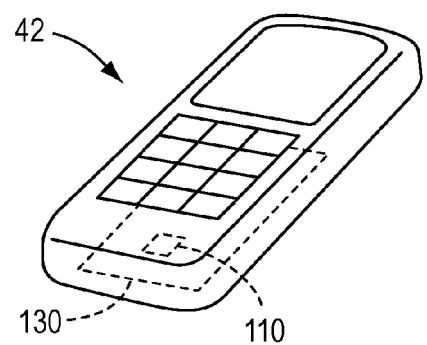
FIG. 3 is an image of an electronic device that contains an internal accelerometer.
Figure 7:
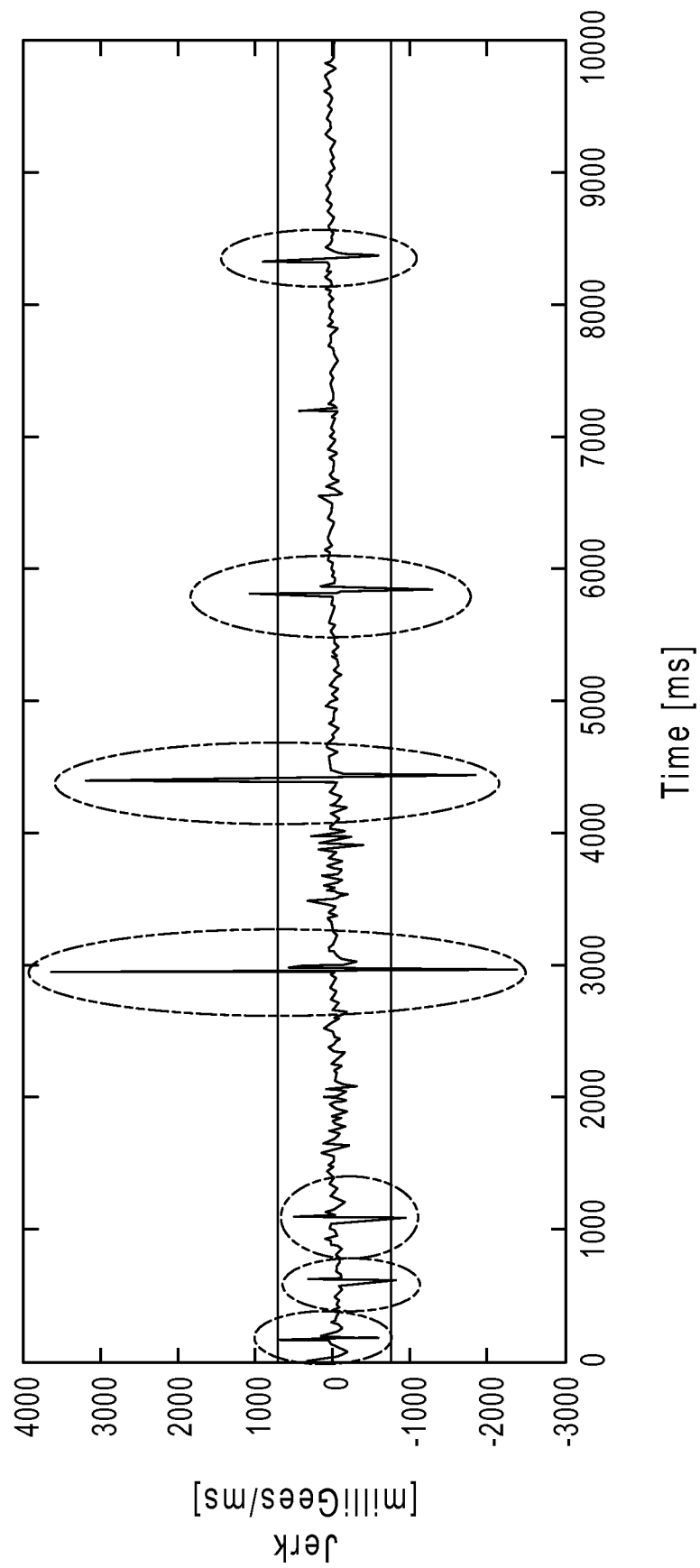
FIG. 7 is a graph that shows the derivative of acceleration with respect to time and includes thresholds for determining when a tap and or shake have occurred.

FIG. 7 shows a graph of the derivative of acceleration data ("jerk") with respect to time for the same series of accelerations as shown in FIG. 3. FIG. 5 provides a more accurate indication of tap and or shakes. FIG. 3 shows both false positive tap and or shake readings along with true negative readings. Thus, the acceleration measurement will not register some tap and or shakes and will also cause tap and or shakes to be registered when no tap and or shake was present. False positive readings occur, for example, when a user has a cell phone in his pocket and keys or other objects strike the cell phone due to movement of the user. These false readings are caused mainly because of the noise floor. By taking the derivative of the acceleration signal, the noise floor is lowered and the tap and or shake signals become more pronounced. Thus, false positive identifications of tap and or shakes are reduced with a lower noise floor. By requiring double tap and or shakes the number of false positives is reduced even further.

Audio

Figure 8:
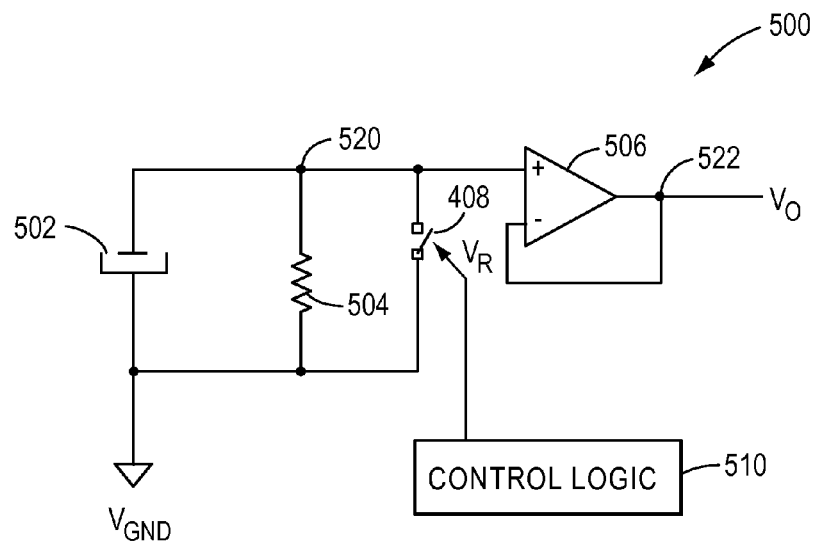
FIG. 8 is a block diagram of a microphone circuit according to the invention.

FIG. 8 is a block diagram of a microphone circuit 500 in one embodiment. In one embodiment, the microphone circuit 500 includes a transducer 502, a biasing resistor 504, a pre-amplifier 506, a switch circuit 508, and a control logic 510. The transducer 502 is coupled between a ground VGND and a node 520. The transducer 502 converts a sound into a voltage signal and outputs the voltage signal to the node 520. The biasing resistor 504 is coupled between the node 520 and the ground VGND and biases the node 520 with a DC voltage level of the ground voltage VGND. The pre-amplifier 506 receives the voltage signal output by the transducer 502 at the node 520 and amplifies the voltage signal to obtain an output signal Vo at a node 522. In one embodiment, the pre-amplifier 506 is a unity gain buffer.

The pre-amplifier 506 requires power supplied by a biasing voltage for amplifying the voltage signal output by the transducer 502. The switch circuit 508 is coupled between the node 520 and the ground voltage VGND. The switch circuit 508 therefore controls whether the voltage of the node 520 is set to the ground voltage VGND. When the microphone circuit 500 is reset, the control logic 510 enables a resetting signal VR to switch on the switch circuit 508, and the node 520 is therefore directly coupled to the ground VGND. When the microphone circuit 500 is reset, a biasing voltage VDD is applied to the pre-amplifier 506, and the voltage at the node 520 tends to have a temporary voltage increase. However, because the switch circuit 508 couples the node 520 the ground VGND, the voltage of the node 520 is kept at the ground voltage VGND and prevented from increasing, thus avoiding generation of the popping noise during the reset period. After a voltage status of the pre-amplifier 506 is stable at time T1, the control logic 510 switches off the switch circuit 508. The node 520 is therefore decoupled from the ground VGND, allowing the voltage signal generated by the transducer 502 to be passed to the pre-amplifier 506. Thus, the switch circuit 508 clamps the voltage of the node 520 to the ground voltage during the reset period, in which the biasing voltage VDD is just applied to the pre-amplifier 506.

Figure 12A:
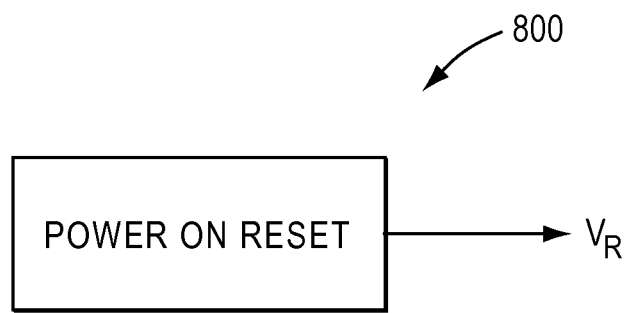
FIG. 12(a) is an embodiment of a control logic that can be used with the FIG. 4 embodiment.
Figure 12B:
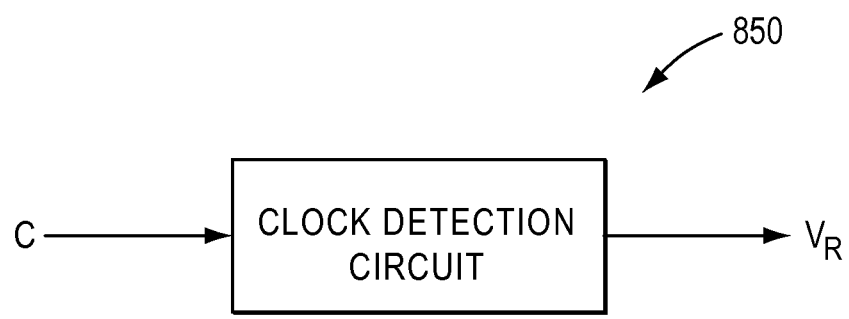
FIG. 12(b) is another embodiment of a control logic that can be used with the FIG. 4 embodiment.

Referring to FIG. 12(a), an embodiment of a control logic 510 is shown. In the embodiment, the control logic 510 is a power-on-reset circuit 800. The power-on-reset circuit 800 detects the power level of a biasing voltage of the pre-amplifier 506. When the power level of the biasing voltage of the pre-amplifier 506 is lower than a threshold, the power-on-reset circuit 800 enables the resetting signal VR to switch on the switch circuit 508, thus coupling the node 520 to the ground VGND to avoid generation of a popping noise. Referring to FIG. 12(b), another embodiment of a control logic 510 of FIG. 8 is shown. In the embodiment, the control logic 510 is a clock detection circuit 850. The clock detection circuit 850 detects a clock signal C frequency for operating the microphone circuit 500. When the frequency of the clock signal C is lower than a threshold, the clock detection circuit 850 enables the resetting signal VR to switch on the switch circuit 508, thus coupling the node 520 to the ground VGND to avoid generation of a popping noise.

Figure 9:
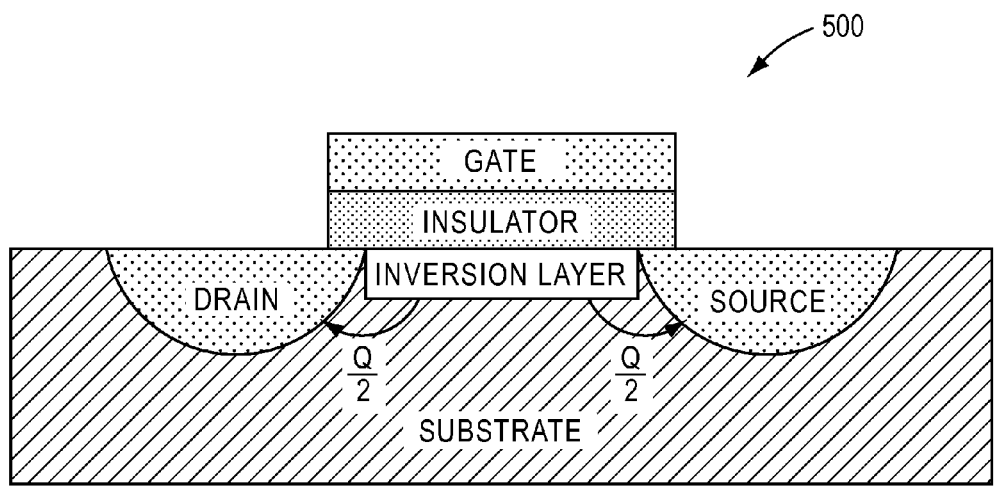
FIG. 9 is a cross-section view of an NMOS transistor.

In one embodiment, the switch circuit 508 is an NMOS transistor coupled between the node 520 and the ground VGND. The NMOS transistor has a gate coupled to the resetting voltage VR generated by the control logic 510. If the switch circuit 508 is an NMOS transistor, a noise is generated with a sound level less than that of the original popping noise when the control logic 510 switches off the switch circuit 508. Referring to FIG. 9, a cross-section view of an NMOS transistor 500 is shown. The NMOS transistor 500 has a gate on a substrate, and a source and a drain in the substrate. The gate, source, and drain are respectively coupled to the resetting signal VR, the ground voltage VGND, and the node 520. When the control logic 510 enables the resetting voltage VR to turn on the NMOS transistor 500, a charge amount Q is attracted by the gate voltage to form an inversion layer beneath the insulator. When the control logic 510 disables the resetting signal VR, the inversion layer vanishes, and a charge amount of Q/2 flows to the drain and source of the NMOS transistor 500, inducing a temporary voltage change at the node 520 and producing a noise.

Assume that the NMOS transistor 500 has a width of 1 μm, a length of 0.35 μm, and the resetting voltage is 1.8V, then the sheet capacitance of the gate oxide is 5 fF/μm2. The gate capacitance of the NMOS transistor 500 is therefore equal to (5 fF/μm2×1 μm×0.35 μm)=1.75 fF, and the charge Q stored in the inversion layer is therefore equal to (1.75 fF×1.8V)=3.15 fC. The drain of the NMOS transistor 500 has capacitance of (5 pF+200 fF)=5.2 pF, and the temporary voltage change at the node 520 is therefore equal to (3.15 fC/5.2 pF)=0.6 mV. With the NMOS switch 500, the node 520 of the microphone circuit 500 has a temporary voltage change of 0.6 mV instead of a popping noise of 64 mV during a reset period. The temporary voltage change of 0.6 mV, however, still produces an audible sound with a 63 dB sound pressure level. Thus, two more embodiments of the switch circuit 508 are introduced to solve the problem.

Figure 10:
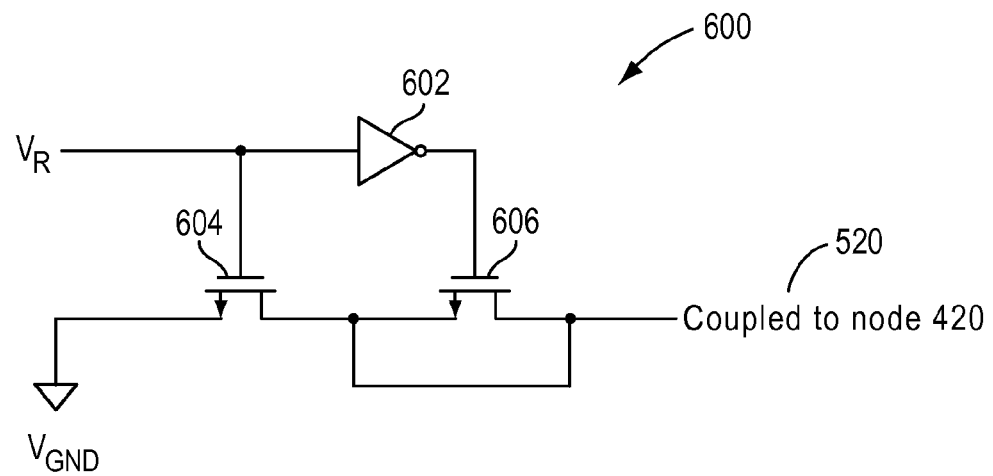
FIG. 10 is a block diagram of an embodiment of a switch circuit according to the invention.

Referring to FIG. 10, a block diagram of an embodiment of a switch circuit 600 is shown. The switch circuit 600 can include an inverter 602 and NMOS transistors 604 and 606, wherein a size of the NMOS transistor 606 is equal to a half of that of the NMOS transistor 604. When the control logic 510 enables the resetting signal VR, the NMOS transistor 604 is turned on to couple the node 520 to the ground voltage VGND, and the NMOS transistor 606 is turned off. When the control logic 510 disables the resetting signal VR, the NMOS transistor 604 is turned off to decouple the node 520 from the ground voltage VGND, and the NMOS transistor 606 is turned on. Charges originally stored in an inversion layer of the NMOS transistor 604 therefore flow from a drain of the NMOS transistor 604 to a source of the NMOS transistor 606 and are then absorbed by an inversion layer of the NMOS transistor 606, preventing the aforementioned problem of temporary voltage change of the node 520.

Figure 11:
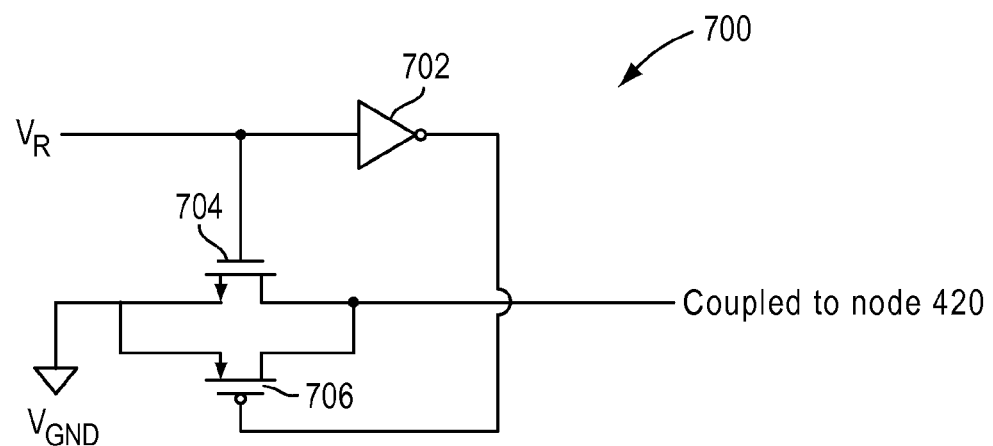
FIG. 11 is a block diagram of another embodiment of a switch circuit according to the invention.

Referring to FIG. 11, a block diagram of another embodiment of a switch circuit 700 according to the invention is shown. The switch circuit 700 comprises an inverter 702, an NMOS transistor 704, and a PMOS transistor 706, wherein a size of the NMOS transistor 704 is equal to that of the PMOS transistor 706. When the control logic 510 enables the resetting signal VR, the NMOS transistor 704 is turned on to couple the node 520 to the ground voltage VGND, and the PMOS transistor 706 is turned off. When the control logic 510 disables the resetting signal VR, the NMOS transistor 704 is turned off to decouple the node 520 from the ground voltage VGND, and the PMOS transistor 706 is turned on. Charges originally stored in an inversion layer of the NMOS transistor 704 therefore flow from a drain of the NMOS transistor 704 to a drain of the PMOS transistor 706 and are then absorbed by an inversion layer of the PMOS transistor 706, preventing the aforementioned problem of temporary voltage change of the node 520.

Gesture

Figure 13:
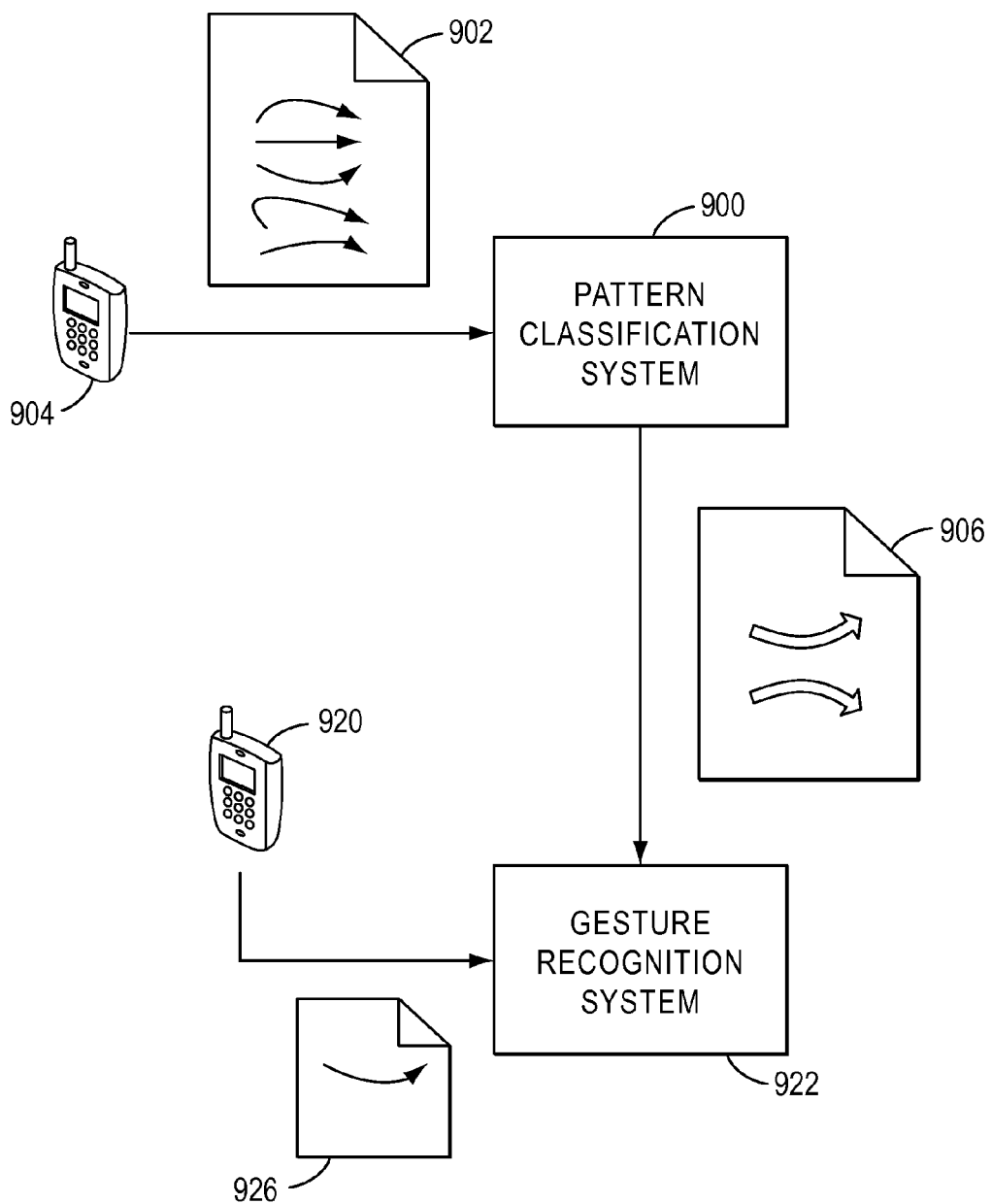
FIG. 13 is a diagram that provides an overview of motion pattern classification and gesture creation and recognition.

FIG. 13 is a diagram that provides an overview of motion pattern classification and gesture recognition. Motion pattern classification system 900 is a system including one or more computers programmed to generate one or more motion patterns from empirical data. Motion pattern classification system 900 can receive motion samples 902 as training data from at least one motion/movement/gesture detection device 904. Each of the motion samples 902 can include a time series of readings of a motion sensor of motion/movement/gesture detection device 904.

Motion pattern classification system 900 can process the received motion samples 902 and generate one or more motion patterns 906. Each of the motion patterns 906 can include a series of motion vectors. Each motion vector can include linear acceleration values, angular rate values, or both, on three axes of a Cartesian coordinate frame (e.g., X, Y, Z or pitch, yaw, roll). Each motion vector can be associated with a timestamp. Each motion pattern 906 can serve as a prototype to which motions are compared such that a gesture can be recognized. Motion pattern classification system 900 can send motion patterns 906 to motion/movement/gesture detection device 920 for gesture recognition.

Mobile device 920 can include, or be coupled to, gesture recognition system 922. Gesture recognition system 922 is a component of motion/movement/gesture detection device 920 that includes hardware, software, or both that are configured to identify a gesture based on motion patterns 906. Mobile device 920 can move (e.g., from a location A to a location B) and change orientations (e.g., from a face-up orientation on a table to an upright orientation near a face) following motion path 924. When motion/movement/gesture detection device 920 moves, a motion sensor of motion/movement/gesture detection device 920 can provide a series of sensor readings 926 (e.g., acceleration readings or angular rate readings). Gesture recognition system 922 can receive sensor readings 926 and filter sensor readings 926. Gesture recognition system 922 can compare the filtered sensor readings 926 with the motion patterns 906. If a match is found, motion/movement/gesture detection device 920 can determine that a gesture is recognized. Based on the recognized gesture, motion/movement/gesture detection device can perform a task associated with the motion patterns 906 (e.g., turning off a display screen of motion/movement/gesture detection device 920).

Figure 14:
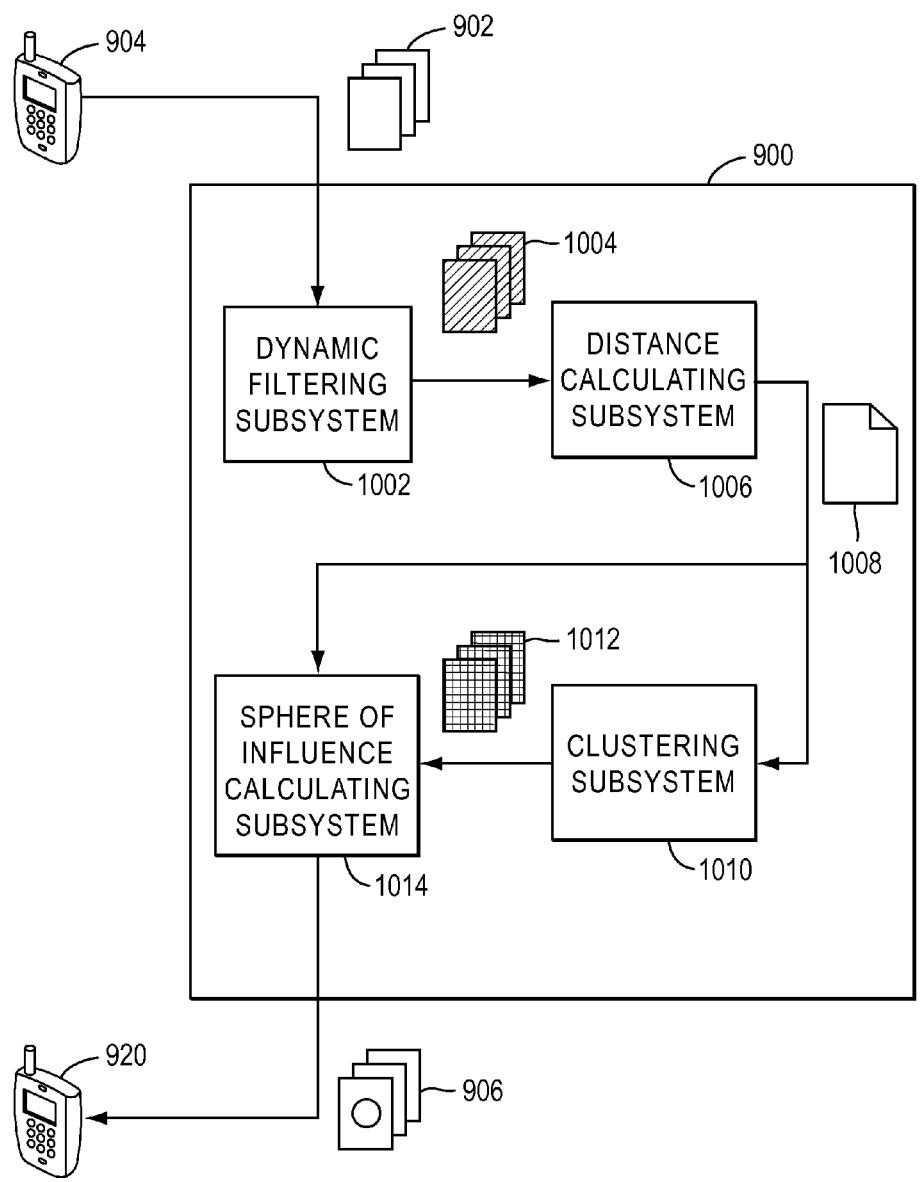
FIG. 14 is a block diagram of an exemplary system configured to perform operations of motion pattern classification.

FIG. 14 is a block diagram of an exemplary system configured to perform operations of motion pattern classification. Motion pattern classification system 900 can receive motion samples 902 from motion/movement/gesture detection device 904, generates prototype motion patterns 906 based on motion samples 902, and send prototype motion patterns 906 to motion/movement/gesture detection device 920.

Mobile device 904 is a device configured to gather motion samples 902. An application program executing on motion/movement/gesture detection device 904 can provide for display a user interface requesting a user to perform a specified physical gesture with motion/movement/gesture detection device 904 one or more times. The specified gesture can be, for example, a gesture of picking up motion/movement/gesture detection device 904 from a table or a pocket and putting motion/movement/gesture detection device 904 near a human face. The gesture can be performed in various ways (e.g., left-handed or right-handed). The user interface is configured to prompt the user to label a movement each time the user completes the movement. The label can be positive, indicating the user acknowledges that the just-completed movement is a way of performing the gesture. The label can be negative, indicating that the user specifies that the just-completed movement is not a way of performing the gesture. Mobile device 904 can record a series of motion sensor readings during the movement. Mobile device 904 can designate the recorded series of motion sensor readings, including those labeled as positive or negative, as motion samples 902. The portions of motion samples 902 that are labeled negative can be used as controls for tuning the motion patterns 906. Motion samples 902 can include multiple files, each file corresponding to a motion example and a series of motion sensor readings. Content of each file can include triplets of motion sensor readings (3 axes of sensed acceleration), each triplet being associated with a timestamp and a label. The label can include a text string or a value that designates the motion sample as a positive sample or a negative sample.

Motion pattern classification system 900 can include dynamic filtering subsystem 1002. Dynamic filtering subsystem 1002 is a component of motion pattern classification system 900 that is configured to generate normalized motion samples (also referred to as motion features) 1004 based on motion samples 902. Dynamic filtering subsystem 1002 can high-pass filter each of motion samples 902. High-pass filtering of motion samples 902 can include reducing a dimensionality of the motion example and compressing the motion sample in time such that each of motion samples 902 has a similar length in time. Further details of the operations of dynamic filtering subsystem 1002 will be described below in reference to FIG. 15.

Motion pattern classification system 900 can include distance calculating subsystem 1006. Distance calculating subsystem 1006 is a component of motion pattern classification system 100 that is configured to calculate a distance between each pair of motion features 1004. Distance calculating subsystem 1006 can generate a D-path matrix 1008 of distances. The distance between a pair of motion features 1004 can be a value that indicates a similarity between two motion features. Further details of the operations of calculating a distance between a pair of motion features 1004 and of the D-path matrix 1008 will be described below in reference to FIG. 16.

Figure 17:
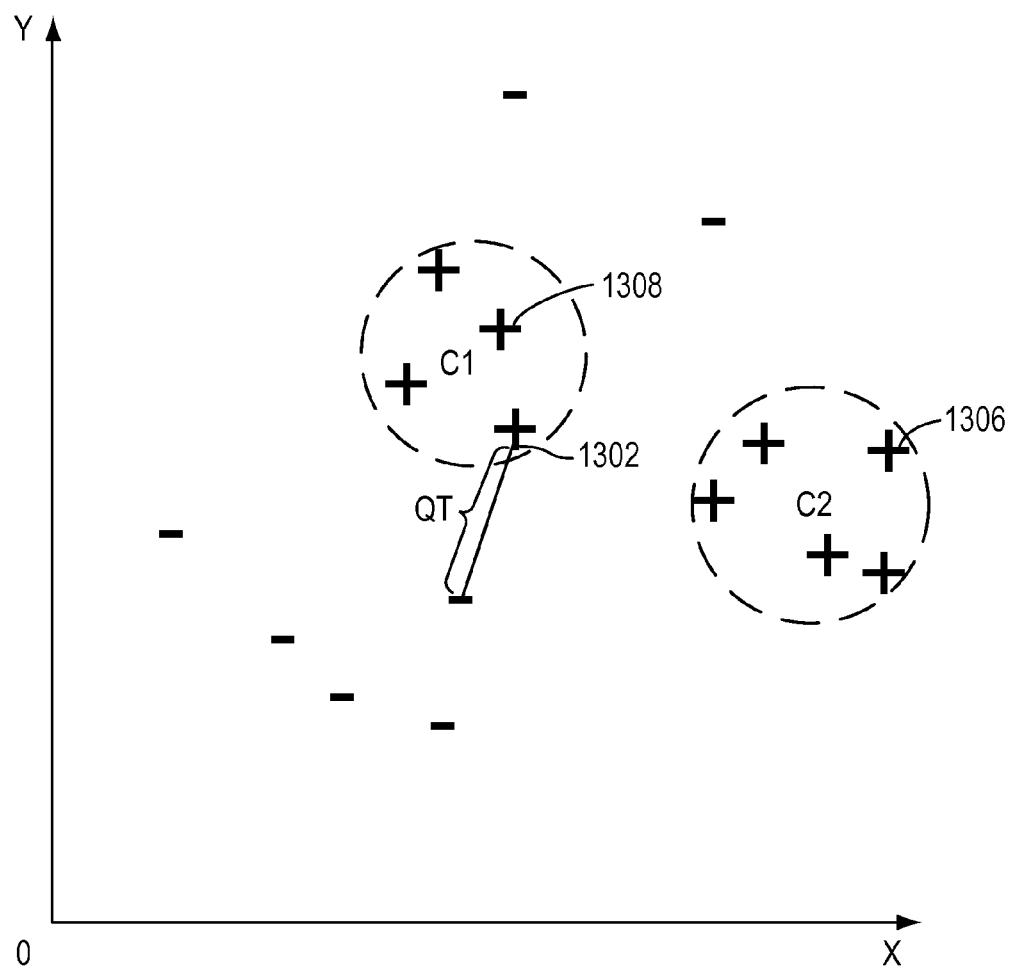
FIG. 17 is a diagram illustrating exemplary clustering techniques of motion pattern classification.

Motion pattern classification system 900 can include clustering subsystem 1010. Clustering subsystem 1010 is a component of motion pattern classification system 900 that is configured to generate one or more raw motion patterns 1012 based on the D-path matrix 1008 from the distance calculating system 1006. Each of the raw motion patterns 1012 can include a time series of motion vectors. The time series of motion vectors can represent a cluster of motion features 1004. The cluster can include one or more motion features 1004 that clustering subsystem 1010 determines to be sufficiently similar such that they can be treated as a class of motions. Further details of operations of clustering subsystem 1010 will be described below in reference to FIG. 17.

Motion pattern classification system 900 can include sphere-of-influence (SOI) calculating subsystem 1014. SOI calculating subsystem 1014 is a component of the motion pattern classification system 900 configured to generate one or more motion patterns 906 based on the raw motion patterns 1012 and the D-path matrix 1008. Each of the motion patterns 906 can include a raw motion pattern 1012 associated with an SOI. The SOI of a motion pattern is a value or a series of values that can indicate a tolerance or error margin of the motion pattern. A gesture recognition system can determine that a series of motion sensor readings match a motion pattern if the gesture recognition system determines that a distance between the series of motion sensor readings and the motion pattern is smaller than the SOI of the motion pattern. Further details of the operations of SOI calculating subsystem 1014 will be described below in reference FIGS. 18(*a*)-(*c*). The motion pattern classification system 900 can send the motion patterns 906 to device 920 to be used by device 920 to perform pattern-based gesture recognition.

Figure 15:
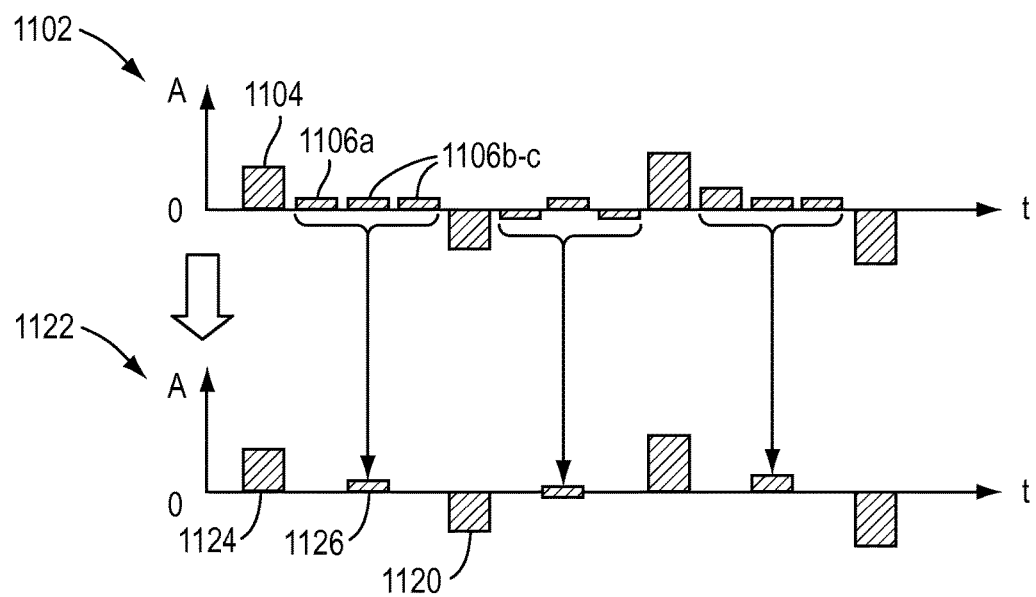
FIG. 15 is a diagram illustrating exemplary operations of dynamic filtering of motion example data.

FIG. 15 is a diagram illustrating exemplary operations of dynamic filtering motion sample data. Motion example 1102 can be one of the motion samples 902 (as described above in reference to FIGS. 13-14). Motion sample 1102 can include a time series of motion sensor readings 1104, 1106 *a-c*, 1108, etc. Each motion sensor reading is shown in one dimension ("A") for simplicity. Each motion sensor reading can include three acceleration values, one on each axis in a three dimensional space.

Dynamic filtering subsystem 1002 (as described in reference to FIG. 14) can receive motion sample 1102 and generate motion feature 1122. Motion feature 1122 can be one of the motion features 1004. Motion feature 1122 can include one or more motion vectors 1124, 1126, 1128, etc. To generate the motion feature 1122, dynamic filtering subsystem 1002 can reduce the motion sample 1102 in the time dimension. In some implementations, dynamic filtering subsystem 1002 can apply a filtering threshold to motion sample 1102. The filtering threshold can be a specified acceleration value. If a motion sensor reading 1108 exceeds the filtering threshold on at least one axis (e.g., axis X), dynamic filtering subsystem 1002 can process a series of one or more motion sensor readings 1106 *a-c* that precede the motion sensor reading 1108 in time. Processing the motion sensor readings 1106 *a-c* can include generating motion vector 1126 for replacing motion sensor readings 1106 *a-c*. Dynamic filtering subsystem 1002 can generate motion vector 1126 by calculating an average of motion sensor readings 1106 *a-c*. In a three-dimensional space, motion vector 1126 can include an average value on each of multiple axes. Thus, dynamic filtering subsystem 1002 can create motion feature 1122 that has fewer data points in the time series.

In some implementations, dynamic filtering subsystem 1002 can remove the timestamps of the motion samples such that motion feature 1122 includes an ordered series of motion vectors. The order of the series can implicitly indicate a time sequence. Dynamic filtering subsystem 1002 can preserve the labels associated with motion sample 1102. Accordingly, each motion vector in motion feature 1122 can be associated with a label.

Figure 16:
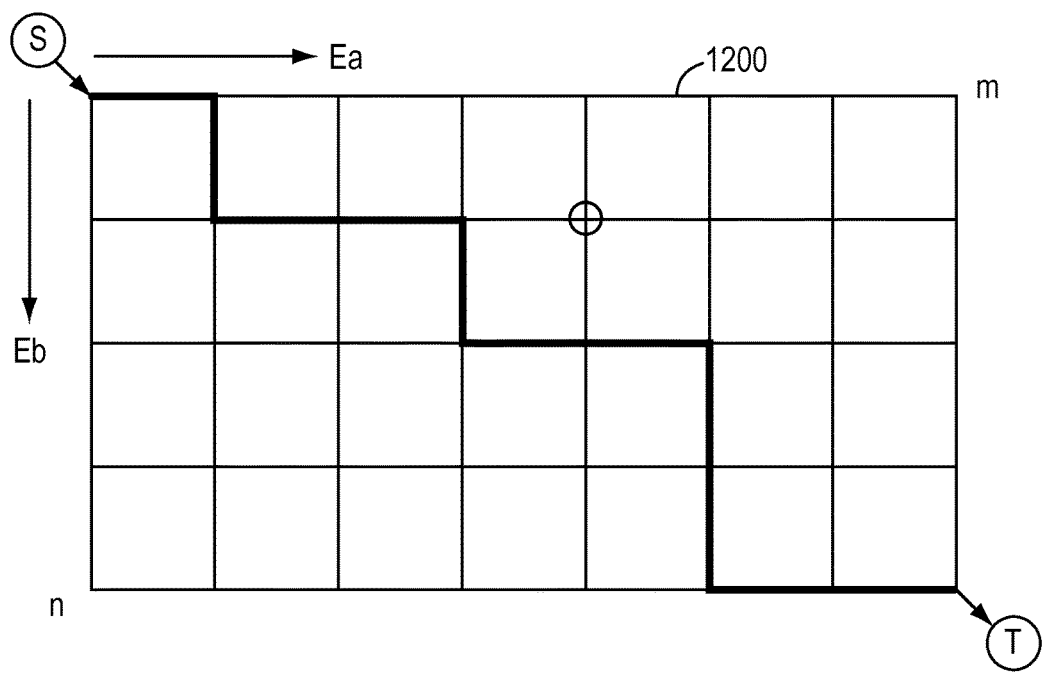
FIG. 16 is a diagram illustrating exemplary dynamic time warp techniques used in distance calculating operations of motion pattern classification.

FIG. 16 is a diagram illustrating exemplary dynamic time warp techniques used in distance calculating operations of motion pattern classification. Distance calculating subsystem 1006 (as described in reference to FIG. 14) can apply dynamic time warp techniques to calculate a distance between a first motion feature (e.g., Ea) and a second motion feature (e.g., Eb). The distance between Ea and Eb will be designated as D(Ea, Eb).

In the example shown, Ea includes a time series of m accelerometer readings r(a, 1) through r(a, m). Eb includes a time series of n accelerometer readings r(b, 1) through r(b, n). In some implementations, the distance calculating subsystem 1006 calculates the distance D(Ea, Eb) by employing a directed graph 1200. Directed graph 1200 can include m×n nodes. Each node can be associated with a cost. The cost of a node (i, j) can be determined based on a distance between accelerometer readings r(a, i) and r(b, j). For example, node 1202 can be associated with a distance between accelerometer readings r(a, 5) of Ea and accelerometer readings r(b, 2) of Eb. The distance can be a Euclidean distance, a Manhattan distance, or any other distance between two values in an n-dimensional space (e.g., a three-dimensional space).

Distance calculating subsystem 1006 can add a directed edge from a node (i, j) to a node (i, j+1) and from the node (i, j) to a node (i+1, j). The directed edges thus can form a grid, in which, in this example, multiple paths can lead from the node (1, 1) to the node (m, n).

Distance calculating subsystem 1006 can add, to directed graph 1200, a source node S and a directed edge from S to node (1, 1), and target node T and a directed edge from node (m, n) to T. Distance calculating subsystem 1006 can determine a shortest path (e.g., the path marked in bold lines) between S and T, and designate the cost of the shortest path as the distance between motion features Ea and Eb.

When distance calculating subsystem 1006 receives y of motion features E1 . . . Ey, distance calculating subsystem 1006 can create a y-by-y matrix, an element of which is a distance between two motion features. For example, element (a, b) of the y-by-y matrix is the distance D(Ea, Eb) between motion features Ea and Eb. Distance calculating subsystem 1006 can designate the y-by-y matrix as D-path matrix 1008 as described above in reference to FIG. 14.

Figure 20:
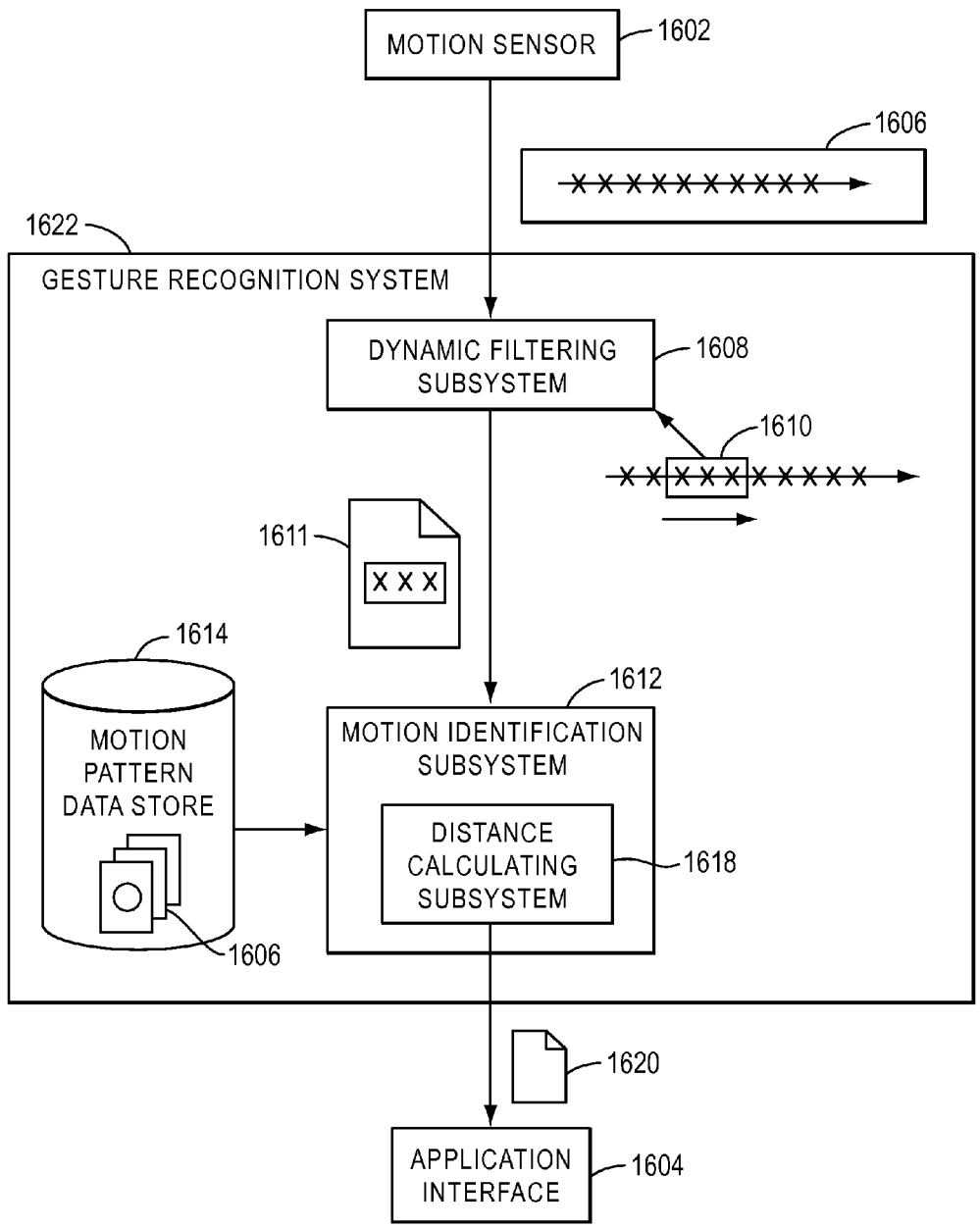
FIG. 20 is a block diagram illustrating an exemplary system configured to perform operations of gesture creation and recognition.

FIG. 20 is a diagram illustrating exemplary clustering techniques of motion pattern classification. The diagram is shown in a two-dimensional space for illustrative purposes. In some implementations, the clustering techniques are performed in a three-dimensional space. Clustering subsystem 1006 (as described in reference to FIG. 14) can apply quality threshold techniques to create exemplary clusters of motions C1 and C2.

Clustering subsystem 1006 can analyze D-path matrix 1008 as described above in references to FIG. 14 and FIG. 16 and the motion features 1004 as described above in reference to FIG. 14. Clustering subsystem 1006 can identify a first class of motion features 1004 having a first label (e.g., those labeled as "positive") and a second class of motion features 1004 having a second label (e.g., those labeled as "negative"). From D-path matrix 1008, clustering subsystem 1006 can identify a specified distance (e.g., a minimum distance) between a first class motion feature (e.g., "positive" motion feature 1302) and a second class motion feature (e.g., "negative" motion feature 1304). The system can designate this distance as Dmin(EL1, EL2), where L1 is a first label, and L2 is a second label. The specified distance can include the minimum distance adjusted by a factor (e.g., a multiplier k) for controlling the size of each cluster. Clustering subsystem 1006 can designate the specified distance (e.g., kDmin(EL1, EL2)) as a quality threshold.

Clustering subsystem 1006 can select a first class motion feature E1 (e.g., "positive" motion feature 1302) to add to a first cluster C1. Clustering subsystem 1006 can then identify a second first class motion feature E2 whose distance to E1 is less than the quality threshold, and add E2 to the first cluster C1. Clustering subsystem 1006 can iteratively add first class motion features to the first cluster C1 until all first class motion features whose distances to E1 are each less than the quality threshold has been added to the first cluster C1.

Clustering subsystem 1006 can remove the first class motion features in C1 from further clustering operations and select another first class motion feature E2 (e.g., "positive" motion feature 1306) to add to a second cluster C2. Clustering subsystem 1006 can iteratively add first class motion features to the second cluster C2 until all first class motion features whose distances to E2 are each less than the quality threshold have been added to the second cluster C2. Clustering subsystem 1006 can repeat the operations to create clusters C3, C4, and so on until all first class motion features are clustered.

Clustering subsystem 1006 can generate a representative series of motion vectors for each cluster. In some implementations, clustering subsystem 1006 can designate as the representative series of motion vectors a motion feature (e.g., motion feature 1308 illustrated in FIG. 17) that is closest to other motion samples in a cluster (e.g., cluster C1). Clustering subsystem 1006 can designate the representative series of motion vectors as a raw motion pattern (e.g., one of raw motion patterns 1012 as described above in reference to FIG. 14). To identify an example that is closest to other samples, clustering subsystem 1006 can calculate distances between pairs of motion features in cluster C1, and determine a reference distance for each motion sample. The reference distance for a motion sample can be maximum distance between the motion sample and another motion sample in the cluster. Clustering subsystem 1006 can identify motion feature 1308 in cluster C1 that has the minimum reference distance and designate motion feature 1308 as the motion pattern for cluster C1.

Figure 18A:
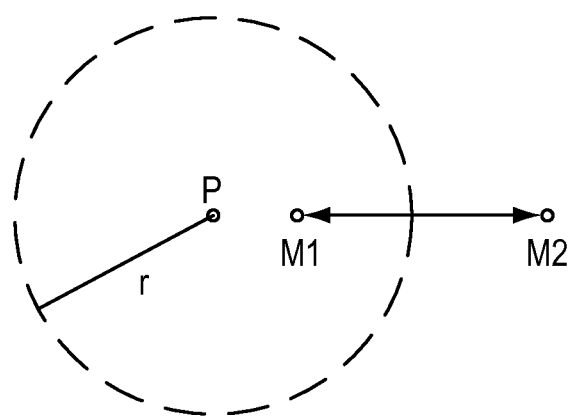
FIG. 18(a)-(c) are diagrams illustrating exemplary techniques of determining a sphere of influence of a motion pattern.
Figure 18B:
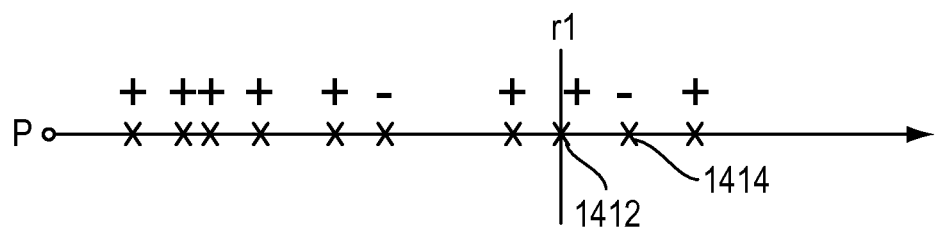
Figure 18C:
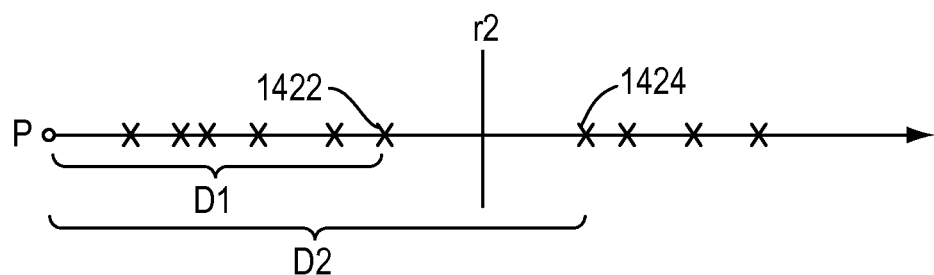

FIGS. 18(a)-(c) are diagrams illustrating techniques for determining a sphere of influence of a motion pattern. FIG. 18(a) is an illustration of a SOI of a motion pattern P. The SOI has a radius r that can be used as a threshold. If a distance between a motion M1 and the motion pattern P does not exceed r, a gesture recognition system can determine that motion M1 matches motion P. The match can indicate that a gesture is recognized. If a distance between a motion M2 and the motion pattern P exceeds r, the gesture recognition system can determine that motion M2 does not match motion P.

FIG. 18B is an illustration of exemplary operations of SOI calculating subsystem 1014 (as described above in reference to FIG. 14) for calculating a radius r1 of a SOI of a raw motion pattern P based on classification. SOI calculating subsystem 1014 can rank motion features 1004 based on a distance between each of the motion features 1004 and a raw motion pattern P. SOI calculating subsystem 1014 can determine the radius r1 based on a classification threshold and a classification ratio, which will be described below.

The radius r1 can be associated with a classification ratio. The classification ratio can be a ratio between a number of first class motion samples (e.g., "positive" motion samples) within distance r1 from the raw motion pattern P and a total number of motion samples (e.g., both "positive" and "negative" motion samples) within distance r1 from the motion pattern P.

SOI calculating subsystem 1014 can specify a classification threshold and determine the radius r1 based on the classification threshold. SOI calculating subsystem 1014 can increase the radius r1 from an initial value (e.g., 0) incrementally according to the incremental distances between the ordered motion samples and the raw motion pattern P. If, after r1 reaches a value (e.g., a distance between motion feature 1012 and raw motion pattern P), a further increment of r1 to a next closest distance between a motion feature (e.g., motion feature 1414) and raw motion pattern P will cause the classification ratio to be less than the classification threshold, SOI calculating subsystem 1014 can designate the value of r1 as a classification radius of the ROI.

FIG. 18(c) is an illustration of exemplary operations of SOI calculating subsystem 1014 (as described above in reference to FIG. 14) for calculating a density radius r2 of a SOI of raw motion pattern P based on variance. SOI calculating subsystem 1014 can rank motion features 1004 based on a distance between each of the motion features 1004 and a motion pattern P. SOI calculating subsystem 1014 can determine the density radius r2 based on a variance threshold and a variance value, which will be described in further detail below.

The density radius r2 can be associated with a variance value. The variance value can indicate a variance of distance between each of the motion samples that are within distance r2 of the raw motion pattern P. SOI calculating subsystem 1014 can specify a variance threshold and determine the density radius r2 based on the variance threshold. SOI calculating subsystem 1014 can increase a measuring distance from an initial value (e.g., 0) incrementally according to the incremental distances between the ordered motion samples and the motion pattern P. If, after the measuring distance reaches a value (e.g., a distance between motion feature 1422 and raw motion pattern P), a further increment of measuring distance to a next closest distance between a motion feature (e.g., motion feature 1424) and the raw motion pattern P will cause the variance value to be greater than the variance threshold, SOI calculating subsystem 1014 can designate an average ((D1+D2)/2) of the distance D1 between motion feature 1422 and the motion pattern P and the distance D2 between motion feature 1424 and the motion pattern P as the density radius r2 of the SOI.

In some implementations, SOI calculating subsystem 1014 can select the smaller between the classification radius and the density radius of an SOI as the radius of the SOI. In some implementations, SOI calculating subsystem 1014 can designate a weighted average of the classification radius and the density radius of an SOI as the radius of the SOI.

Figure 19:
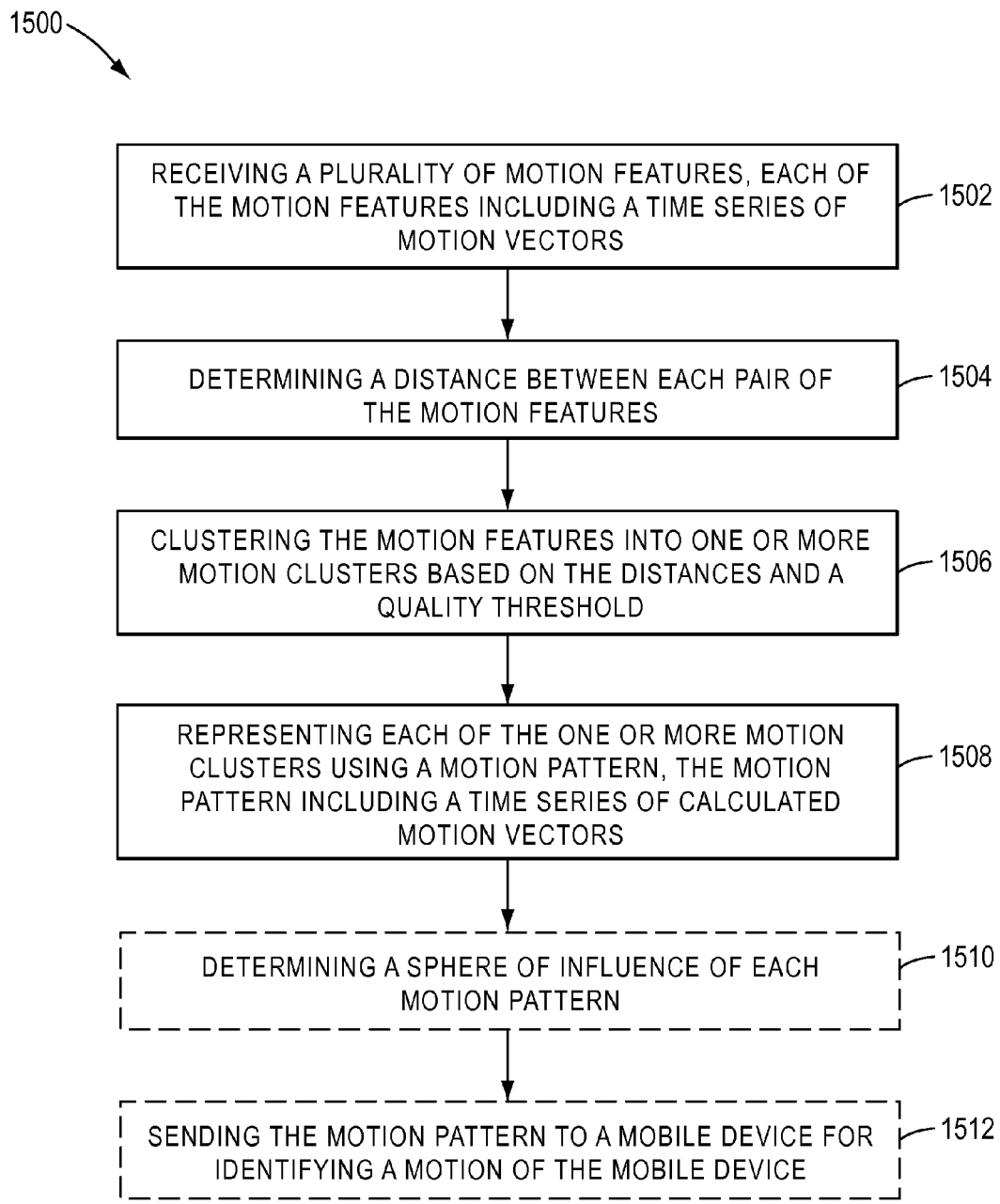
FIG. 19 is a flowchart illustrating an exemplary process of motion pattern classification.

FIG. 19 is a flowchart illustrating exemplary process 1500 of pattern-based gesture recognition. The process can be executed by a system including a motion/movement/gesture detection device.

The system can receive multiple motion patterns. Each of the motion patterns can include a time series of motion vectors. For clarity, the motion vectors in the motion patterns will be referred to as motion pattern vectors. Each of the motion patterns can be associated with an SOI. Each motion pattern vector can include a linear acceleration value, an angular rate value, or both, on each of multiple motion axes. In some implementations, each of the motion pattern vectors can include an angular rate value on each of pitch, roll, and yaw. Each of the motion patterns can include gyroscope data determined based on a gyroscope device of the motion/movement/gesture detection device, magnetometer data determined based on a magnetometer device of the motion/movement/gesture detection device, or gravimeter data from a gravimeter device of the motion/movement/gesture detection device. Each motion pattern vector can be associated with a motion pattern time. In some implementations, the motion pattern time is implied in the ordering of the motion pattern vectors.

The system can receive multiple motion sensor readings from a motion sensor built into or coupled with the system. The motion sensor readings can include multiple motion vectors, which will be referred to as motion reading vectors. Each motion reading vector can correspond to a timestamp, which can indicate a motion reading time. In some implementations, each motion reading vector can include an acceleration value on each of the axes as measured by the motion sensor, which includes an accelerometer. In some implementations, each motion reading vector can include a transformed acceleration value that is calculated based on one or more acceleration values as measured by the motion sensor. The transformation can include high-pass filtering, time-dimension compression, or other manipulations of the acceleration values. In some implementations, the motion reading time is implied in the ordering of the motion reading vectors.

The system can select, using a time window and from the motion sensor readings, a time series of motion reading vectors. The time window can include a specified time period and a beginning time. In some implementations, transforming the acceleration values can occur after the selection stage. The system can transform the selected time series of acceleration values.

The system can calculate a distance between the selected time series of motion reading vectors and each of the motion patterns. This distance will be referred to as a motion deviation distance. Calculating the motion deviation distance can include applying dynamic time warping based on the motion pattern times of the motion pattern and the motion reading times of the series of motion reading vectors. Calculating the motion deviation distance can include calculating a vector distance between (1) each motion reading vector in the selected time series of motion reading vectors, and (2) each motion pattern vector in the motion pattern. The system can then calculate the motion deviation distance based on each vector distance. Calculating the motion deviation distance based on each vector distance can include identifying a series of vector distances ordered according to the motion pattern times and the motion reading times (e.g., the identified shortest path described above with respect to FIG. 9B). The system can designate a measurement of the vector distances in the identified series as the motion deviation distance. The measurement can include at least one of a sum or a weighted sum of the vector distances in the identified series. The vector distances can include at least one of a Euclidean distance between a motion pattern vector and a motion reading vector or a Manhattan distance between a motion pattern vector and a motion reading vector.

The system can determine whether a match is found. Determining whether a match is found can include determining whether, according to a calculated motion deviation distance, the selected time series of motion reading vectors is located within the sphere of influence of a motion pattern (e.g., motion pattern P).

If a match is not found, the system slides the time window along a time dimension on the received motion sensor readings. Sliding the time window can include increasing the beginning time of the time window. The system can then perform operations 1504, 1506, 1508, and 1510 until a match is found, or until all the motion patterns have been compared against and no match is found.

If a match is found, a gesture is recognized. The system can designate the motion pattern P as a matching motion pattern. The system can perform (1014) a specified task based on the matching motion pattern. Performing the specific task can include at least one of: changing a configuration of a motion/movement/gesture detection device; providing a user interface for display, or removing a user interface from display on a motion/movement/gesture detection device; launching or terminating an application program on a motion/movement/gesture detection device; or initiating or terminating a communication between a motion/movement/gesture detection device and another device. Changing the configuration of the motion/movement/gesture detection device includes changing an input mode of the motion/movement/gesture detection device between a touch screen input mode and a voice input mode.

In some implementations, before performing the specified task, the system can apply confirmation operations to detect and eliminate false positives in matching. The confirmation operations can include examining a touch-screen input device or a proximity sensor of the motion/movement/gesture detection device. For example, if the gesture is "picking up the device," the device can confirm the gesture by examining proximity sensor readings to determine that the device is proximity to an object (e.g., a human face) at the end of the gesture.

FIG. 20 is a block diagram illustrating an exemplary system configured to perform operations of gesture recognition. The system can include motion sensor 1602, gesture recognition system, and application interface 1604. The system can be implemented on a mobile device.

Motion sensor 1602 can be a component of a mobile device that is configured to measure accelerations in multiple axes and produces motion sensor readings 1606 based on the measured accelerations. Motion sensor readings 1606 can include a time series of acceleration vectors.

Gesture recognition system can be configured to receive and process motion sensor readings 1606. Gesture recognition system 122 can include dynamic filtering subsystem 1608. Dynamic filtering subsystem 1608 is a component of the gesture recognition system that is configured to perform dynamic filtering on motion sensor readings 1606 in a manner similar to the operations of dynamic filtering subsystem. In addition, dynamic filtering subsystem 1608 can be configured to select a portion of motion sensor readings 1606 for further processing. The selection can be based on sliding time window 1610. Motion sensor 1602 can generate motion sensor readings 1606 continuously. Dynamic filtering subsystem 1608 can use the sliding time window 1610 to select segments of the continuous data, and generate normalized motion sensor readings 1611 based on the selected segments.

Gesture recognition system can include motion identification subsystem 1612. Motion identification subsystem 1612 is a component of gesture recognition system 1622 that is configured to determine whether normalized motion sensor readings 1611 match a known motion pattern. Motion identification subsystem 1612 can receive normalized motion sensor readings 1611, and access motion pattern data store 1614. Motion pattern data store 1614 includes a storage device that stores one or more motion patterns 106. Motion identification subsystem 1612 can compare the received normalized motion sensor readings 1611 with each of the stored motion patterns, and recognize a gesture based on the comparison.

Motion identification subsystem 1612 can include distance calculating subsystem 1618. Distance calculating subsystem 1618 is a component of motion identification subsystem 1612 that is configured to calculate a distance between normalized motion sensor readings 1611 and each of the motion patterns 106. If the distance between normalized motion sensor readings 1611 and a motion pattern P is within the radius of an SOI of the motion pattern P, motion identification subsystem 1612 can identify a match and recognize a gesture 1620. Further details of the operations of distance calculating subsystem 1618 will be described below in reference to FIGS. 21(*a*) and (*b*).

Motion identification subsystem 1612 can send the recognized gesture 1620 to application interface 1604. An application program or a system function of the mobile device can receive the gesture from application interface 1604 and perform a task (e.g., turning off a touch-input screen) in response.

Figure 21A:
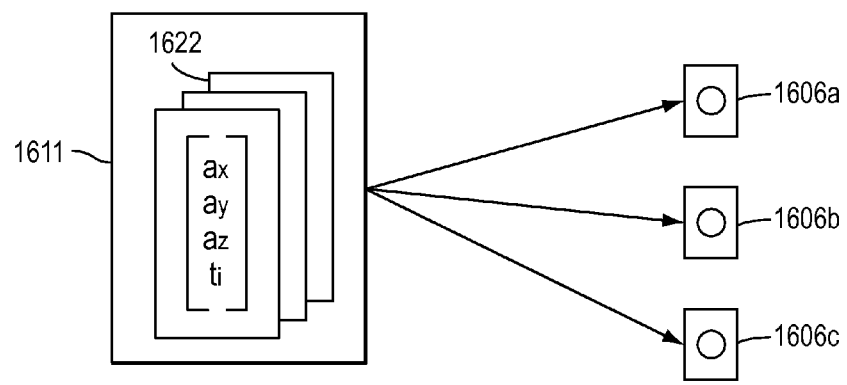
FIG. 21(a)-(b) are diagrams illustrating exemplary techniques of matching motion sensor readings to a motion pattern.
Figure 21B:
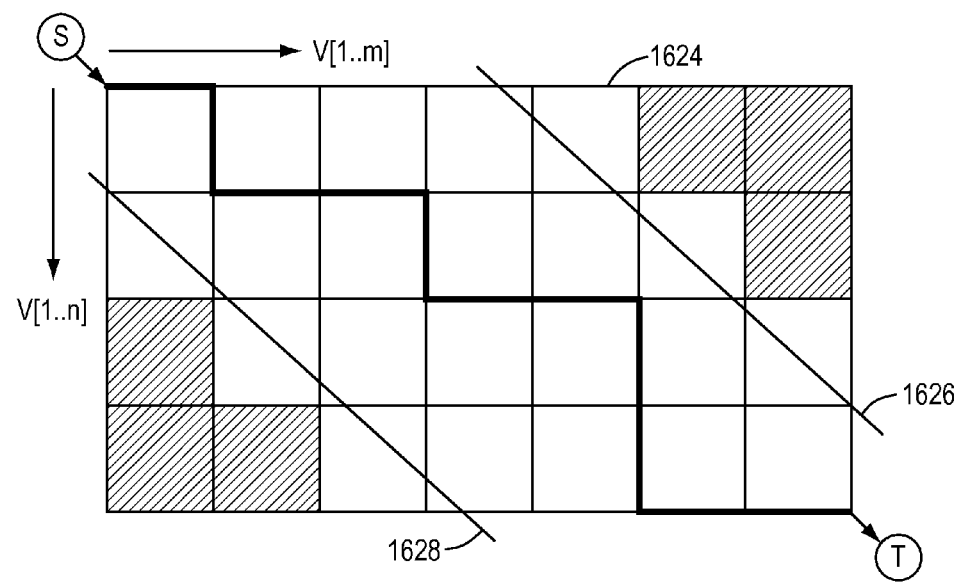

FIGS. 21(*a*) and (*b*) are diagrams illustrating techniques of matching motion sensor readings to a motion pattern. FIG. 21(*a*) illustrates an example data structure of normalized motion sensor readings 1611. Normalized motion sensor readings 1611 can include a series of motion vectors 1622. Each motion vector 1622 can include acceleration readings ax, ay, and az, for axes X, Y, and Z, respectively. In some implementations, each motion vector 1622 can be associated with a time ti, the time defining the time series. In some implementations, the normalized motion sensor readings 1611 designate the time dimension of the time series using an order of the motion vectors 1622. In these implementations, the time can be omitted.

Distance calculating subsystem 1618 (as described above in reference to FIG. 20) compares normalized motion sensor readings 1611 to each of the motion patterns 1606 *a*, 1606 *b*, and 1606 *c*. The operations of comparison are described in further detail below in reference to FIG. 21(*b*). A match between normalized motion sensor readings 1611 and any of the motion patterns 1606 *a*, 1606 *b*, and 1606 *c* can result in a recognition of a gesture.

FIG. 21(*b*) is a diagram illustrating distance calculating operations of distance calculating subsystem 1618. To perform the comparison, distance calculating subsystem 1618 can calculate a distance between the normalized motion sensor readings 1611, which can include readings R1, Rn, and a motion pattern (e.g., motion pattern 1606 *a*, 1606 *b*, or 1606 *c*), which can include motion vectors V1 . . . Vm. Distance calculating subsystem 1618 can calculate the distance using directed graph 1624 in operations similar to those described in reference to FIG. 20.

In some implementations, distance calculating subsystem 1618 can perform optimization on the comparing. Distance calculating subsystem 1618 can perform the optimization by applying comparison thresholds 1626 and 1628. Comparison thresholds 1626 and 1628 can define a series of vector pairs between which distance calculating subsystem 1618 performs a distance calculation. By applying comparison thresholds 1626 and 1628, distance calculating subsystem 1618 can exclude those calculations that are unlikely to yield a match. For example, a distance calculation between the first motion vector R1 in the normalized motion sensor readings 1611 and a last motion vector Vm of a motion pattern is unlikely to lead to a match, and therefore can be omitted from the calculations.

Distance calculating subsystem 1618 can determine a shortest path (e.g., the path marked in bold lines) in directed graph 1624, and designate the cost of the shortest path as a distance between normalized motion sensor readings 1611 and a motion pattern. Distance calculating subsystem 1618 can compare the distance with a SOI associated with the motion pattern. If the distance is less than the SOI, distance calculating subsystem 1618 can identify a match.

Figure 22:
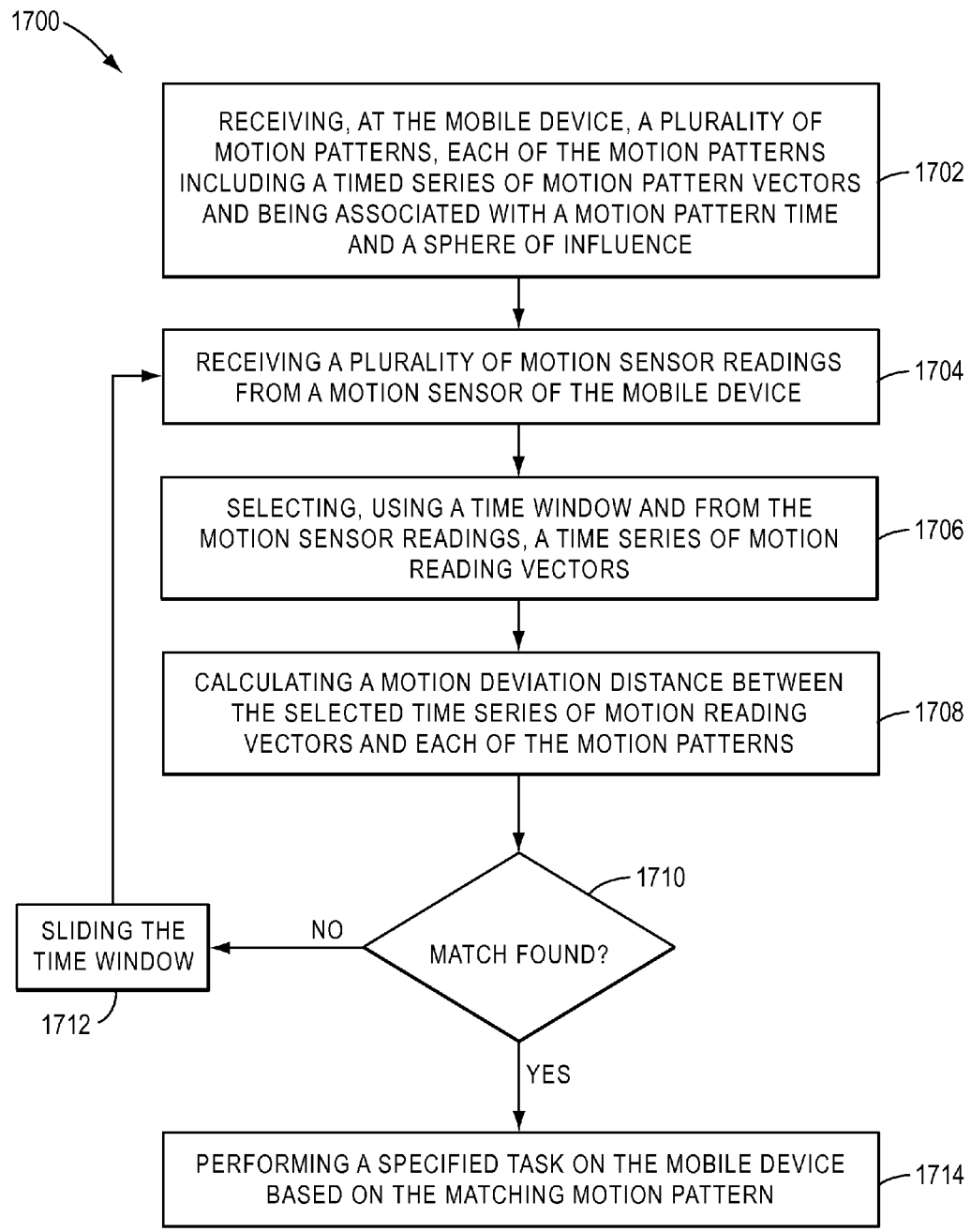
FIG. 22 is a flowchart illustrating an exemplary process of pattern-based gesture creation and recognition.

FIG. 22 is a flowchart illustrating exemplary process 1700 of pattern-based gesture recognition. The process can be executed by a system including a mobile device.

The system can receive (1702) multiple motion patterns. Each of the motion patterns can include a time series of motion vectors. For clarity, the motion vectors in the motion patterns will be referred to as motion pattern vectors. Each of the motion patterns can be associated with an SOI. Each motion pattern vector can include a linear acceleration value, an angular rate value, or both, on each of multiple motion axes. In some implementations, each of the motion pattern vectors can include an angular rate value on each of pitch, roll, and yaw. Each of the motion patterns can include gyroscope data determined based on a gyroscope device of the mobile device, magnetometer data determined based on a magnetometer device of the mobile device, or gravimeter data from a gravimeter device of the mobile device. Each motion pattern vector can be associated with a motion pattern time. In some implementations, the motion pattern time is implied in the ordering of the motion pattern vectors.

The system can receive (1704) multiple motion sensor readings from a motion sensor built into or coupled with the system. The motion sensor readings can include multiple motion vectors, which will be referred to as motion reading vectors. Each motion reading vector can correspond to a timestamp, which can indicate a motion reading time. In some implementations, each motion reading vector can include an acceleration value on each of the axes as measured by the motion sensor, which includes an accelerometer. In some implementations, each motion reading vector can include a transformed acceleration value that is calculated based on one or more acceleration values as measured by the motion sensor. The transformation can include high-pass filtering, time-dimension compression, or other manipulations of the acceleration values. In some implementations, the motion reading time is implied in the ordering of the motion reading vectors.

The system can select (1706), using a time window and from the motion sensor readings, a time series of motion reading vectors. The time window can include a specified time period and a beginning time. In some implementations, transforming the acceleration values can occur after the selection stage. The system can transform the selected time series of acceleration values.

The system can calculate (1708) a distance between the selected time series of motion reading vectors and each of the motion patterns. This distance will be referred to as a motion deviation distance. Calculating the motion deviation distance can include applying dynamic time warping based on the motion pattern times of the motion pattern and the motion reading times of the series of motion reading vectors. Calculating the motion deviation distance can include calculating a vector distance between (1) each motion reading vector in the selected time series of motion reading vectors, and (2) each motion pattern vector in the motion pattern. The system can then calculate the motion deviation distance based on each vector distance. Calculating the motion deviation distance based on each vector distance can include identifying a series of vector distances ordered according to the motion pattern times and the motion reading times (e.g., the identified shortest path described above with respect to FIG. 9B). The system can designate a measurement of the vector distances in the identified series as the motion deviation distance. The measurement can include at least one of a sum or a weighted sum of the vector distances in the identified series. The vector distances can include at least one of a Euclidean distance between a motion pattern vector and a motion reading vector or a Manhattan distance between a motion pattern vector and a motion reading vector.

The system can determine (1710) whether a match is found. Determining whether a match is found can include determining whether, according to a calculated motion deviation distance, the selected time series of motion reading vectors is located within the sphere of influence of a motion pattern (e.g., motion pattern P).

If a match is not found, the system slides (1712) the time window along a time dimension on the received motion sensor readings. Sliding the time window can include increasing the beginning time of the time window. The system can then perform operations 1704, 1706, 1708, and 1710 until a match is found, or until all the motion patterns have been compared against and no match is found.

If a match is found, a gesture is recognized. The system can designate the motion pattern P as a matching motion pattern. The system can perform (1714) a specified task based on the matching motion pattern. Performing the specific task can include at least one of: changing a configuration of a mobile device; providing a user interface for display, or removing a user interface from display on a mobile device; launching or terminating an application program on a mobile device; or initiating or terminating a communication between a mobile device and another device. Changing the configuration of the mobile device includes changing an input mode of the mobile device between a touch screen input mode and a voice input mode.

In some implementations, before performing the specified task, the system can apply confirmation operations to detect and eliminate false positives in matching. The confirmation operations can include examining a touch-screen input device or a proximity sensor of the mobile device. For example, if the gesture is "picking up the device," the device can confirm the gesture by examining proximity sensor readings to determine that the device is proximity to an object (e.g., a human face) at the end of the gesture.

Figure 23:
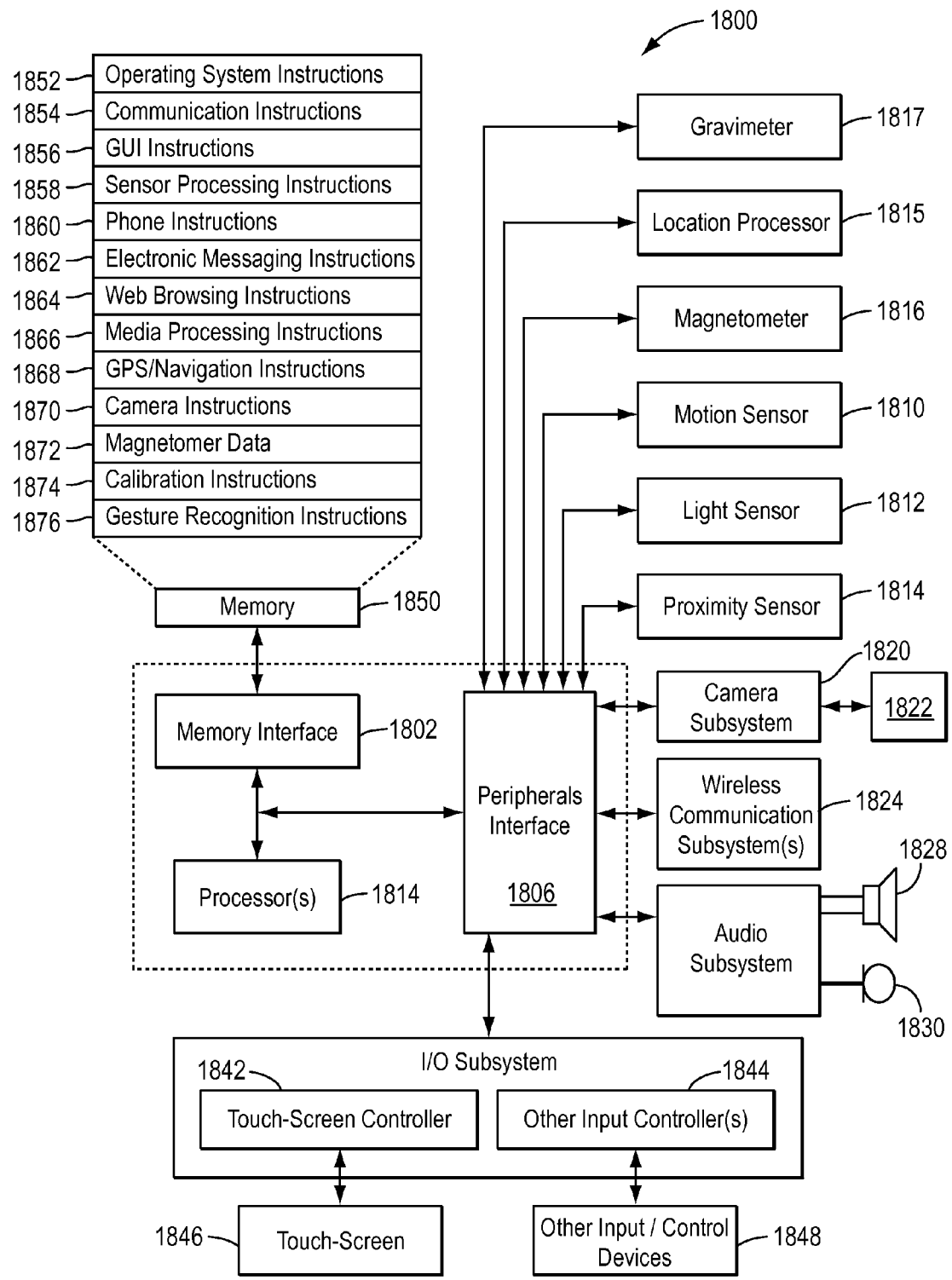
FIG. 23 is a block diagram illustrating exemplary device architecture of a monitoring system implementing the features and operations of pattern-based gesture creation and recognition.

FIG. 23 is a block diagram illustrating exemplary device architecture 1800 of a device implementing the features and operations of pattern-based gesture recognition. The device can include memory interface 1802, one or more data processors, image processors and/or processors 1804, and peripherals interface 1806. Memory interface 1802, one or more processors 1804 and/or peripherals interface 1806 can be separate components or can be integrated in one or more integrated circuits. Processors 1804 can include one or more application processors (APs) and one or more baseband processors (BPs). The application processors and baseband processors can be integrated in one single process chip. The various components in a motion/movement/gesture detection device, for example, can be coupled by one or more communication buses or signal lines.

Sensors, devices, and subsystems can be coupled to peripherals interface 1806 to facilitate multiple functionalities. For example, motion sensor 1810, light sensor 1812, and proximity sensor 1814 can be coupled to peripherals interface 1806 to facilitate orientation, lighting, and proximity functions of the motion/movement/gesture detection device. Location processor 1815 (e.g., GPS receiver) can be connected to peripherals interface 1806 to provide geo-positioning. Electronic magnetometer 1816 (e.g., an integrated circuit chip) can also be connected to peripherals interface 1806 to provide data that can be used to determine the direction of magnetic North. Thus, electronic magnetometer 1816 can be used as an electronic compass. Motion sensor 1810 can include one or more accelerometers configured to determine change of speed and direction of movement of the motion/movement/gesture detection device. Gravimeter 1817 can include one or more devices connected to peripherals interface 1806 and configured to measure a local gravitational field of Earth.

Camera subsystem 1820 and an optical sensor 1822, e.g., a charged coupled device (CCD) or a complementary metal-oxide semiconductor (CMOS) optical sensor, can be utilized to facilitate camera functions, such as recording photographs and video clips.

Communication functions can be facilitated through one or more wireless communication subsystems 1824, which can include radio frequency receivers and transmitters and/or optical (e.g., infrared) receivers and transmitters. The specific design and implementation of the communication subsystem 1824 can depend on the communication network(s) over which a motion/movement/gesture detection device is intended to operate. For example, a motion/movement/gesture detection device can include communication subsystems 1824 designed to operate over a CDMA system, a WiFi™ or WiMax™ network, and a Bluetooth™ network. In particular, the wireless communication subsystems 1824 can include hosting protocols such that the motion/movement/gesture detection device can be configured as a base station for other wireless devices.

Audio subsystem 1826 can be coupled to a speaker 1828 and a microphone 1830 to facilitate voice-enabled functions, such as voice recognition, voice replication, digital recording, and telephony functions.

I/O subsystem 1840 can include touch screen controller 1842 and/or other input controller(s) 1844. Touch-screen controller 1842 can be coupled to a touch screen 1846 or pad. Touch screen 1846 and touch screen controller 1842 can, for example, detect contact and movement or break thereof using any of a plurality of touch sensitivity technologies, including but not limited to capacitive, resistive, infrared, and surface acoustic wave technologies, as well as other proximity sensor arrays or other elements for determining one or more points of contact with touch screen 1846.

Other input controller(s) 1844 can be coupled to other input/control devices 1848, such as one or more buttons, rocker switches, thumb-wheel, infrared port, USB port, and/or a pointer device such as a stylus. The one or more buttons (not shown) can include an up/down button for volume control of speaker 1828 and/or microphone 1830.

In one implementation, a pressing of the button for a first duration may disengage a lock of the touch screen 1846; and a pressing of the button for a second duration that is longer than the first duration may turn power to a motion/movement/gesture detection device on or off. The user may be able to customize a functionality of one or more of the buttons. The touch screen 1846 can, for example, also be used to implement virtual or soft buttons and/or a keyboard.

In some implementations, a motion/movement/gesture detection device can present recorded audio and/or video files, such as MP3, AAC, and MPEG files. In some implementations, a motion/movement/gesture detection device can include the functionality of an MP3 player, such as an iPod™. A motion/movement/gesture detection device may, therefore, include a pin connector that is compatible with the iPod. Other input/output and control devices can also be used.

Memory interface 1802 can be coupled to memory 1850. Memory 1850 can include high-speed random access memory and/or non-volatile memory, such as one or more magnetic disk storage devices, one or more optical storage devices, and/or flash memory (e.g., NAND, NOR). Memory 1850 can store operating system 1852, such as Darwin, RTXC, LINUX, UNIX, OS X, WINDOWS, or an embedded operating system such as VxWorks. Operating system 1852 may include instructions for handling basic system services and for performing hardware dependent tasks. In some implementations, operating system 1852 can include a kernel (e.g., UNIX kernel).

Memory 1850 may also store communication instructions 1854 to facilitate communicating with one or more additional devices, one or more computers and/or one or more servers. Memory 1850 may include graphical user interface instructions 1856 to facilitate graphic user interface processing; sensor processing instructions 1858 to facilitate sensor-related processing and functions; phone instructions 1860 to facilitate phone-related processes and functions; electronic messaging instructions 1862 to facilitate electronic-messaging related processes and functions; web browsing instructions 1864 to facilitate web browsing-related processes and functions; media processing instructions 1866 to facilitate media processing-related processes and functions; GPS/Navigation instructions 1868 to facilitate GPS and navigation-related processes and instructions; camera instructions 1870 to facilitate camera-related processes and functions; magnetometer data 1872 and calibration instructions 1874 to facilitate magnetometer calibration. The memory 1850 may also store other software instructions (not shown), such as security instructions, web video instructions to facilitate web video-related processes and functions, and/or web shopping instructions to facilitate web shopping-related processes and functions. In some implementations, the media processing instructions 1866 are divided into audio processing instructions and video processing instructions to facilitate audio processing-related processes and functions and video processing-related processes and functions, respectively. An activation record and International Mobile Equipment Identity (IMEI) or similar hardware identifier can also be stored in memory 1850. Memory 1850 can include gesture recognition instructions 1876. Gesture recognition instructions 1876 can be a computer program product that is configured to cause the motion/movement/gesture detection device to recognize one or more gestures using motion patterns, as described in reference to FIGS. 13-22.

Each of the above identified instructions and applications can correspond to a set of instructions for performing one or more functions described above. These instructions need not be implemented as separate software programs, procedures, or modules. Memory 1850 can include additional instructions or fewer instructions. Furthermore, various functions of the motion/movement/gesture detection device may be implemented in hardware and/or in software, including in one or more signal processing and/or application specific integrated circuits.

Exemplary Operating Environment

Figure 24:
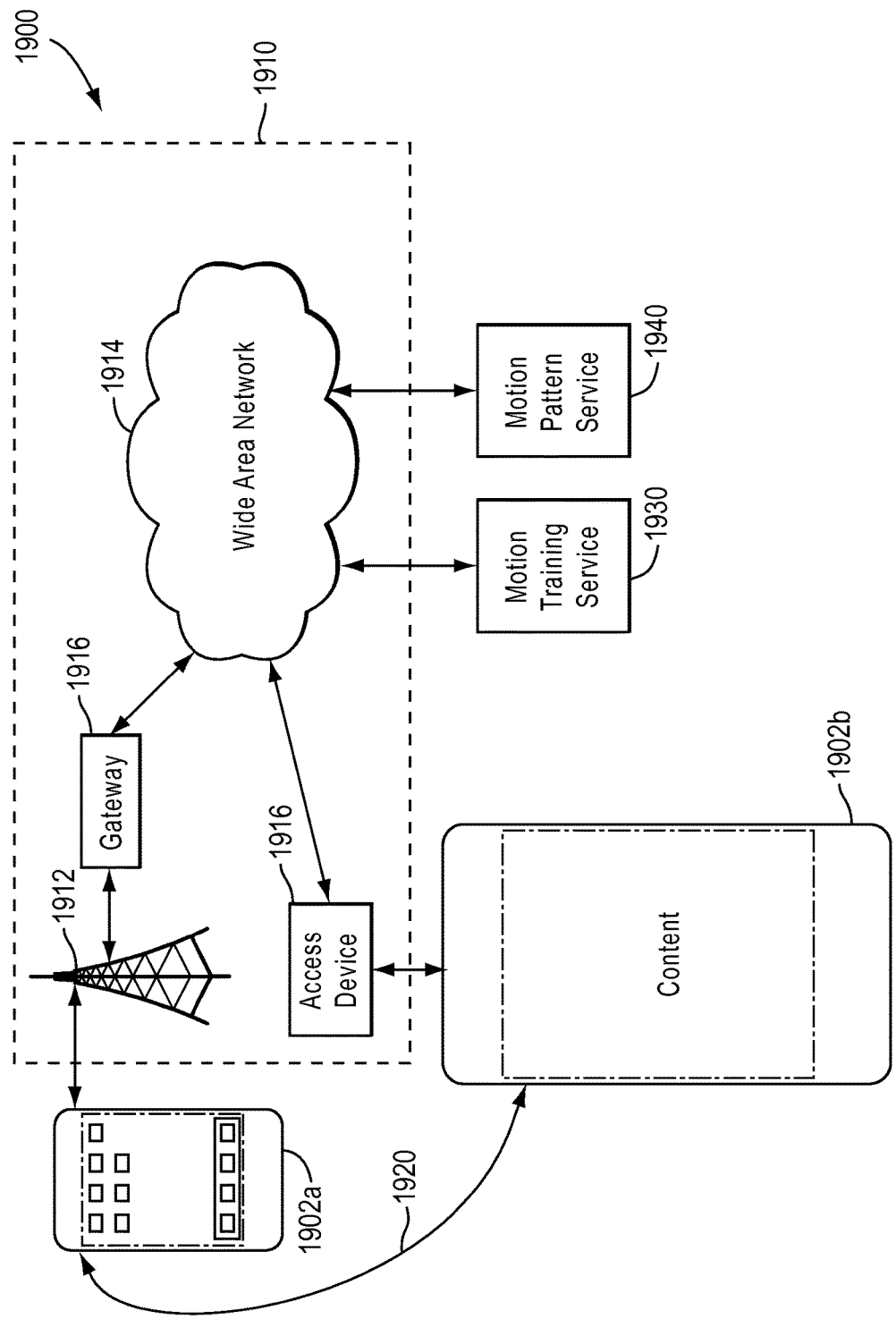
FIG. 24 is a block diagram of exemplary network operating environment for the monitoring systems implementing motion pattern classification and gesture creation and recognition techniques.

FIG. 24 is a block diagram of exemplary network operating environment 1900 for the motion/movement/gesture detection devices implementing motion pattern classification and gesture recognition techniques. Mobile devices 1902(*a*) and 1902(*b*) can, for example, communicate over one or more wired and/or wireless networks 1910 in data communication. For example, a wireless network 1912, e.g., a cellular network, can communicate with a wide area network (WAN) 1914, such as the Internet, by use of a gateway 1916. Likewise, an access device 1918, such as an 802.11g wireless access device, can provide communication access to the wide area network 1914.

In some implementations, both voice and data communications can be established over wireless network 1912 and the access device 1918. For example, motion/movement/gesture detection device 1902(*a*) can place and receive phone calls (e.g., using voice over Internet Protocol (VoIP) protocols), send and receive e-mail messages (e.g., using Post Office Protocol 3 (POP3)), and retrieve electronic documents and/or streams, such as web pages, photographs, and videos, over wireless network 1912, gateway 1916, and wide area network 1914 (e.g., using Transmission Control Protocol/Internet Protocol (TCP/IP) or User Datagram Protocol (UDP)). Likewise, in some implementations, the motion/movement/gesture detection device 1902(*b*) can place and receive phone calls, send and receive e-mail messages, and retrieve electronic documents over the access device 1918 and the wide area network 1914. In some implementations, motion/movement/gesture detection device 1902(*a*) or 1902(*b*) can be physically connected to the access device 1918 using one or more cables and the access device 1918 can be a personal computer. In this configuration, motion/movement/gesture detection device 1902(*a*) or 1902(*b*) can be referred to as a "tethered" device.

Mobile devices 1902(*a*) and 1902(*b*) can also establish communications by other means. For example, wireless motion/movement/gesture detection device 1902(*a*) can communicate with other wireless devices, e.g., other motion/movement/gesture detection device s 1902(*a*) or 1902(*b*), cell phones, etc., over the wireless network 1912. Likewise, motion/movement/gesture detection device s 1902(*a*) and 1902(*b*) can establish peer-to-peer communications 1920, e.g., a personal area network, by use of one or more communication subsystems, such as the Bluetooth™ communication devices. Other communication protocols and topologies can also be implemented.

The motion/movement/gesture detection device 1902(*a*) or 1902(*b*) can, for example, communicate with one or more services 1930 and 1940 over the one or more wired and/or wireless networks. For example, one or more motion training services 1930 can be used to determine one or more motion patterns. Motion pattern service 1940 can provide the one or more one or more motion patterns to motion/movement/gesture detection device s 1902(*a*) and 1902(*b*) for recognizing gestures.

Mobile device 1902 (*a*) or 1902 (*b*) can also access other data and content over the one or more wired and/or wireless networks. For example, content publishers, such as news sites, Rally Simple Syndication (RSS) feeds, web sites, blogs, social networking sites, developer networks, etc., can be accessed by motion/movement/gesture detection device 1902(*a*) or 1902(*b*). Such access can be provided by invocation of a web browsing function or application (e.g., a browser) in response to a user touching, for example, a Web object.

Exemplary System Architecture

Figure 25:
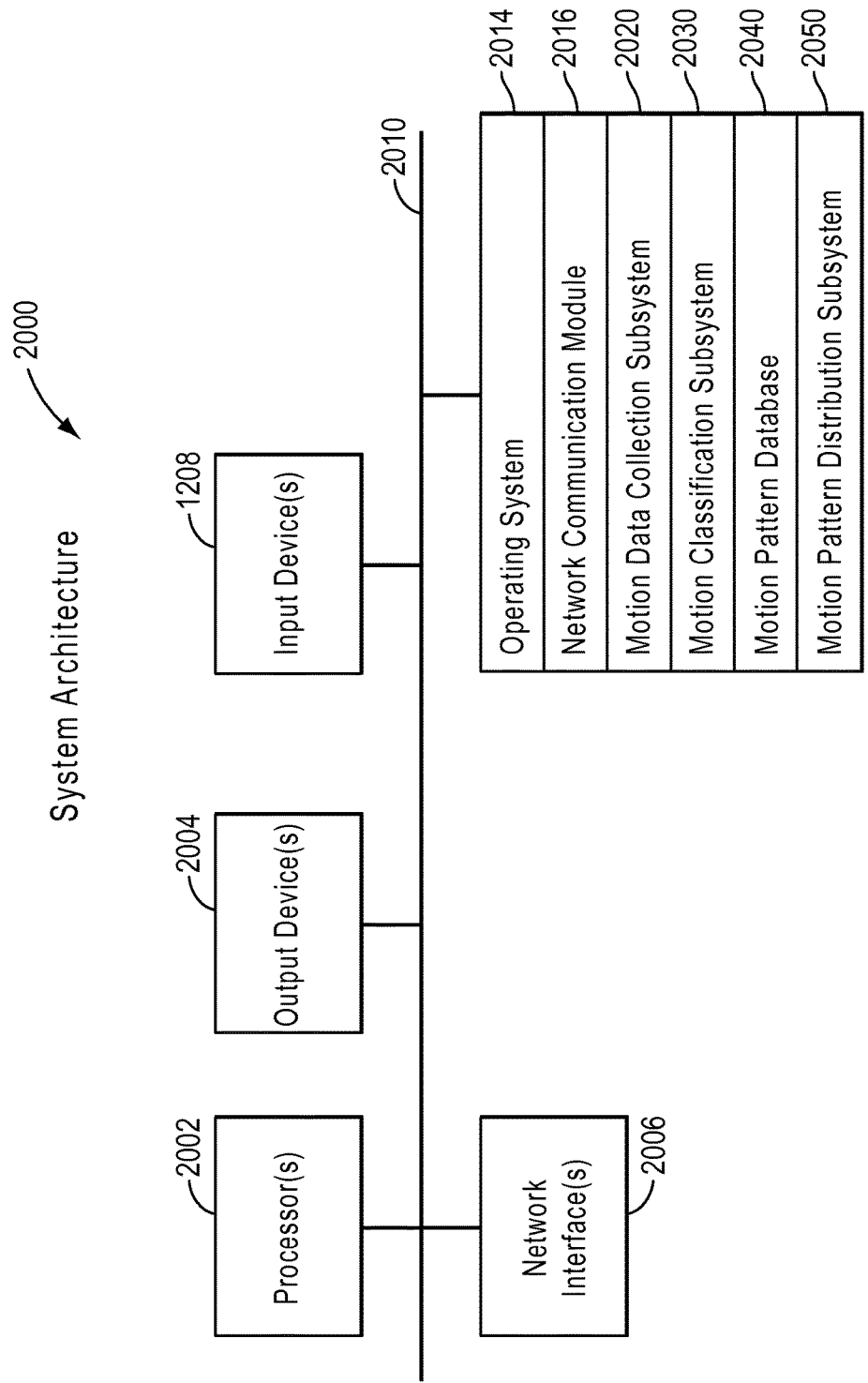
FIG. 25 is a block diagram of exemplary system architecture for implementing the features and operations of motion pattern classification and gesture creation and recognition.

FIG. 25 is a block diagram of exemplary system architecture for implementing the features and operations of motion pattern classification and gesture recognition. Other architectures are possible, including architectures with more or fewer components. In some implementations, architecture 2000 includes one or more processors 2002 (e.g., dual-core Intel® Xeon® Processors), one or more output devices 2004 (e.g., LCD), one or more network interfaces 2006, one or more input devices 2008 (e.g., mouse, keyboard, touch-sensitive display) and one or more computer-readable media 2012 (e.g., RAM, ROM, SDRAM, hard disk, optical disk, flash memory, etc.). These components can exchange communications and data over one or more communication channels 2010 (e.g., buses), which can utilize various hardware and software for facilitating the transfer of data and control signals between components.

The term "computer-readable medium" refers to any medium that participates in providing instructions to processor 2002 for execution, including without limitation, non-volatile media (e.g., optical or magnetic disks), volatile media (e.g., memory) and transmission media. Transmission media includes, without limitation, coaxial cables, copper wire and fiber optics.

Computer-readable medium 2012 can further include operating system 2014 (e.g., Mac OS® server, Windows® NT server), network communications module 2016, motion data collection subsystem 2020, motion classification subsystem 2030, motion pattern database 2040, and motion pattern distribution subsystem 2050. Motion data collection subsystem 2020 can be configured to receive motion samples from motion/movement/gesture detection device s. Motion classification subsystem 2030 can be configured to determine one or more motion patterns from the received motion samples. Motion pattern database 2040 can store the motion patterns. Motion pattern distribution subsystem 2050 can be configured to distribute the motion patterns to motion/movement/gesture detection device s. Operating system 2014 can be multi-user, multiprocessing, multitasking, multithreading, real time, etc. Operating system 2014 performs basic tasks, including but not limited to: recognizing input from and providing output to devices 2006, 2008; keeping track and managing files and directories on computer-readable media 2012 (e.g., memory or a storage device); controlling peripheral devices; and managing traffic on the one or more communication channels 2010. Network communications module 2016 includes various components for establishing and maintaining network connections (e.g., software for implementing communication protocols, such as TCP/IP, HTTP, etc.). Computer-readable medium 2012 can further include a database interface. The database interface can include interfaces to one or more databases on a file system. The databases can be organized under a hierarchical folder structure, the folders mapping to directories in the file system.

Architecture 2000 can be included in any device capable of hosting a database application program. Architecture 2000 can be implemented in a parallel processing or peer-to-peer infrastructure or on a single device with one or more processors. Software can include multiple software components or can be a single body of code.

The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language (e.g., Objective-C, Java), including compiled or interpreted languages, and it can be deployed in any form, including as a stand-alone program or as a module, component, subroutine, a browser-based web application, or other unit suitable for use in a computing environment.

Suitable processors for the execution of a program of instructions include, by way of example, both general and special purpose microprocessors, and the sole processor or one of multiple processors or cores, of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semi-conductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, and the computers and networks forming the Internet.

The computer system can include clients and servers. A client and server are generally remote from each other and typically interact through a network. The relationship of client and server arises by virtue of computer programs running on the respective computers and having a client-server relationship to each other.

Light Proximity

Figure 26:
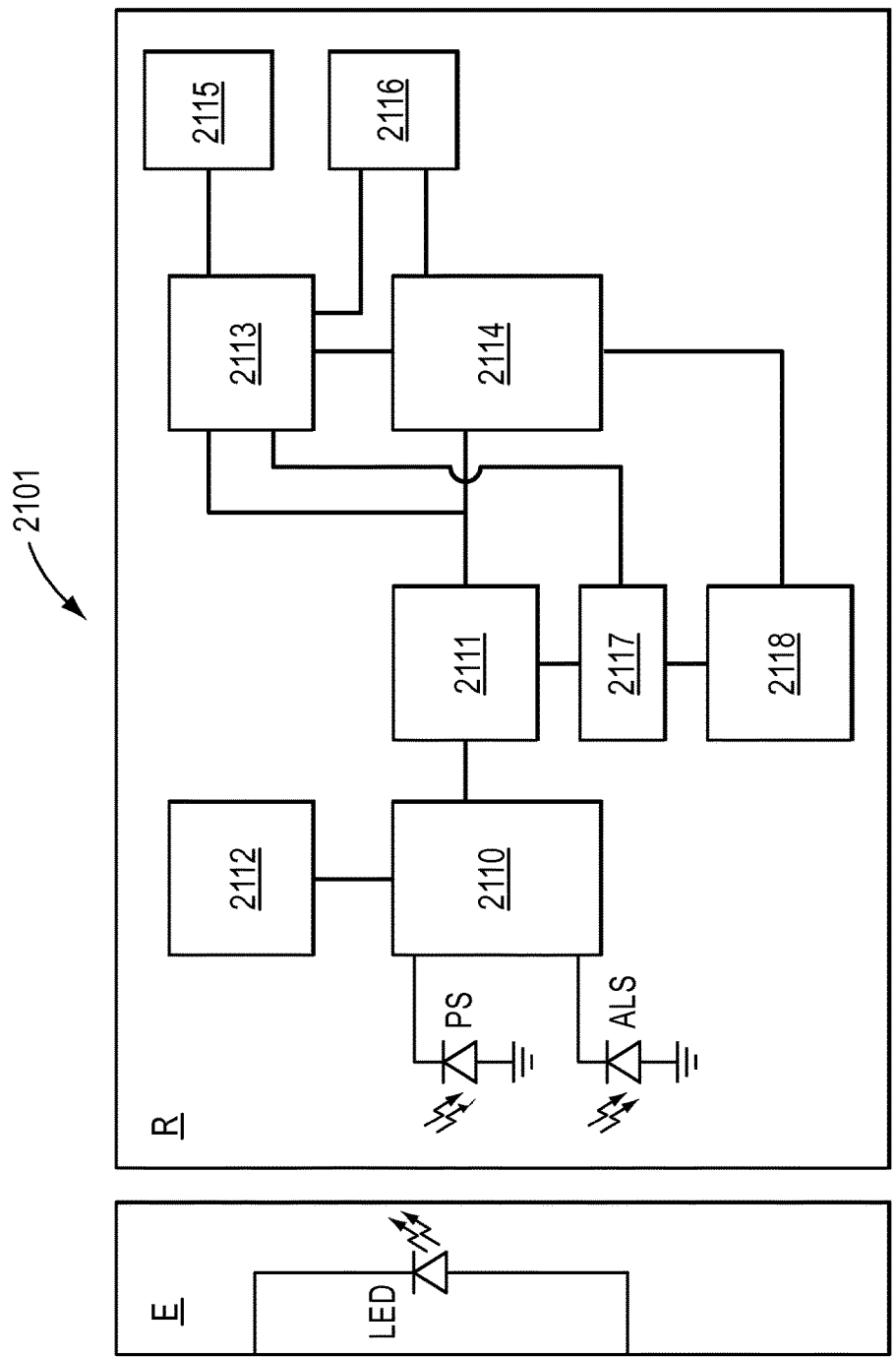
FIG. 26 illustrates a functional block diagram of a proximity sensor in an embodiment of the invention.

FIG. 26 illustrates a functional block diagram of a proximity sensor in one embodiment. As shown in FIG. 26, the proximity sensor 2101 includes a light emitter E and a light sensor R. The light emitter E includes a light-emitting diode LED used to emit lights. In one embodiment the light-emitting diode LED can be an infrared ray light-emitting diode (IR LED) used to emit infrared rays, but is not limited to this.

In one embodiment, the light sensor R can be an integrated circuit including at least one light sensing unit and a control circuit. In FIG. 26, the light sensor R includes a proximity sensing unit PS, an ambient light sensing unit ALS, a sensed light processing unit 2110, an analog/digital converter 2111, a temperature compensating unit 2112, a digital signal processing unit 2113, an inter-integrated circuit (I2C) interface 2114, a buffer 2115, a LED driver 2116, an oscillator 2117, and a reference value generator 2118. The proximity sensing unit PS and the ambient light sensing unit ALS are coupled to the sensed light processing unit 2110; the temperature compensating unit 2112 is coupled to the sensed light processing unit 2110; the analog/digital converter 2111 is coupled to the sensed light processing unit 2110, the digital signal processing unit 2113, the I2C interface 2114, and the oscillator 2117 respectively; the digital signal processing unit 2113 is coupled to the analog/digital converter 2111, the I2C interface 2114, the buffer 2115, the LED driver 2116, and the oscillator 2117 respectively; the I2C interface 2114 is coupled to the analog/digital converter 2111, the digital signal processing unit 2113, the LED driver 2116, and the reference value generator 2118 respectively; the oscillator 2117 is coupled to the analog/digital converter 2111, the digital signal processing unit 2113, and the reference value generator 2118 respectively; the reference value generator 2118 is coupled to the I2C interface 2114 and the oscillator 2117 respectively.

In this embodiment, the ambient light sensing unit ALS is used to sense an ambient light intensity around the proximity sensor 2111. The sensed light processing unit 2110 is used to process the light signal sensed by the ambient light sensing unit ALS and the proximity sensing unit PS and to perform temperature compensation according to the temperature compensating unit 2112. The LED driver 2116 is used to drive the light-emitting diode LED. The oscillator 2117 can be a quartz oscillator. The reference value generator 2118 is used to generate a default reference value.

The user can use the I2C interface 2114 to set digital signal processing parameters needed by the digital signal processing unit 2113. When the object is close to the light sensor R, the lights emitted from the light-emitting diode LED will be reflected to the proximity sensing unit PS by the object, and then the reflected lights will be processed by the sensed light processing unit 2110 and converted into digital light sensing signals by the analog/digital converter 2111. Then, the digital signal processing unit 2113 will determine whether the object is close to the light sensor R according to the digital light sensing signal.

If the result determined by the digital signal processing unit 2113 is yes, the buffer 2115 will output a proximity notification signal to inform the electronic apparatus including the proximity sensor 2111 that the object is close to the electronic apparatus, so that the electronic apparatus can immediately make corresponding action. For example, a smart phone with the proximity sensor 2111 will know that the face of the user is close to the smart phone according to the proximity notification signal; therefore, the smart phone will shut down the touch function of the touch monitor to avoid the touch monitor being carelessly touched by the face of the user.

However, the proximity sensor 2111 may have noise crosstalk problem due to poor packaging or mechanical design, which may cause the digital signal processing unit 2113 to make a misjudgment, and in turn causing the electronic apparatus, including the proximity sensor 2111, to malfunction. For example, if when the face of the user is not close to the smart phone, but the digital signal processing unit 2113 makes a misjudgment that an object is close to the smart phone, the smart phone will shut down the touch function of the touch monitor, and the user will not be able to user the touch function of the touch monitor. Therefore, the proximity sensor 2111 of this embodiment has three operation modes described as follows to solve the aforementioned malfunction problem.

Figure 27A:
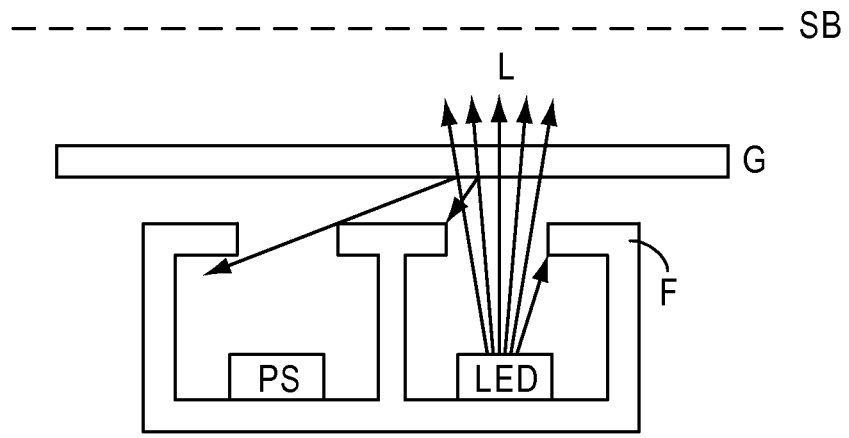
FIG. 27(a) illustrates a schematic diagram of the proximity sensing unit sensing when the LED is active and emits lights under the condition that no object is close by to the proximity sensor of the electronic apparatus.
Figure 27B:
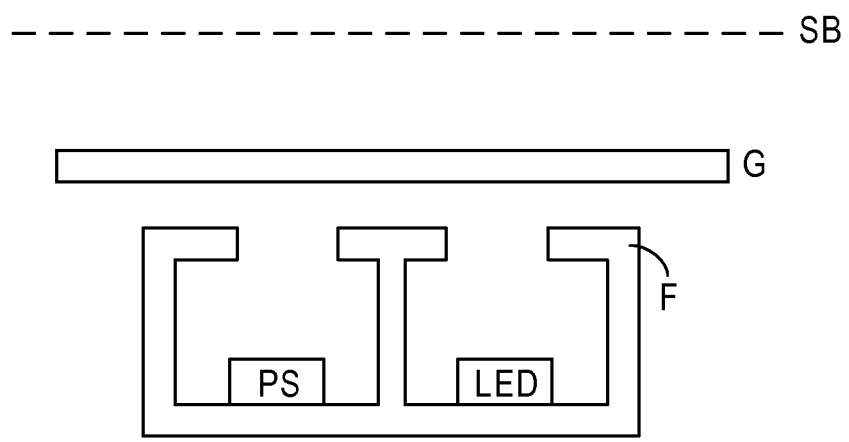
FIG. 27(b) illustrates a schematic diagram of the proximity sensing unit sensing when the LED is inactive under the condition that no object is close by to the proximity sensor of the electronic apparatus.

The first operation mode is a manual setting mode. After the electronic apparatus, including the proximity sensor 2111, is assembled as shown in FIGS. 27(a) and (b) under the condition that no object is close to the proximity sensor 2111 of the electronic apparatus, if the proximity sensing unit PS senses a first measured value C1 when the light-emitting diode LED is active and emits the light L (see FIG. 27(a) and senses a second measured value C2 when the light-emitting diode LED is inactive (see FIG. 27(b), since the second measured value C2 may include noise and the first measured value C1 may include noise and noise cross-talk (e.g., the portion reflected by the glass G), the digital signal processing unit 2113 can subtract the second measured value C2 from the first measured value C1 to obtain an initial noise cross-talk value CT under the condition that no object is close to the proximity sensor 2111 of the electronic apparatus, and store the initial noise cross-talk value CT in a register (not shown in the figure) through the I2C interface 2114. The initial noise cross-talk value CT can be used as a maximum threshold value of noise cross-talk in the system.

It should be noticed that since no object is close to the proximity sensor 2111 of the electronic apparatus at this time, the initial noise cross-talk value CT obtained by the digital signal processing unit 2113 should only include noise cross-talk values caused by the packaging and the mechanical portion of the system. Therefore, after the initial noise cross-talk value CT is obtained, whenever the proximity sensor 2111 tries to detect whether the object is close to the proximity sensor 2111, the digital signal processing unit 2113 needs to subtract the initial noise cross-talk value CT from the measured value to effectively reduce the effect of noise cross-talk.

The second operation mode is an automatic setting mode. Whenever the electronic apparatus, including the proximity sensor 2111, is active, the proximity sensor 2111 can obtain the initial noise cross-talk value CT by subtracting the second measured value C2 from the first measured value C1 as mentioned above, and the initial noise cross-talk value CT can be used as a standard to determine that the sensed value is noise, noise cross-talk, or light signal reflected by the object.

As shown in FIG. 27(c) through FIG. 27(f), after the electronic apparatus including the proximity sensor 2111 is active, the object 2 may be close to the proximity sensor 2111 of the electronic apparatus, and the object 2 may be located in the detection range of the proximity sensor 2111. If the proximity sensing unit PS senses a third measured value C3 when the light-emitting diode LED is active and emits the light L and senses a fourth measured value C4 when the light-emitting diode LED is inactive. Since the fourth measured value C4 may include the noise, and the third measured value C3 may include the noise, the noise cross-talk, and the light signal reflected by the object 2, the digital signal processing unit 2113 can obtain a specific measured value M by subtracting the fourth measured value C4 from the third measured value C3, and the specific measured value M represents the noise cross-talk and the light signal reflected by the object 2.

Next, the digital signal processing unit 2113 determines whether the specific measured value M is larger than the initial noise cross-talk value CT. If the result determined by the digital signal processing unit 2113 is no, it means that the specific measured value M (the noise cross-talk and the light signal reflected by the object 2) at this time is smaller than the initial noise cross-talk value CT. Therefore, the proximity sensor 2111 needs to replace the initial noise cross-talk value CT stored in the register with the specific measured value M through the I2C interface 2114. Afterwards, when the proximity sensor 2111 detects whether any object is close to the proximity sensor 2111 again, the updated initial noise cross-talk value (the specific measured value M) will be used as a standard of determination.

If the result determined by the digital signal processing unit 2113 is yes, it means that the specific measured value M (the noise cross-talk and the light signal reflected by the object 2) at this time is larger than the initial noise cross-talk value CT. Therefore, it is unnecessary to update the initial noise cross-talk value CT stored in the register. Then, the digital signal processing unit 2113 will subtract the initial noise cross-talk value CT from the specific measured value M to obtain the reflection light signal value N of the object 2.

Afterwards, in order to determine whether the object 2 is located in the detection range of the proximity sensor 2111, that is to say, to determine whether the object 2 is close enough to the proximity sensor 2111, the digital signal processing unit 2113 compares the reflection light signal value N of the object 2 with a default value NO to determine whether the reflection light signal value N of the object 2 is larger than the default value NO. It should be noted that the default value NO is the object detecting threshold value detected by the proximity sensor 2111 when the object 2 is located at the boundary SB of the detection range of the proximity sensor 2111.

Figure 27C:
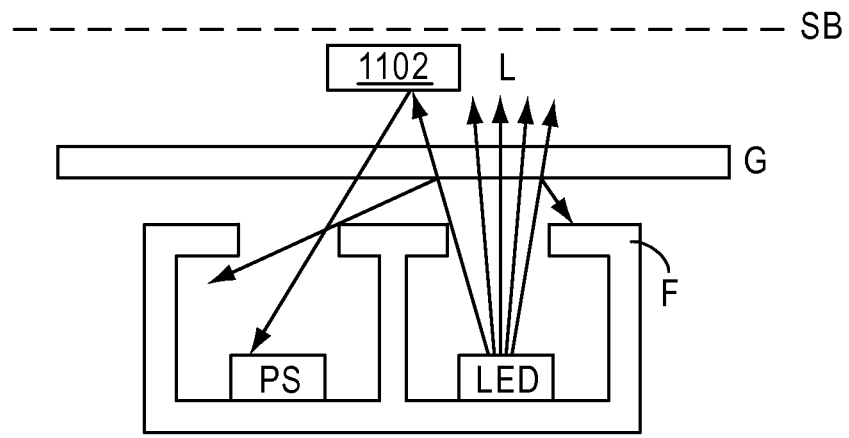
FIG. 27(c) illustrates a schematic diagram of the proximity sensing unit sensing when the LED is active and emits lights under the condition that an object is located in the detection range of the proximity sensor.
Figure 27D:
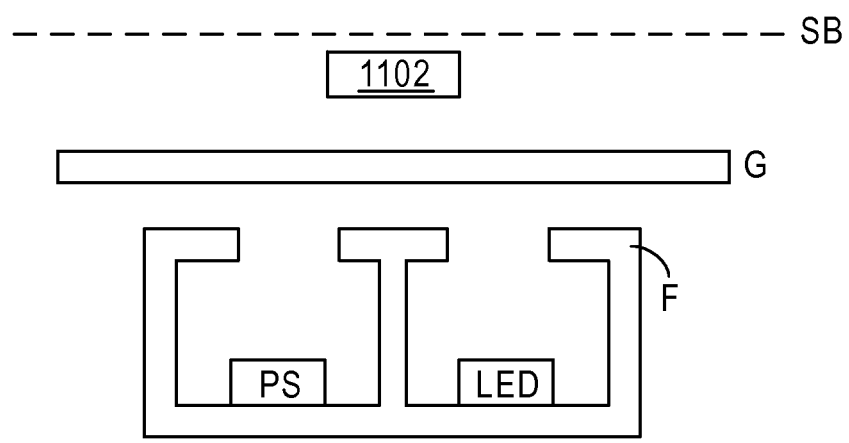
FIG. 27(d) illustrates a schematic diagram of the proximity sensing unit sensing when the LED is inactive under the condition that an object is located in the detection range of the proximity sensor.

If the result determined by the digital signal processing unit 2113 is yes, that is to say, the reflection light signal value N of the object 2 is larger than the default value NO, it means that the strength of the light reflected by the object 2, reflecting the light of the light-emitting diode LED, is stronger than the strength of the light reflected by the object located at the boundary SB of the detection range of the proximity sensor 2111, also reflecting the light of the light-emitting diode LED. Therefore, the proximity sensor 2111 knows that the object 2 is located in the detection range of the proximity sensor 2111; that is say; the object 2 is close enough to the proximity sensor 2111, as shown in FIG. 27(c) and FIG. 27(d). At this time, the buffer 2115 will output a proximity notification signal to inform the electronic apparatus, including the proximity sensor 2111, that the object 2 is approaching, so that the electronic apparatus can immediately make corresponding actions. For example, the electronic apparatus can shut down the touch function of its touch monitor.

Figure 27E:
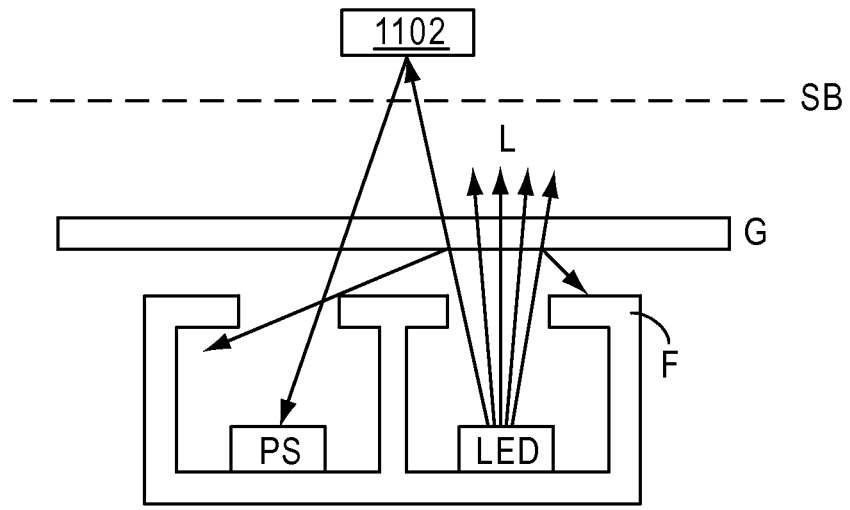
FIG. 27(e) illustrates a schematic diagram of the proximity sensing unit sensing when the LED is active and emits lights under the condition that an object is located out of the detection range of the proximity sensor.
Figure 27F:
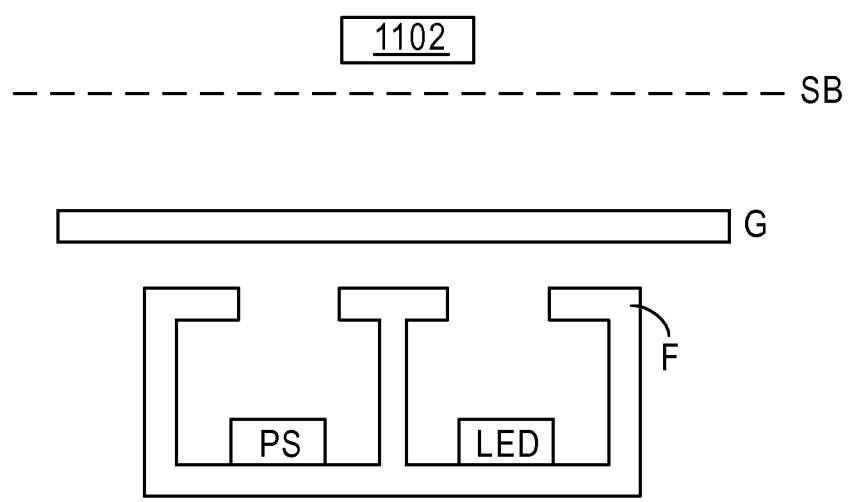
FIG. 27(f) illustrates a schematic diagram of the proximity sensing unit sensing when the LED is inactive under the condition that an object is located out of the detection range of the proximity sensor.

If the result determined by the digital signal processing unit 2113 is no, that is to say, the reflection light signal value N of the object 2 is not larger than the default value NO, it means that the strength of the light reflected by the object 2, reflecting the light of the light-emitting diode LED, is not stronger than the strength of the light reflected by the object located at the boundary SB of the detection range of the proximity sensor 2111, reflecting the light of the light-emitting diode LED. Therefore, the proximity sensor 2111 knows that the object 2 is not located in the detection range of the proximity sensor 2111; that is to say, the object 2 is not close enough to the proximity sensor 2111, as shown in FIGS. 27(e) and 27(f). Therefore, the buffer 2115 will not output the proximity notification signal to inform the electronic apparatus, including the proximity sensor 2111, that the object 2 is approaching, and the electronic apparatus will not make corresponding actions such as shutting down the touch function of its touch monitor.

The third operation mode is a selection setting mode. The user can use the I2C interface 2114 to set a control bit for the user to freely choose between the manual setting mode and the automatic setting mode to reduce the effect of the noise crosstalk.

Figure 28:
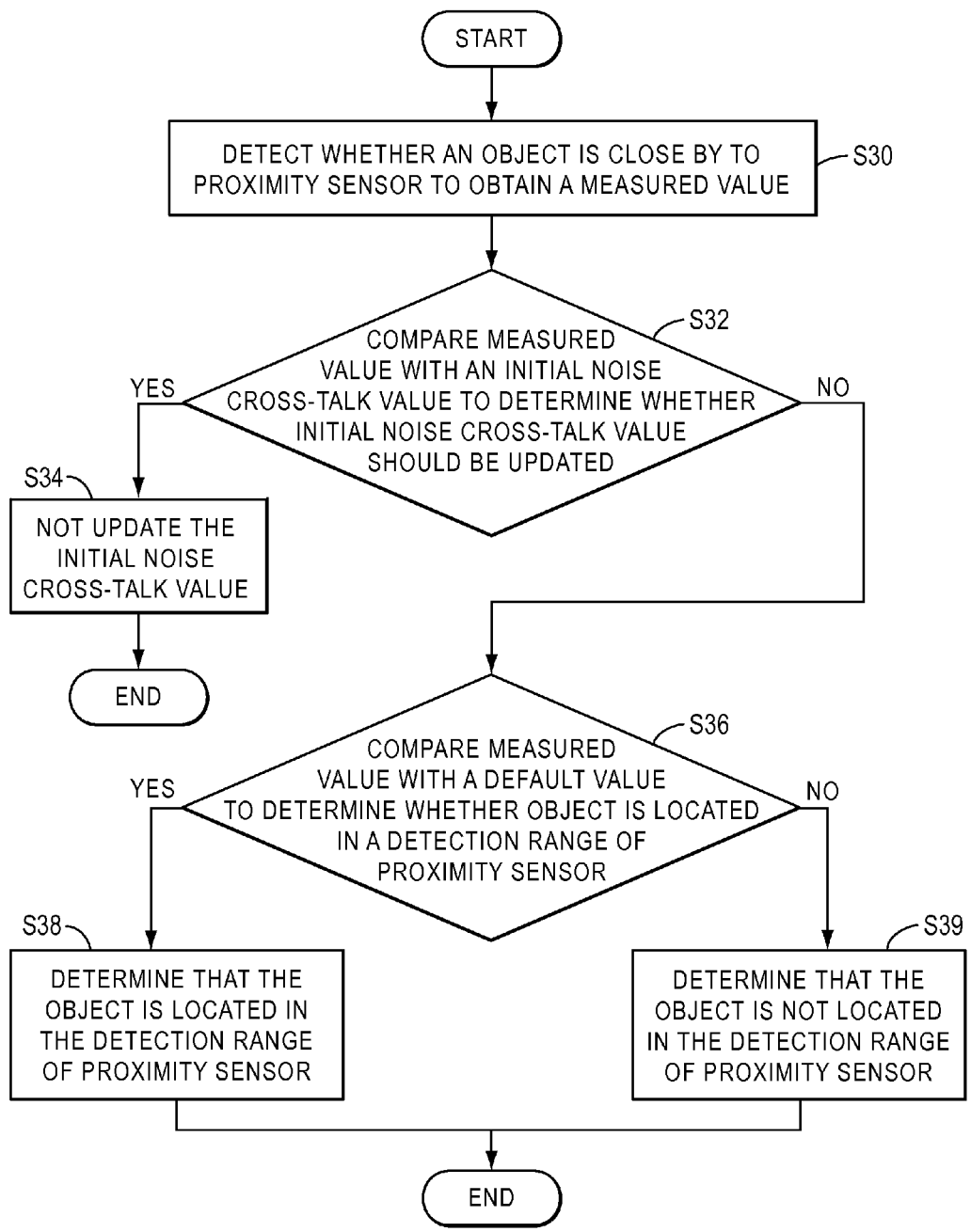
FIG. 28 illustrates a flowchart of the proximity sensor operating method in another embodiment of the invention.

Another preferred embodiment of the invention is a proximity sensor operating method. FIG. 28 illustrates a flowchart of the proximity sensor operating method in this embodiment.

As shown in FIG. 28, in the step S30, the method detects whether an object is close by to the proximity sensor to obtain a measured value. Then, in the step S32, the method compares the measured value with an initial noise cross-talk value to determine whether the initial noise cross-talk value should be updated. Wherein, the initial noise cross-talk value is obtained by the proximity sensor operated under the manual setting mode. Under the manual setting mode, the proximity sensor obtains a first measured value when the light emitter is active and a second measured value when the light emitter is inactive, and subtracts the second measured value from the first measured value to obtain an initial noise cross-talk value.

If the result determined by the step S32 is yes, the method will perform the step S34, not to update the initial noise cross-talk value. If the result determined by the step S32 is no, the method will perform the step S36 to compare the measured value with a default value to determine whether the object is located in a detection range of the proximity sensor. Wherein, the default value is the object detecting threshold value detected by the proximity sensor when the object is located at the boundary of the detection range of the proximity sensor.

If the result determined by the step S36 is yes, the method will perform the step S38 to determine that the object is located in the detection range of the proximity sensor. If the result determined by the step S36 is no, the method will perform the step S39 to determine that the object is not located in the detection range of the proximity sensor.

Figure 29A:
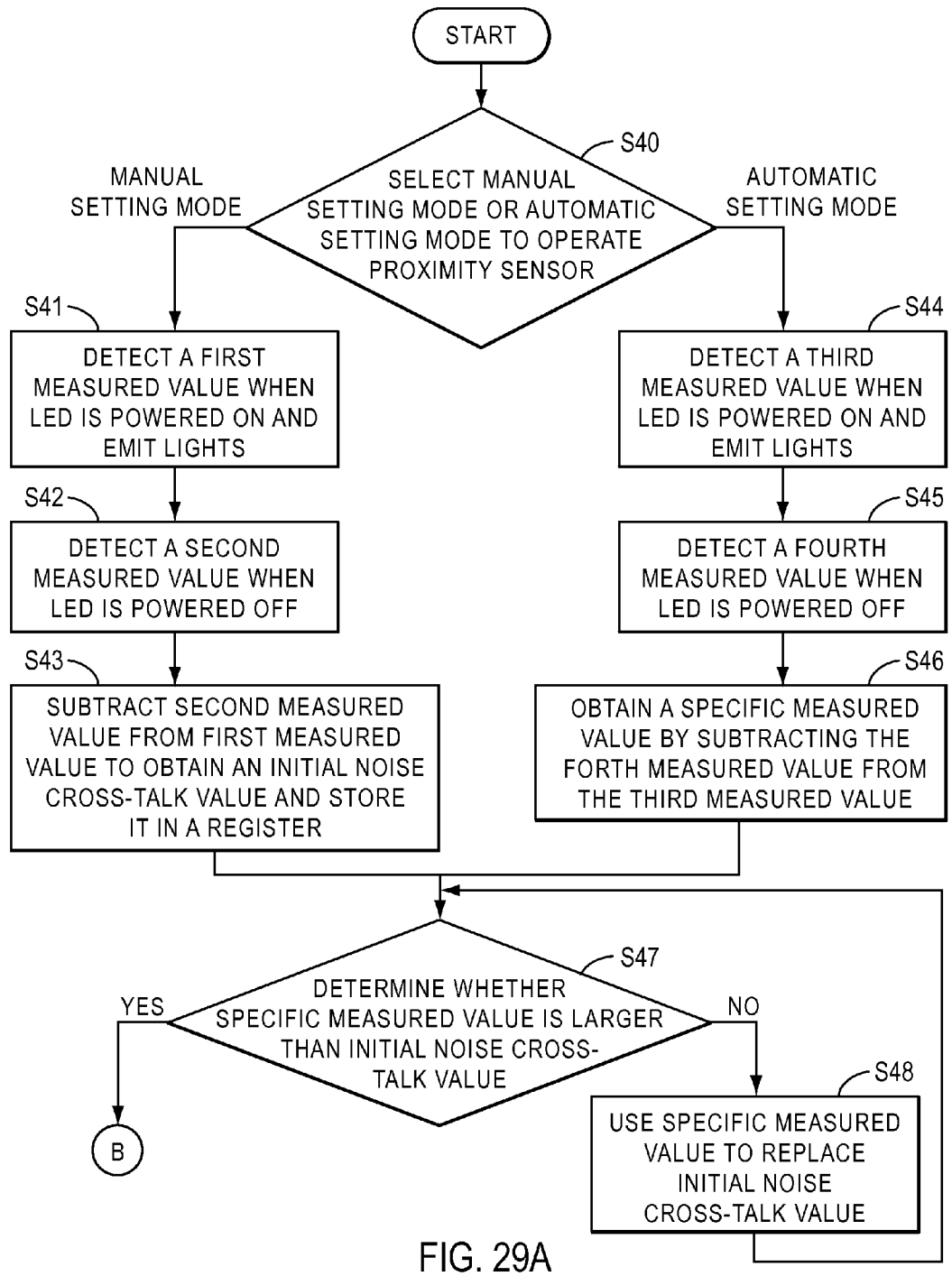
FIGS. 29(a) and (b) illustrate flowcharts of the proximity sensor operating method in another embodiment of the invention.
Figure 29B:
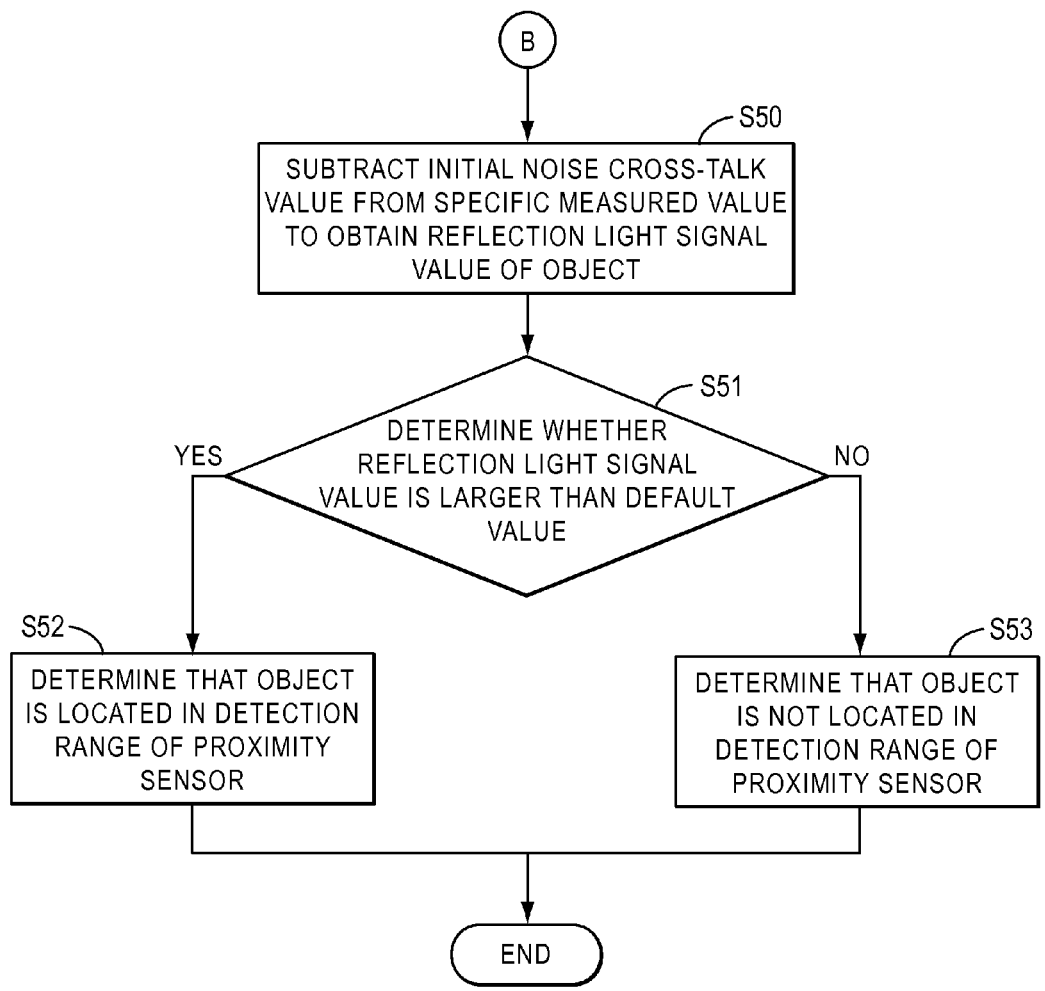

FIGS. 29(a) and (b) illustrate flowcharts of the proximity sensor operating method in another embodiment. As shown in FIGS. 29(a) and (b), in the step S40, the method selects either the manual setting mode or the automatic setting mode to operate the proximity sensor. If the manual setting mode is selected, under the condition that no object is close by to the proximity sensor of the electronic apparatus, the method performs the step S41 to detect a first measured value C1 when the LED is active and emit lights and the step S42 to detect a second measured value C2 when the LED is inactive.

Since the second measured value C2 may include noise and the first measured value C1 may include noise and noise cross-talk, in the step S43, the method subtracts the second measured value C2 from the first measured value C1 to obtain an initial noise cross-talk value CT and store the initial noise cross-talk value CT in a register, and the initial noise cross-talk value CT is used as a maximum threshold value of noise cross-talk in the system.

If the automatic setting mode is used, after the electronic apparatus, including the proximity sensor, is active, the object may be close to the proximity sensor of the electronic apparatus. The method performs the step S44 to detect a third measured value C3 when the LED is active and emit lights and the step S45 to detect a fourth measured value C4 when the LED is inactive. Since the fourth measured value C4 may include the noise, and the third measured value C3 may include the noise, the noise cross-talk, and the light signal reflected by the object. Therefore, in the step S46, the method obtains a specific measured value M by subtracting the fourth measured value C4 from the third measured value C3, and the specific measured value M represents the noise cross-talk and the light signal reflected by the object.

In step S47 the method determines whether the specific measured value M is larger than the initial noise cross-talk value CT. If the result determined by the step S47 is no, it means that the specific measured value M (the noise cross-talk and the light signal reflected by the object 2) at this time is smaller than the initial noise cross-talk value CT. Therefore, in the step S48, the method uses the specific measured value M to replace the initial noise cross-talk value CT; so that the specific measured value M can be used as an updated initial noise cross-talk value. Later, when the method performs the step S47 again, the updated initial noise cross-talk value (the specific measured value M) will be used to compare with another specific measured value M' obtained by the method performing the step S46 again to determine whether the specific measured value M' is larger than the updated initial noise cross-talk value (the specific measured value M).

If the result determined by the step S47 is yes, it means that the specific measured value M (the noise cross-talk and the light signal reflected by the object) at this time is larger than the initial noise cross-talk value CT. Therefore, it is unnecessary to update the initial noise cross-talk value CT stored in the register. In the step S50, the method will subtract the initial noise cross-talk value CT from the specific measured value M to obtain the reflection light signal value N of the object.

Afterwards, in order to determine whether the object is located in the detection range of the proximity sensor; that is to say, to determine whether the object is close enough to the proximity sensor, in the step S51, the method will compare the reflection light signal value N of the object with a default value NO to determine whether the reflection light signal value N of the object is larger than the default value NO. It should be noted that the default value NO is the object detecting threshold value detected by the proximity sensor when the object is located at the boundary of the detection range of the proximity sensor.

If the result determined by the step S51 is yes, that is to say, the reflection light signal value N of the object is larger than the default value NO, it means that the strength of the reflected light generated by the object reflecting the light of the LED is stronger than the strength of the reflected light generated by the strength of the reflected light generated by the object located at the boundary of the detection range of the proximity sensor reflecting the light of the LED. Therefore, in the step S52, the method determines that the object is located in the detection range of the proximity sensor; that is say, the object is close enough to the proximity sensor. At this time, the proximity sensor will output a proximity notification signal to inform the electronic apparatus that the object is approaching, so that the electronic apparatus can immediately make corresponding action.

If the result determined by the step S51 is no, that is to say, the reflection light signal value N of the object is not larger than the default value NO, it means that the strength of the light reflected by the object, reflecting the light of the LED, is not stronger than the strength of the light reflected by the object located at the boundary of the detection range of the proximity sensor, also reflecting the light of the LED. Therefore, in the step S53, the method determines that the object is not located in the detection range of the proximity sensor; that is to say, the object is not close enough to the proximity sensor. Therefore, the buffer will not output the proximity notification signal to inform the electronic apparatus that the object is approaching.

Particle Detection

Figure 30:
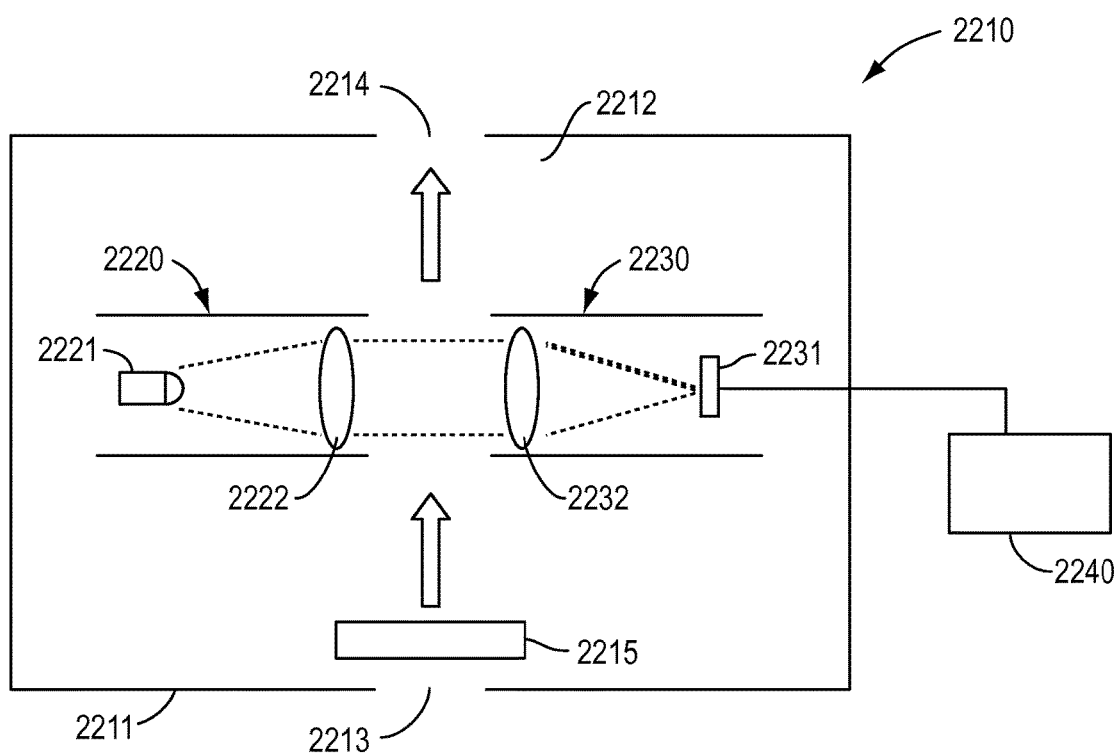
FIG. 30 is a schematic view showing a configuration of a particle detection apparatus of a first embodiment according to the present invention.

FIG. 30 is a schematic view showing a configuration of a particle detector according in one embodiment. An apparatus 2210 has a chamber 2212 surrounded by a wall 2211, and the chamber 2212 has an inlet 2213 for taking air from the outside and an outlet 2214 for discharging air. In order to take air and generate airflow at a particle detection position as later described, an airflow generating/controlling device 2215 is provided on the inner side of the inlet 2213. Even when the airflow generating/controlling device 2215 is not turned on, air can flow between the inlet 2213 and outlet 2214.

As the airflow generating/controlling device 2215, a small fan is typically used. However, in order to generate airflow in a rising direction opposite to the gravity, an air heating device such as a heater may be used. Air entered from the inlet 2213 into the chamber 2212 passes through the inside of the chamber 2212 and is guided to the outlet 2214. Though not shown, airflow guide means having, for example, a cylindrical shape may be provided between the inlet 2213 and the outlet 2214. Further, a filter may be installed at a prior stage to the airflow generating/controlling device 2215 to prevent the entry of particles having a size greater than target fine particles.

The apparatus 2210 also includes means for detecting a particle. That means includes a light source 2220 and a detection device 2230. In this embodiment, the light source 2220 and the detection device 2230 are arranged horizontally in an opposing manner. This allows the detection device 2230 to directly receive light from the light source 2220, and the light source 2220 and the detection device 2230 are configured to pass the airflow generated by the airflow generating/controlling device 2215 between them.

The light source 2220 is composed of a light-emitting element 2221 and an optical system 2222 including a lens. The light-emitting element 2221 may be typically composed of a semiconductor light-emitting element such as a laser diode or a light-emitting diode capable of emitting coherent light. If the degree of sensitivity is not pursued, other light-emitting element may be used. However, a light-emitting element capable of emitting light with a certain degree of directional characteristics is desired from the viewpoint of device design.

On the other hand, the detection device 2230 is composed of a photodetector 2231 and an optical system 2232 including a lens. As the photodetector 2231, an image sensor such as a CMOS image sensor or a CCD image sensor may be used. The photodetector 2231 is configured so as to output a detection signal to an external analyzer 2240.

Light emitted from the light emitting-element 2221 passes through the optical system 2222, and is illuminated to a gas to be measured. In one embodiment, light emitted from the light emitting-element 21 is substantially collimated by the optical system 2222. The light passing through the gas in the measurement area is collected by the optical system 2232 in the detection device 2230, and detected as an image by an image sensor 31. The image sensor 31 outputs a signal of the image to the analyzer 2240.

Optical dimensions of the lens in the optical system 2222, such as a focal length, can be determined based on a radiation angle of light from the light-emitting element 2221 and a diameter of fine particles to be measured. Specifically, it is necessary to select a focal length of the lens so that a light flux has a diameter several times larger than the size of the fine particles to be measured. For example, in measuring fine particles having a size of approximately 100 micrometers, it is necessary to illuminate light in such a way that the light has a diameter of not less than several hundred micrometers, so as to keep the sensitivity of the entire system. However, if light is illuminated to a large area, the power of transmitted light to be detected decreases, resulting in a degraded signal/noise ratio. Therefore, optimization may be necessary.

Figure 31:
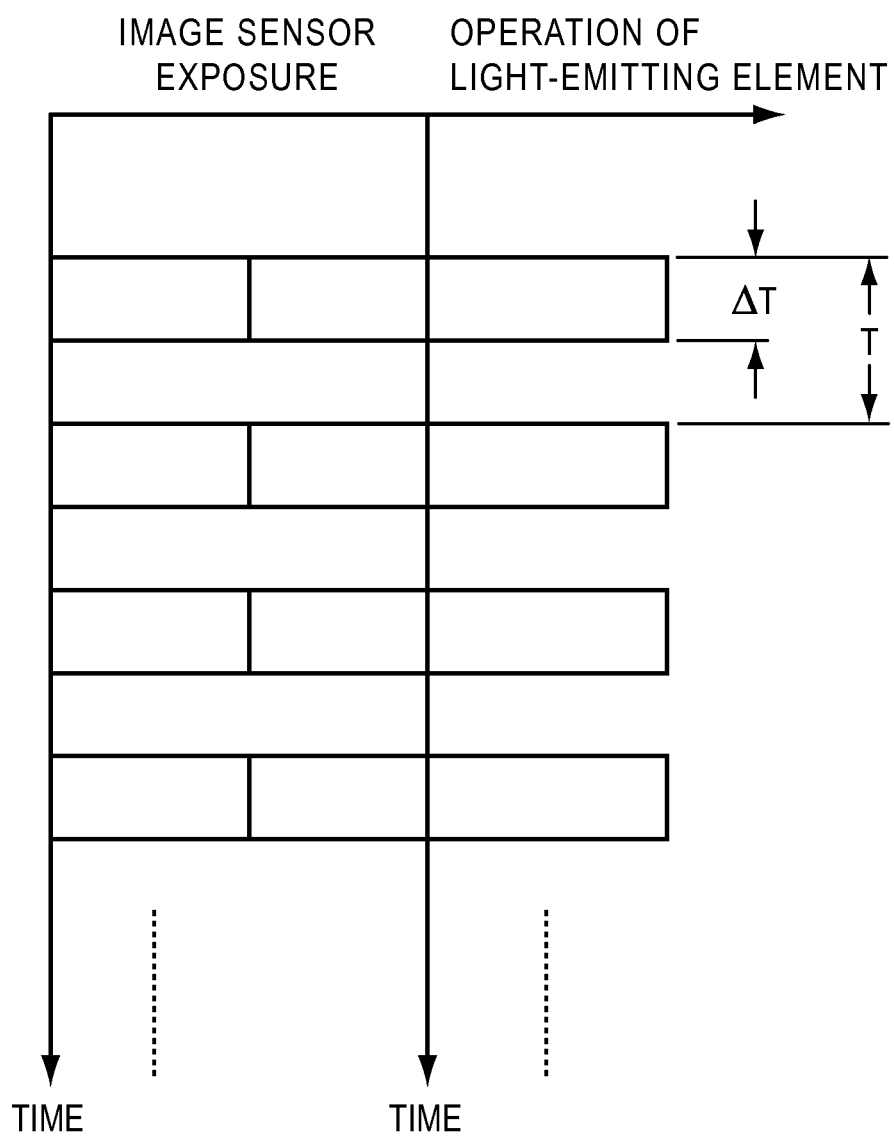
FIG. 31 is a time chart showing the timing of the operation of the light emitting-element and the exposure of the image sensor.

FIG. 31 is a time chart showing the timing of the operation of the light emitting-element and the exposure of the image sensor. The light emitting-element 2221 such as a laser diode is made to generate light pulses rather than continuous light (CW) for the purpose of reducing power consumption. The cycle (T) of a light pulse and a time period ($\Delta T$) for illumination are properly selected from the moving speed of fine particles to be measured. If the cycle T is too long, problems may arise that, for example, fine particles themselves may not be detected or a captured image becomes blurred. If the cycle T is too short, the light application time $\Delta T$ is also short and thus there is a drawback that the signal/noise ratio is degraded.

In FIG. 30, the exposure time of the image sensor 2231 is the same as that of the light emitting-element 2221. This period is optimized by taking into consideration the signal/noise ratio of the entire system. The number of pixels of the image sensor mainly depends upon the size of fine particles to be measured. If the size of fine particles to be measured is from 1 micrometer to 100 micrometers, the number of pixels may be approximately 10,000.

Hereafter, an algorithm for detecting smoke particles, dust and pollen will be described. This method is not limited to the present embodiment, any may be applied to apparatus according to second and third embodiments described later.

Here, an output taken by the image sensor along x-axis (i-th) and y-axis (j-th) is indicated as V (i,j). Depending on the configuration of a focal length of a lens, there may be a difference in an output of the image sensor per pixel. Therefore, calibration is carried out at the beginning to adjust all of the pixels so that offset and sensitivity fall within a certain range. This adjustment may be carried out by hardware means or software means. In the following description, V (i,j) is an output value after the adjustment is carried out.

First, a state without the presence of obstacles, such as smoke particles, dust and pollen, is considered. In this case, transmitted light is detected directly by the image sensor without scattering, and thus its output V_non (i,j) has a very small variance $\sigma$_non for the entire pixels.

When any of fine particles such as smoke particles, dust or pollen is entered, light is scattered thereby, resulting in a reduction in an amount of transmitted light. This enables to detect the fine particles. A predetermined value V_noise is set by taking into accounts the stability of LD inside the detection apparatus, shot noises which may occur in the image sensor, noises in amplifier circuitry, and thermal noises. If this value is exceeded, it is determined that a signal is supplied. While the fine particles may be introduced by generating airflow, natural diffusion or natural introduction of particles may be utilized without generating the airflow.

When it is determined that a signal is supplied, smoke particles, dust and pollen are distinguished in accordance with the following procedure.

1. When it is determined that a signal is supplied to all of the pixels, that is determined to be attributable to smoke particles.

In other words, when $$V(i,j) < V\_\text{non} - V\_\text{detect-1}$$

is valid for all of the pixels, smoke particles are identified. Here, V_detect-1 is a constant threshold larger than V_noise. Even if very large particles are introduced, the signal is detected in all of the pixels. However, as stated previously, in this case, such particles are removed in advance by a filter. Further, a concentration of the smoke is identified depending on an intensity of the signal.

2. When part of pixels have responded, dust or pollen is identified. Binarization is carried out to identify a portion shielded by fine particles. FIG. 28 is a view schematically showing such binarization. For example, if a dust has a size and shape as shown in (a), that is identified by binarization as an image as shown in (b). V_detect-2 are used as a parameter for performing the binarization, and pixels that output a signal exceeding this threshold V_detect-2 are counted. The count number is proportional to a light-shielding cross-sectional area by the fine particles, with respect to the incident light. On the basis of the counted pixel number, fine particles of 20 micrometers or less or 50 micrometers or more are identified as dust.

3. When the result of the above size measurement of the fine particles indicates that the particles are determined to have a size from 20 micrometer to 50 micrometer, it is possible that the particles are pollen. Therefore, in such a case, determination by a further method is necessary. In general, since dust is lighter than pollen, dust has a higher moving speed in airflow than pollen. Therefore, the moving speed of floating particles is calculated. When the moving speed of the particles is at a predetermined level or higher, those particles are determined to be dust, and otherwise they are determined to be pollen. When the airflow is not rising and the fine particles flow from top to down, the particles having a higher moving speed is considered pollen and slow particles are considered dust.

The speed value is obtained by taking two images at successive units of time, and calculating from a moving distance between the images and a frame time.

Figure 32A:
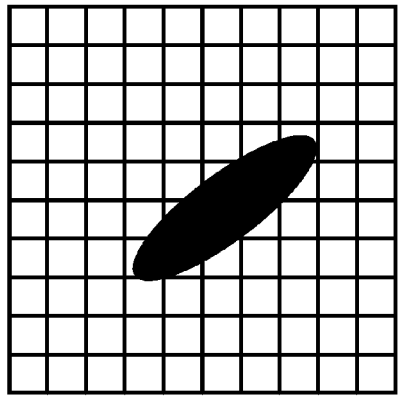
FIGS. 32(a) and (b) are views showing schematized image information of a binarized particle image.
Figure 32B:
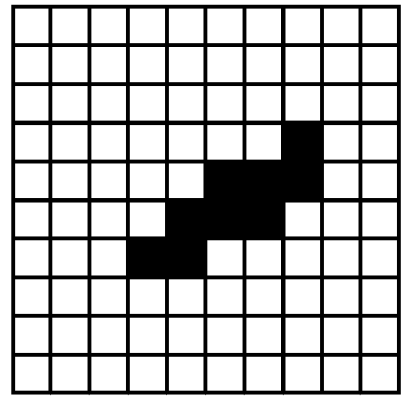

FIGS. 32(*a*) and (*b*) are views showing schematized image information of a binarized particle image.

Figure 33A:
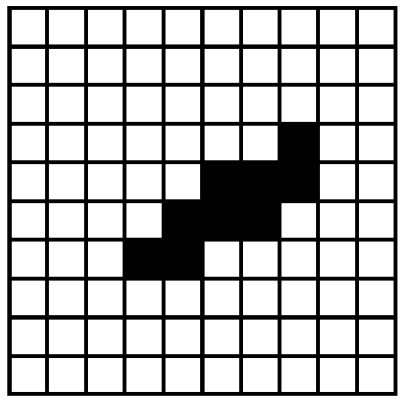
FIGS. 33(a) and (b) are views showing temporal changes of a binarized image signal.
Figure 33B:
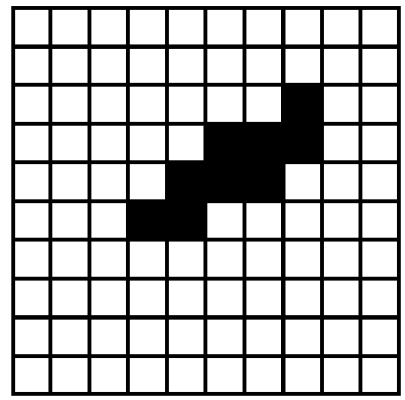

FIGS. 33(a) and (b) show temporal a change in a binarized image signal. In this example, it is recognized that a particle is moving upwardly. In order to recognize movement of particles from image information, a correlation value conventionally used in related technology can be utilized. As a result of determining the moving speed, when it is not lower than or not higher than a predetermined speed, the particles can be identified as dust or pollen, respectively.

In this description, detection of fine particles such as dust and pollen has been mainly described. However, by improving the analytical algorithm of the present apparatus, it is possible to produce a histogram of passing particles over a certain period in terms of size or weight of fine particles contained in an introduced gas. From this result, it is possible to analyze what types of fine particles exist in a room or in the open air.

FIG. 34 is a view describing a modified embodiment of the photodetector. In the aforementioned embodiment, the image sensor as a photodetector is provided with detection elements in the form of a matrix of approximately 100×100. However, a photodetector is not necessarily provided with a matrix of detection elements, and a photodetector having detection elements 51 disposed in a striped form may be used. That is, in this apparatus, when airflow is generated, the moving direction of fine particles is considered to run along a direction of the airflow. Therefore, detection of particles as in the foregoing embodiment is possible, by utilizing a photodetector 2250 having a striped configuration wherein elongated detection elements 2251 are extended in a direction perpendicular to the moving direction of the fine particles.

Figure 34A:
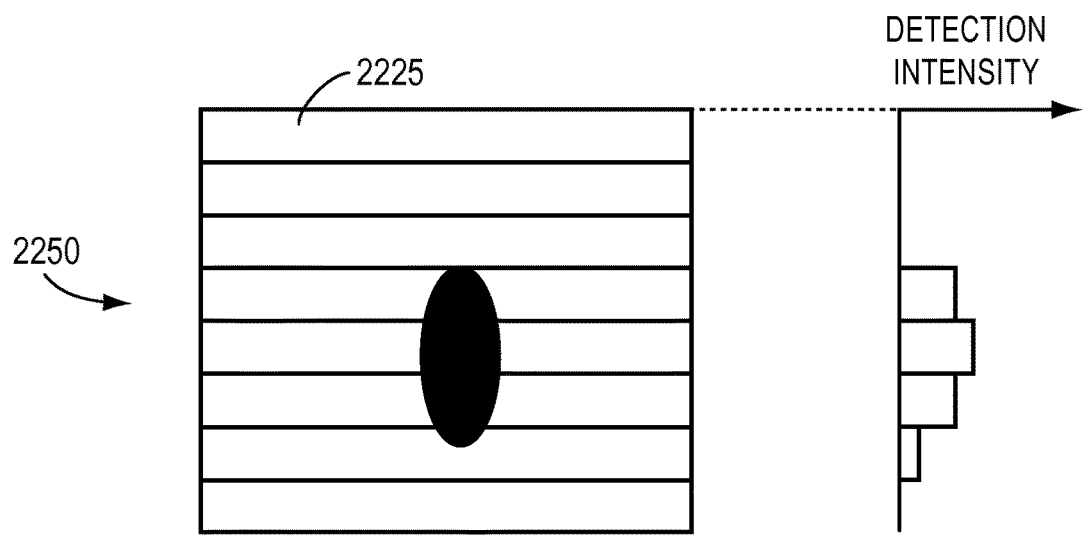
FIGS. 34(a) and (b) are views showing a modified embodiment of a photodetector, which indicate particle detection at different times for each view. Each view shows a positional relation between the photodetector and the particle at left side and output values at right side.
Figure 34B:
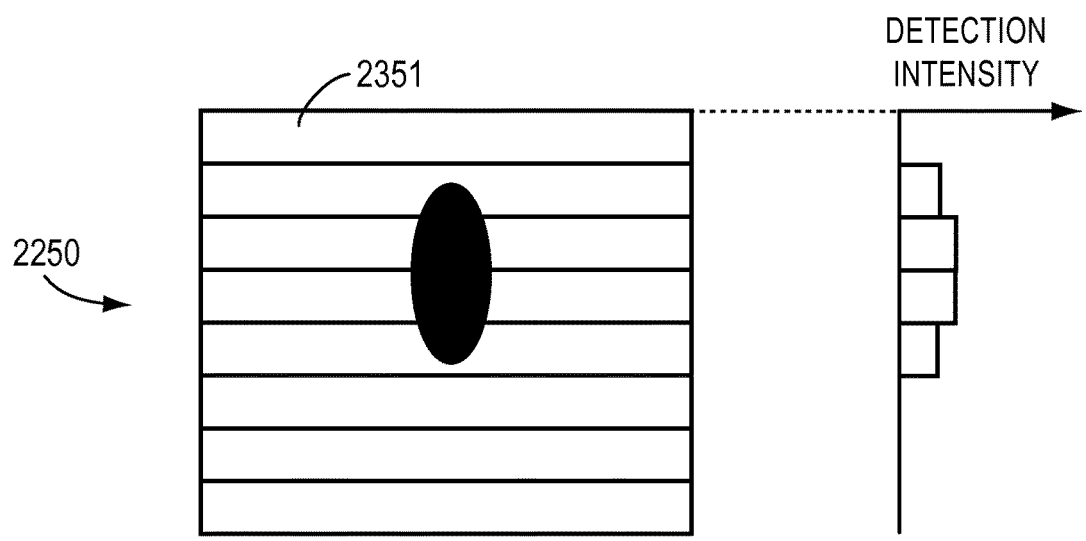
Figure 35:
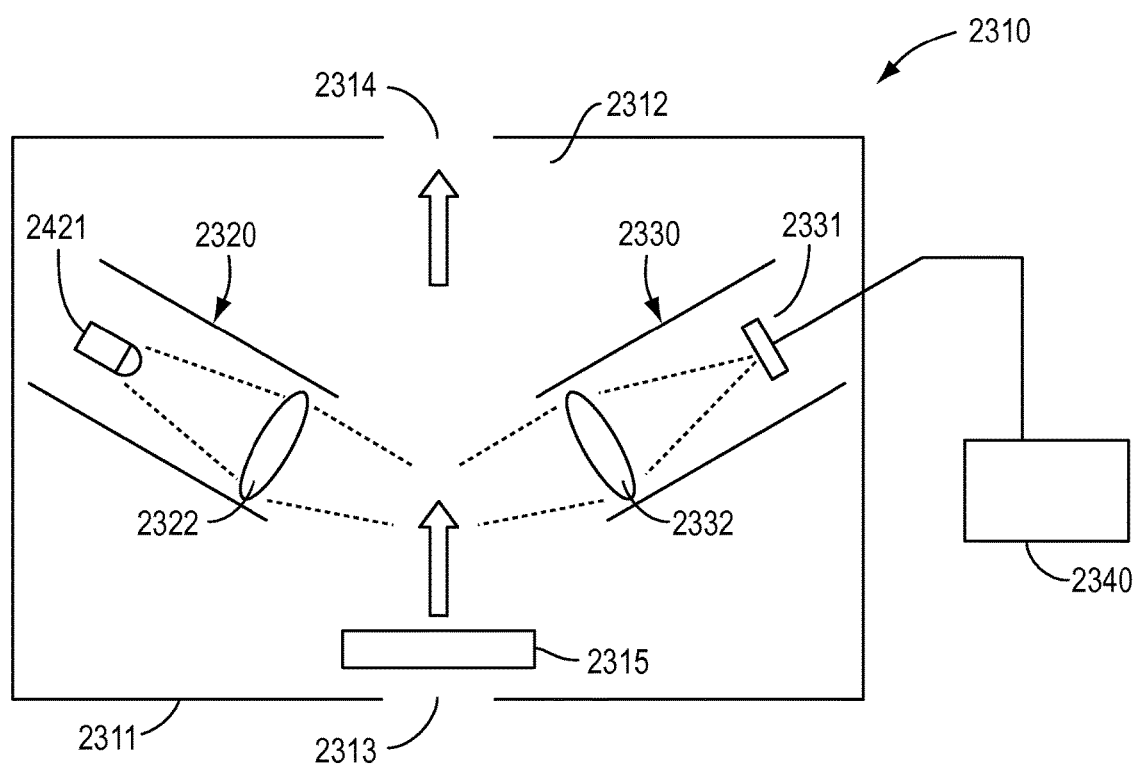
FIG. 35 is a schematic view showing a configuration of a particle detection apparatus in one embodiment.

FIGS. 34(a) and (b) show particle detection at different times when the photodetector 50 is used. In each figure, a positional relation between the photodetector and a particle is shown on the left and output values are shown on the right. FIG. 34(a) shows an initial state and FIG. 34(b) show a state after a predetermined time period after the state of FIG. 34(a). Each of the detection elements 2251 constituting a stripe can output a signal which is substantially proportional to the area of an image. Therefore, by establishing and comparing the output values, the position of a particle at that time and a particle moving speed may be determined. For example, when data obtained from the individual stripe-shaped light detection elements 2251 is processed using a spatial filter as in a sensing device, the size and the moving speed of the fine particle can be easily obtained. In this case, however, there is a certain tradeoff between the particle size and the moving speed.

This method can reduce an amount of data to be processed, compared with a case wherein an image sensor in the form of a matrix is used, and therefore this method is advantageous in that data processing can be performed more easily and rapidly.

Figure 36:
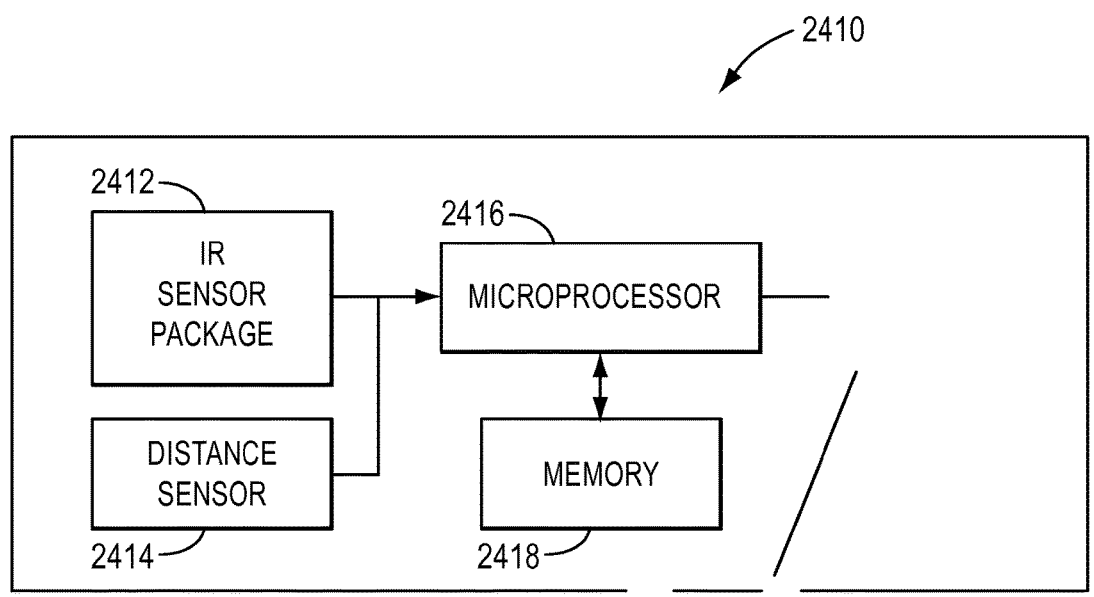
FIG. 36 is a block diagram representative of an embodiment of the present invention.

FIG. 36 is a schematic view showing the configuration of a particle detection apparatus according to a second embodiment of the present invention. In the first embodiment, a particle detection apparatus utilizing transmitted light was described. However, with a method of measuring reflected light or scattered light as described in FIG. 6, it is possible to detect smoke particles, dust and pollen. The description of operation of each component is omitted by attaching thereto a reference numeral which is greater by 100 than the numeral reference of a corresponding component shown in FIG. 30.

Regarding the positional relation between a light source 2320 and a detection device 2330, they are disposed on opposite sides of airflow, but they are not necessarily disposed in such a way. For example, the light source and the detection device may be disposed on the same side of the airflow, and in that case, light from the light source may be illuminated from either an upstream side or a downstream side of the airflow. Further, the light source and the detection device are disposed in a plane that is orthogonal to the airflow, and they may be disposed not linearly like that of FIG. 30, but in a tilted direction within the plane.

In the apparatus according to the first embodiment, as transmission light is always incident, it has to keep a certain level of an input range. As a result, measurements may not always be performed properly. In contrast, in accordance with the detection system of the second embodiment, a dynamic range of the image sensor of the apparatus can be utilized to advantage. Therefore, it is advantageously suitable for a high sensitive measurement of fine particles.

This apparatus is applicable to systems that detect fine particles including dust, pollen and smoke particles, such as an air cleaner, an air conditioner, a vacuum cleaner, an air fan, a fire alarm, a sensor for environmental measurement and a fine particle detection apparatus in a clean room.

Temperature Sensor

FIG. 36 is a block diagram illustrating an embodiment of the IR thermometer 2410. This embodiment includes an IR sensor package/assembly 2412, distance sensor 2414, a microprocessor 2416 and a memory 2418.

In one embodiment one or more sensors, which can be in an assembly 2412 includes a sensor. In one embodiment a sensor and a temperature sensor is provided. As a non-limiting example, the sensor can be an IR sensor. In one embodiment the sensor is an IR sensor. In one embodiment a temperature sensor senses the temperature of the sensor and/or the temperature of the ambient environment. The sensor is configured to capture thermal radiation emanating from a target object or target body part, e.g., a subject's forehead, armpit, ear drum, etc., which is converted into an electrical temperature signal and communicated, along with a signal regarding the temperature of the sensor as measured by the temperature sensor, to microprocessor 2416, as is known in the art. Distance sensor 2414 is configured to emit radiation from IR thermometer 2410 and to capture at least a portion of the emitted radiation reflected from the target, which is converted into an electrical distance signal and communicated to microprocessor 2416. Microprocessor 2416 is configured to, among other things, determine a temperature value of the target based on the signal from sensor package/assembly 2412, determine an ambient environment or thermometer temperature, and to determine a distance value corresponding to the distance between thermometer 2410 and the target using a correlation routine based on the signal from distance sensor 2414 and the characteristics of the reflected radiation. In various embodiments, the temperature signal, distance signal, temperature value, distance value, or any combination thereof may be stored in memory 2418.

Memory 2418 includes therein predetermined compensation information. This predetermined compensation information may be empirically predetermined by performing clinical tests. These clinical tests may relate the detected temperature of a target (e.g., forehead), the distance of the thermometer from the target, as well as the actual temperature of the target and the ambient environment or thermometer temperature. These clinical tests may further relate the temperature of the target, either the detected temperature, the actual temperature, or both, to, e.g., an actual oral or oral-equivalent temperature. Accordingly, target temperatures of various subjects having oral temperatures between, e.g., 94° Fahrenheit to 108° Fahrenheit, may be measured using a thermometer at various known distances from the targets, e.g., from 0 centimeters (i.e., thermometer contacts target) to 1 meter, in increments of, e.g., 1 centimeter, 5 centimeters, or 10 centimeters. In some embodiments, the range of distances corresponds to a range of distances over which thermometer 2410 may be operational. Additionally, these measurements may be conducted in environments having various ambient temperatures between, e.g., 60° Fahrenheit to 90° Fahrenheit. These data may be used to create compensation information, such as a look-up table or mathematical function, whereby a compensated temperature of the target may subsequently be determined from a measured distance value, e.g., using distance sensor 2414, a measured target temperature value, e.g., using IR sensor package or assembly 2412, and, in some embodiments, an ambient environment temperature value and/or thermometer temperature value. In other embodiments, data relating to actual oral or oral-equivalent temperatures may be further used to create the compensation information, whereby a compensated oral or compensated oral-equivalent temperature may be determined from a measured distance value, a measured target temperature value, and, in some embodiments, an ambient environment temperature value and/or thermometer temperature value.

For example, where d is defined as a distance between the target and thermometer 2410, the predetermined compensation information for obtaining a compensated temperature in degrees Fahrenheit may be a linear function or functions defined by the following relationships:

$$\text{Compensated Temperature} = \text{Target Temperature} + A*d + B$$

Or $$\text{Compensated Temperature} = \text{Target Temperature} + C*d + D \{\text{for } 0 < d \leq Y\}, \text{ and}$$

$$\text{Compensated Temperature} = \text{Target Temperature} + E*d + F \{\text{for } Y < d \leq Z\},$$

Where A, C, and E are coefficients having dimensions of Temperature/Length; B, D and F are coefficients having dimensions of Temperature; and Y and Z are distances from the target. Values of A, B, C, D, E, F, Y, and Z may be determined empirically from clinical tests. For purposes of illustration and not limitation, the following exemplary and approximate values for the coefficients and distances are provided: A=0.05, B=0.1, C=0.05, D=0.2, E=0.15, F=0.1, Y=15, and Z=30. However, as will be recognized by persons having ordinary skill in the art, other values for each coefficient and distance may be used depending on various design features and aspects of a thermometer 2410.

It is also possible for the mathematical function to be of a higher degree or order, for example, a mathematical function that is non-linear with respect to the measured distance to obtain the compensated temperature, such as the following quadratic equation:

$$\text{Compensated Temperature} = \text{Target Temperature} + G*d^2 - H*d + L$$

Where G, H, and L are coefficients determined from the clinical tests. For purposes of illustration and not limitation, the following exemplary and approximate values for the coefficients are provided: 0=0.001, H=0.15, and L=0.1. However, as will be recognized by persons having ordinary skill in the art, other values for each coefficient may be used depending on various design features and aspects of thermometer 2410.

The compensation information may alternatively be provided as various offset values, whereby, for each distance increment or range of distances from the target surface, there is a corresponding offset value. In various embodiments, these offsets may be fixed for each of the distance increments or range of distances from the target surface. For example, in various embodiments, the offset value may be, e.g., any one of 0.1° F., 0.2° F., or 0.5° F. over a range of distances from the target surface such as 0 cm to 5 cm, 0 cm to 20 cm, or 5 cm to 30 cm. For example, in one embodiment, the offset value may be 0.0° F. from 0.0 cm to 0.1 cm, 0.1° F. from 0.1 cm to 3.0 cm, 0.2° F. from 3.0 cm to 15 cm, and 0.5° F. from 15.1 cm to 30 cm. Alternatively, the compensation information may be in the form of a single, e.g., "best-fit," offset value that may be used to determine a compensated temperature from any of the target temperatures over a distance range, either the entire distance range recited above or a portion thereof. For example, the "best-fit" offset value may be, e.g., any one of 0.1° F., 0.2° F., or 0.5° F. For example, in one embodiment, the offset value may be 0.1° F. over the distance range from 0.0 cm to 10 cm, and 0.0° F. for greater distances. In other embodiments, the offset value may be 0.1° F. over the distance range from 0.0 cm to 30 cm, and 0.0° F. for distances greater than 30 cm.

In other embodiments, the compensation information may be in the form of a look-up table, which may be devised from predetermined information collected during clinical tests, such as actual target temperature, measured target temperature, ambient environment and/or thermometer temperature, and distance measurements, such that, subsequently, a compensated temperature may be determined by identifying in the look-up table those values that best correspond to the measured distance and measured target-temperature values. In the event of an imperfect match between the measured values and the table values, the closest table values may be used, or, additional values interpolated from the table values may be used. In other embodiments, the compensation information may include a combination of more than one of the approaches (e.g., mathematical function, offset value, look-up table) described above Further, as noted above, the ambient environment temperature value and/or thermometer temperature value may be used in generating compensation information. It may be beneficial to include these values as factors in the compensation information because these values may increase the accuracy of a compensated temperature calculated based on the compensation information. For example, the above discussed mathematical functions may be modified based on ambient environment temperature and/or thermometer temperature. For example, a first "best fit" offset value (e.g., 0.1° F.) may be used when the ambient temperature is within a first range of temperatures (e.g., 60° F. to 75° F.), and a second "best fit" offset value (e.g., 0.2° F.) may be used when the ambient temperature is within a second range of temperatures (e.g., 75° F. and 90° F.).

Microprocessor 2416 is configured to use a temperature value corresponding to a target and a distance value corresponding to the distance between thermometer 2410 and the target to determine a compensated temperature using the predetermined compensation information stored in memory 2418. In some embodiments, Microprocessor 2416 may be further configured to use an ambient and/or thermometer temperature in this determination. In some embodiments, the predetermined compensation information may be based in part on ambient and/or thermometer temperature. In those embodiments where the predetermined compensation information includes predetermined information concerning oral or oral-equivalent temperatures, Microprocessor 2416 may be further configured to determine a compensated temperature corresponding to an oral or oral-equivalent temperature.

Microprocessor 2416 may further store one or more compensated temperature values in memory 2418. In various embodiments, the microprocessor is further configured to interpolate additional values from any values stored in a look-up table in memory 2418.

Figure 37:
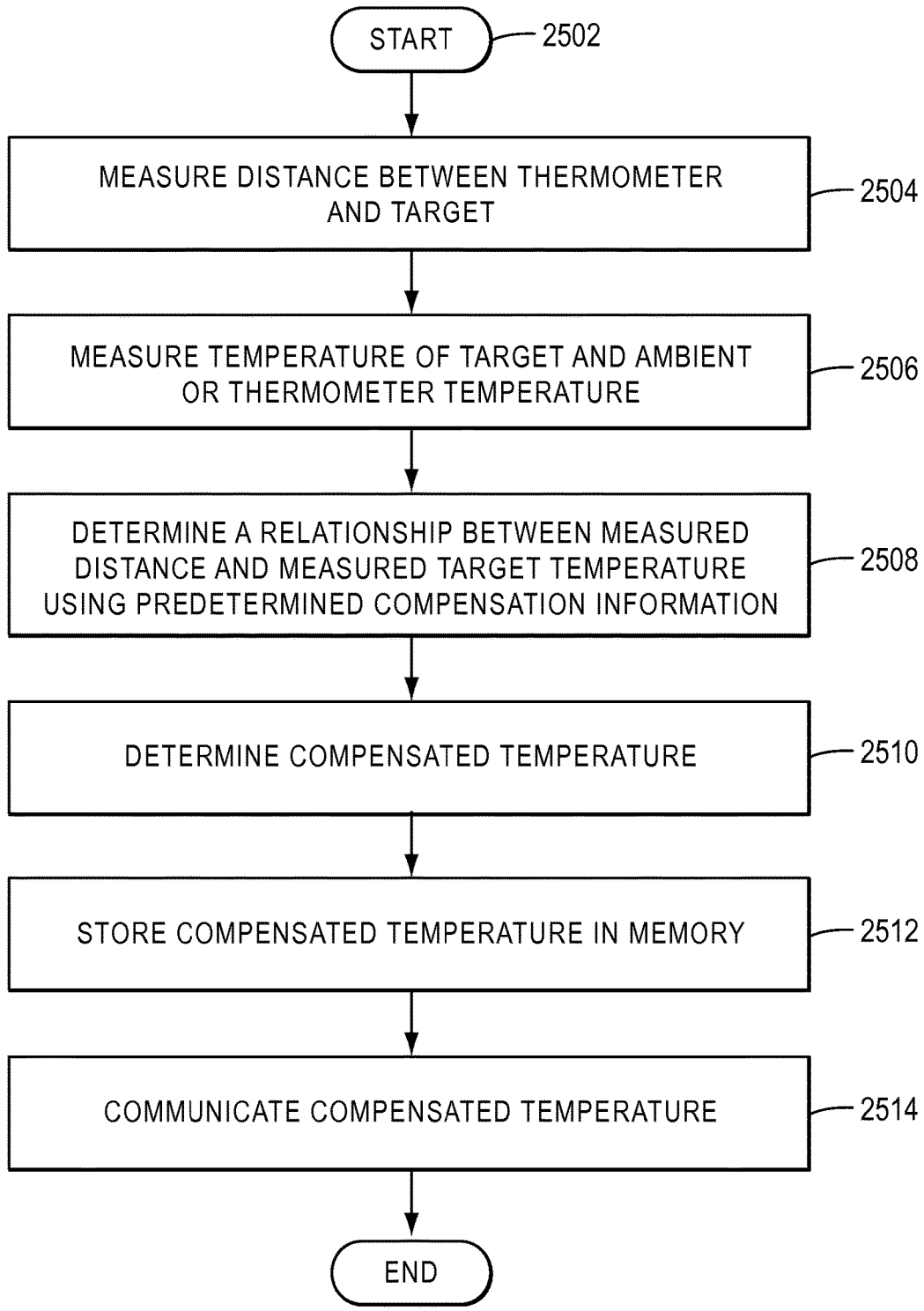
FIG. 37 is a flow chart showing the method for compensated temperature determination in accordance with an embodiment of the invention.
Figure 38A:
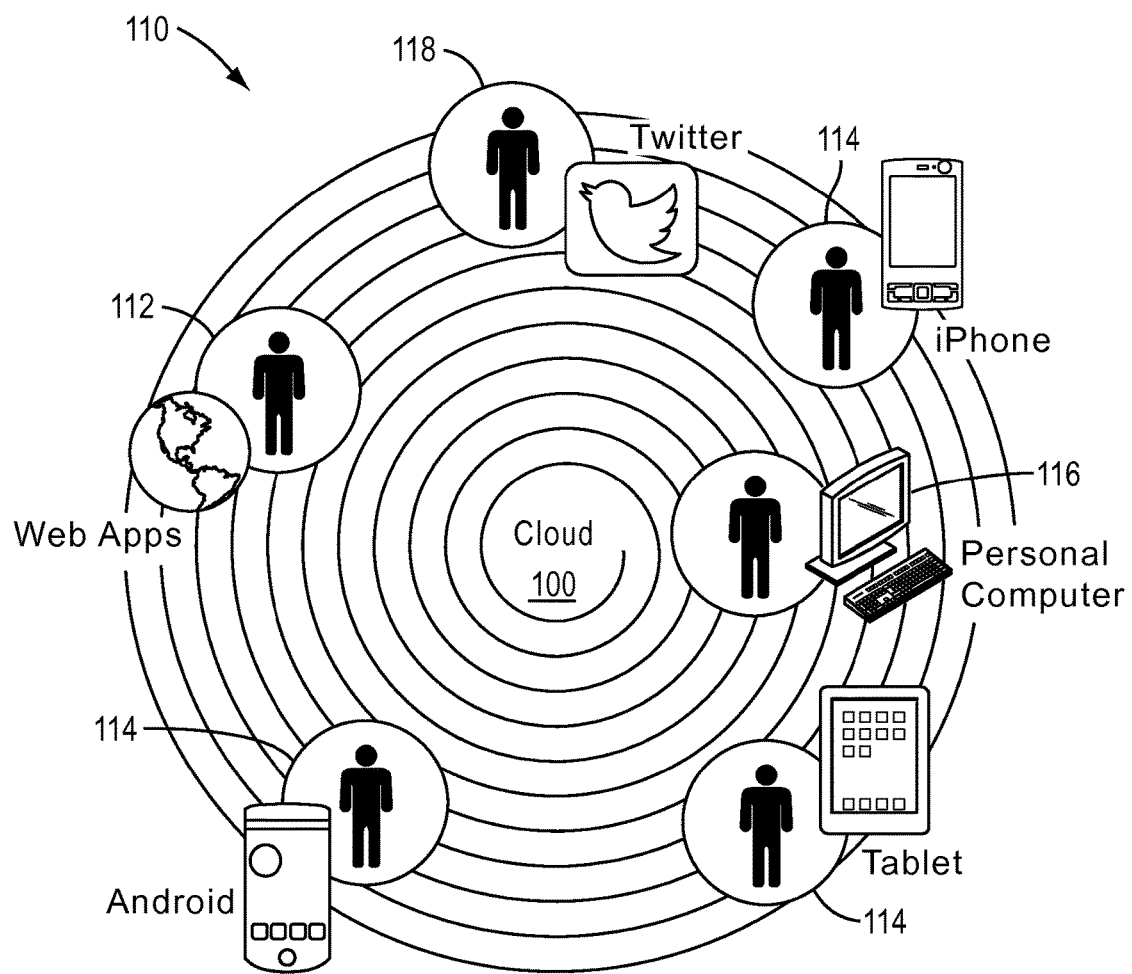
FIGS. 38(a)-(e) illustrate one embodiment of a Cloud Infrastructure that can be used with the present invention.
Figure 38B:
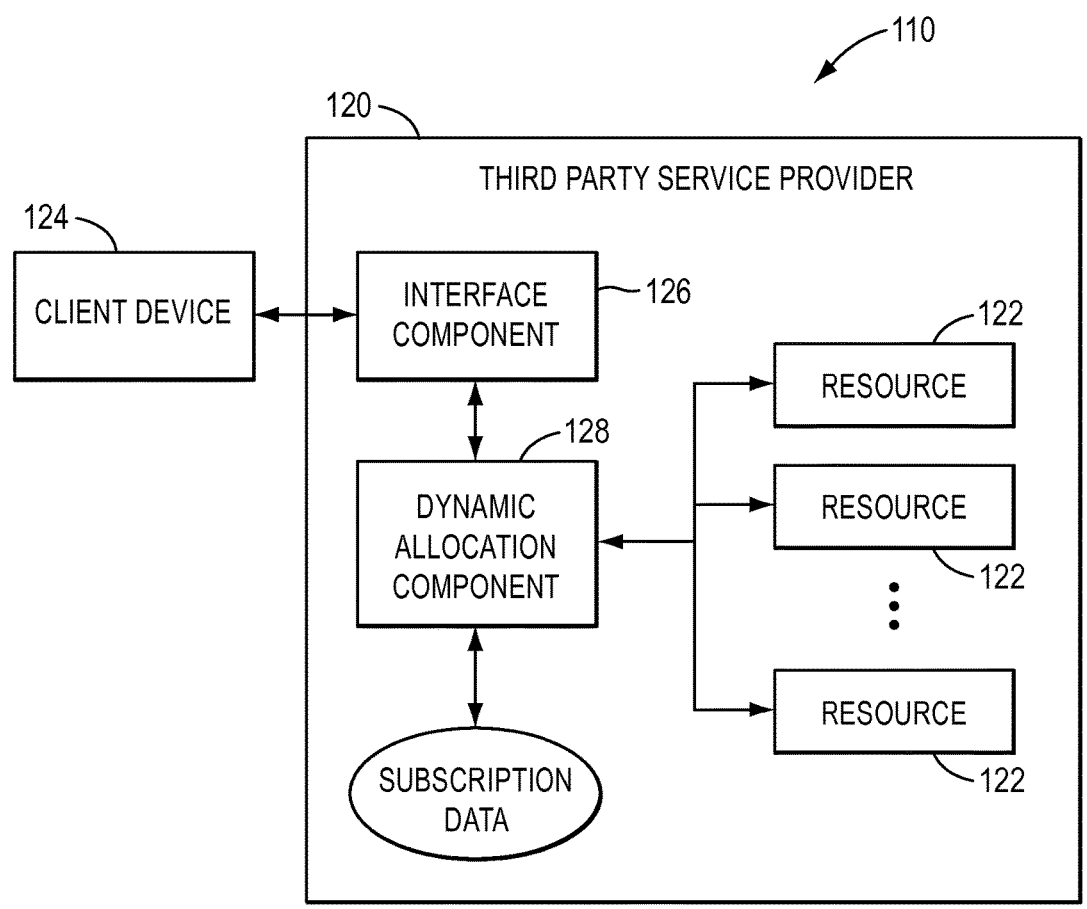
Figure 38C:
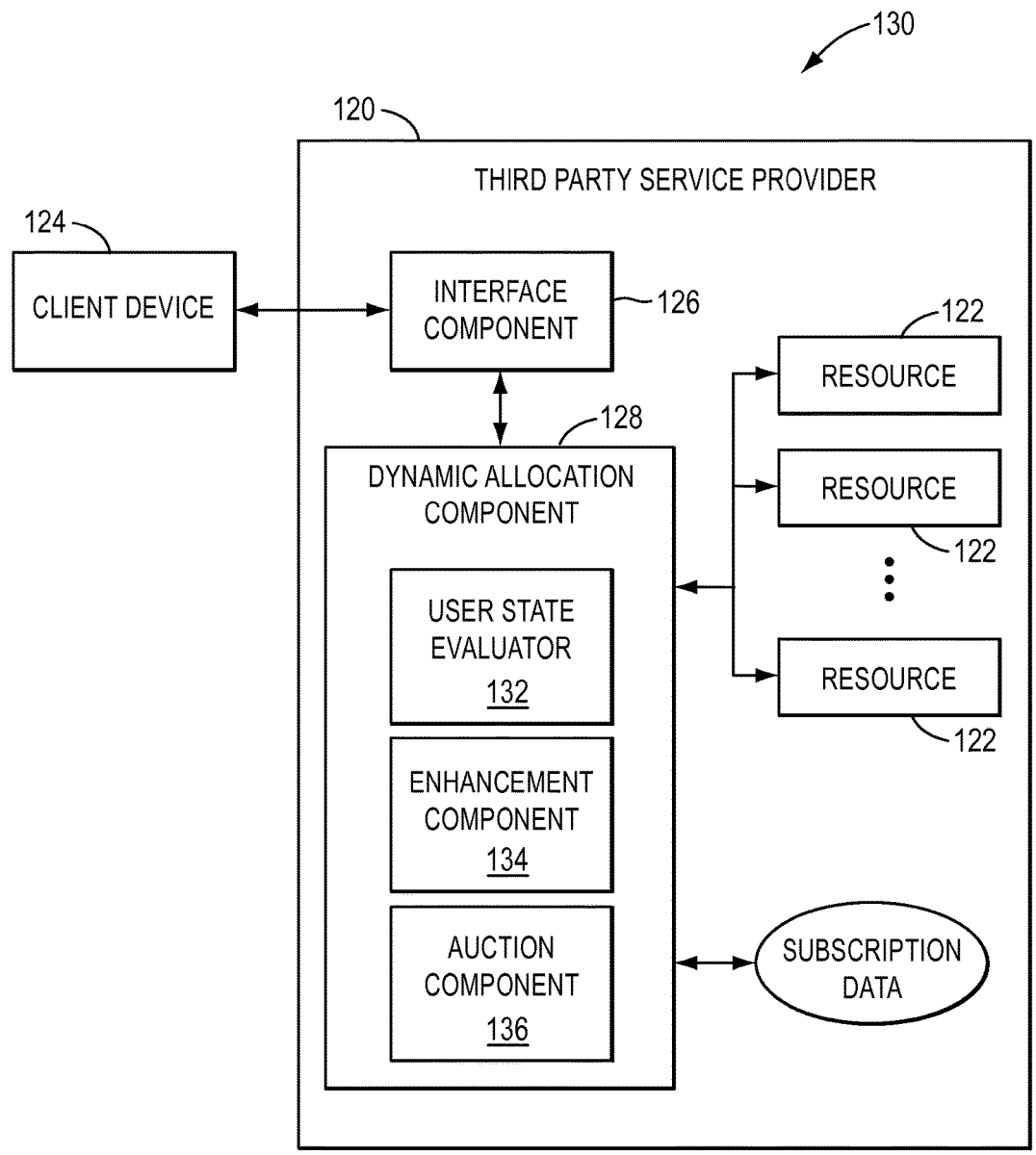
Figure 38D:
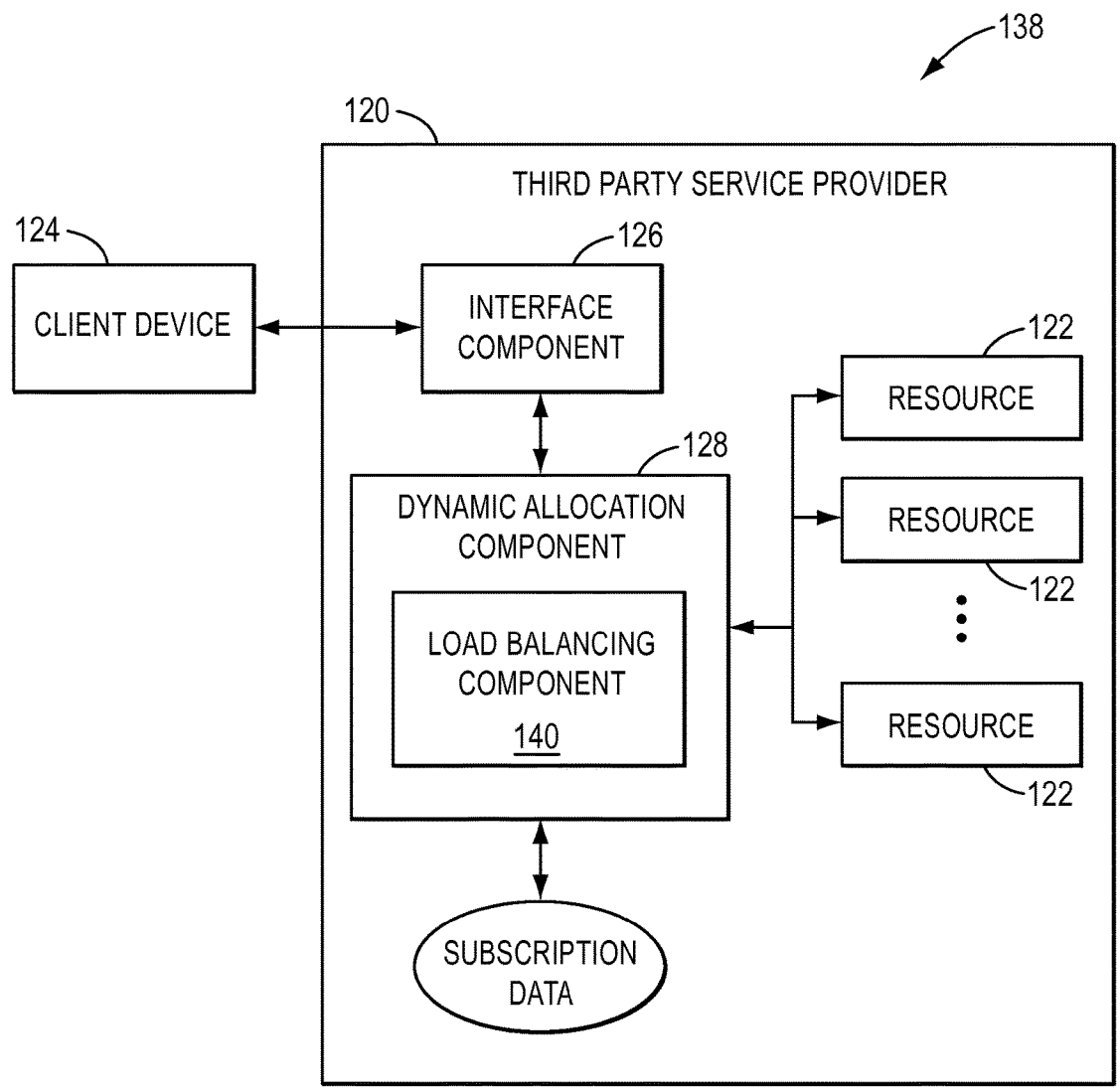
Figure 38E:
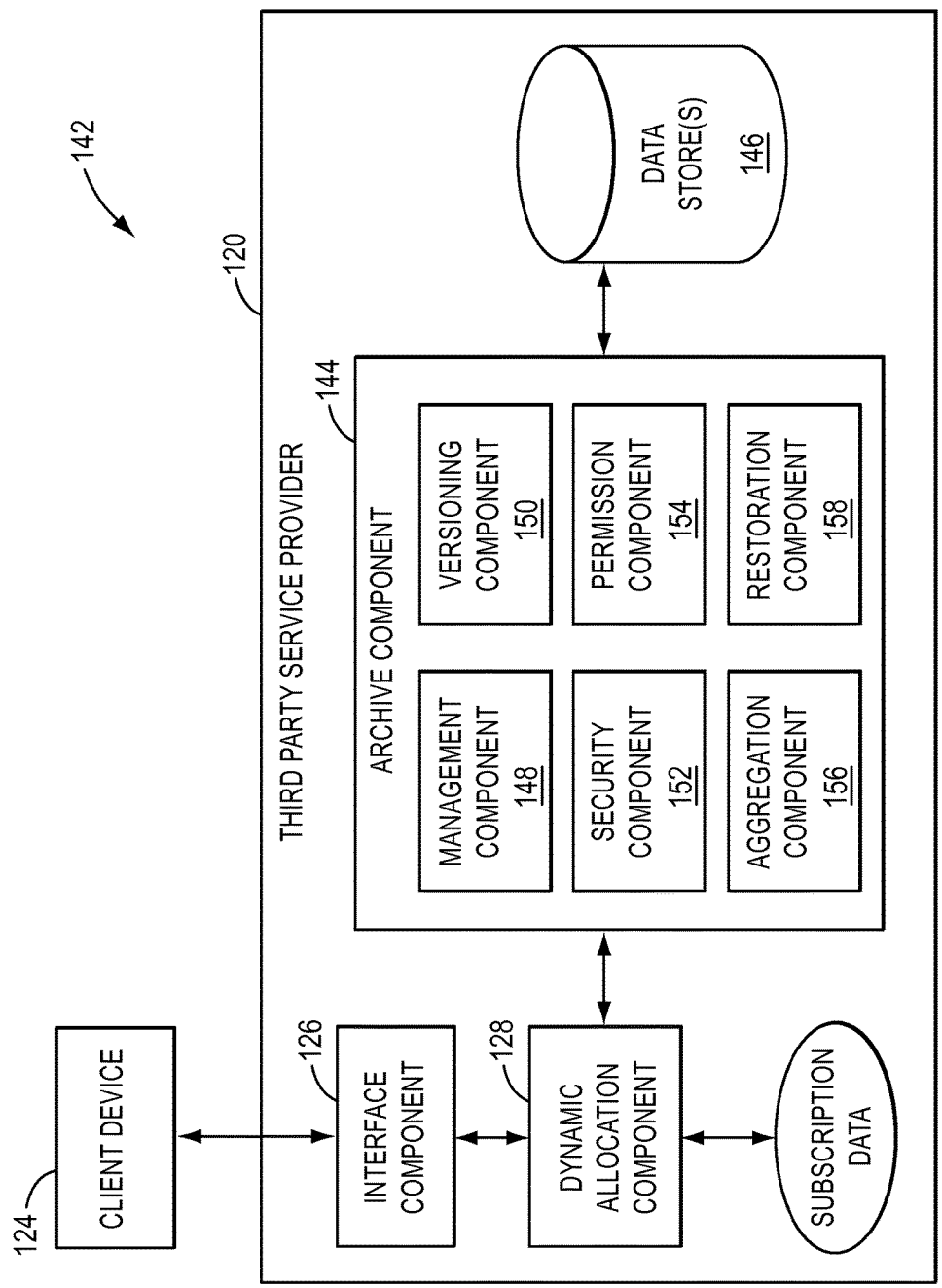

Referring to FIG. 37, the flow chart shows an embodiment of a method for determining a compensated temperature based on a measured temperature of a target on that subject, e.g., that subject's forehead. In step 2502, the process for determining the compensated temperature starts, e.g., by the user depressing a start button to, e.g., activate thermometer 2410. In step 2504, distance sensor 2414 is used to emit radiation and capture reflected radiation from a target to generate a distance signal, which is communicated to microprocessor 2416. Microprocessor 2416 determines a distance value from the distance signal, which microprocessor 2416 may store in memory 2418. In step 2506, sensor package/assembly 2412 is used to capture thermal radiation emanating from the target to generate a temperature signal, and, optionally, to capture an ambient and/or thermometer temperature, which are communicated to microprocessor 2416. Microprocessor 2416 determines a temperature value from the temperature signal, which microprocessor 2416 may store in memory 2418. In optional step 2508, which is performed when the predetermined compensation information includes a look-up table, microprocessor 2416 determines a relationship between the distance value and the temperature values using predetermined compensation information. In step 2510 microprocessor 16 determines a compensated temperature value based on the predetermined compensation information. In step 2512, microprocessor 2416 stores the compensated temperature in memory 2418. In step 2514, the compensated temperature value is communicated.

Humidity Sensor

Absolute humidity is the total amount of water vapor present in a given volume of air. It does not take temperature into consideration. Absolute humidity in the atmosphere ranges from near zero to roughly 30 grams per cubic meter when the air is saturated at 30° C.

Absolute humidity is the mass of the water vapor ($m_w$), divided by the volume of the air and water vapor mixture ($P_{net}$), which can be expressed as:

$$AH = \frac{m_w}{p_{net}}.$$

The absolute humidity changes as air temperature or pressure changes. This makes it unsuitable for chemical engineering calculations, e.g. for clothes dryers, where temperature can vary considerably. As a result, absolute humidity in chemical engineering may refer to mass of water vapor per unit mass of dry air, also known as the mass mixing ratio (see "specific humidity" below), which is better suited for heat and mass balance calculations. Mass of water per unit volume as in the equation above is also defined as volumetric humidity. Because of the potential confusion, British Standard BS 1339 (revised 2002) suggests avoiding the term "absolute humidity". Units should always be carefully checked. Many humidity charts are given in g/kg or kg/kg, but any mass units may be used.

The field concerned with the study of physical and thermodynamic properties of gas-vapor mixtures is named psychrometrics.

The relative humidity ($\phi$) of an air-water mixture is defined as the ratio of the partial pressure of water vapor (H2O) ($e_w$) in the mixture to the saturated vapor pressure of water ($e^*_w$) at a given temperature. Thus the relative humidity of air is a function of both water content and temperature.

Relative humidity is normally expressed as a percentage and is calculated by using the following equation: [5]

$$\phi = \frac{e_w}{e^*_w} \times 100\%$$

Relative humidity is an important metric used in weather forecasts and reports, as it is an indicator of the likelihood of precipitation, dew, or fog. In hot summer weather, a rise in relative humidity increases the apparent temperature to humans (and other animals) by hindering the evaporation of perspiration from the skin. For example, according to the Heat Index, a relative humidity of 75% at 80.0° F. (26.7° C.) would feel like 83.6° F.±1.3° F. (28.7° C.±0.7° C.) at ~44% relative humidity.

Specific Humidity:

Specific humidity (or moisture content) is the ratio of water vapor mass ($m_v$) to the air parcel's total (i.e., including dry) mass ($m_a$) and is sometimes referred to as the humidity ratio. [8] Specific humidity is approximately equal to the "mixing ratio", which is defined as the ratio of the mass of water vapor in an air parcel to the mass of dry air for the same parcel.

Specific Humidity is defined as:

$$SH = \frac{m_v}{m_a}.$$

Specific humidity can be expressed in other ways including:

$$SH = \frac{0.622 p_{(H_2O)}}{p_{(dry\,air)}}$$

$$0.622 = \frac{MM_{H_2O}}{MM_{dry\,air}}$$

or:

$$SH = \frac{0.622 p_{(H_2O)}}{p - 0.378 * p_{(H_2O)}}.$$

Using this definition of specific humidity, the relative humidity can be expressed as $$\phi = \frac{SH * p}{(0.622 + 0.378 * SH) p^*_{(H_2O)}} \times 100$$

However, specific humidity is also defined as the ratio of water vapor to the total mass of the system (dry air plus water vapor). For example, the ASHRAE 2009 Handbook defines specific humidity as "the ratio of the mass of water vapor to total mass of the moist air sample".

Various devices can be used to measure and regulate humidity. In one embodiment a psychrometer or hygrometer is used.

In one embodiment user monitoring device 10 and motion detection device 42 are used to detect at least one of a person's motion, movement and gesture for determining a person's sleep parameters, sleep activities, sleep state, or awake status, including but not limited to the following: sleep-related breathing disorders, such as sleep apnea, sleep-related seizure disorders, sleep-related movement disorders, such as periodic limb movement disorder, which is repeated muscle twitching of the feet, legs, or arms during sleep, determine restless legs syndrome (RLS), problems sleeping at night (insomnia): caused by stress, depression, hunger, physical discomfort, or other problems, sleep disorders that cause extreme daytime tiredness, such as narcolepsy, problems with nighttime behaviors, such as sleepwalking, night terrors, or bed-wetting, bruxism or grinding of the teeth during sleep, problems sleeping during the day because of working at night or rotating shift work known as shift work sleep disorder, determine stages of sleep, including but not limited to non-rapid eye movement (NREM) and rapid eye movement sleep (REM), and the like.

As a non-limiting example, one embodiment of a cloud system is illustrated in FIGS. 38(a)-38(e).

The cloud based system includes a third party service provider 120, that is provided by the methods used with the present invention, that can concurrently service requests from several clients without user perception of degraded computing performance as compared to conventional techniques where computational tasks can be performed upon a client or a server within a proprietary intranet. The third party service provider (e.g., "cloud") supports a collection of hardware and/or software resources. The hardware and/or software resources can be maintained by an off-premises party, and the resources can be accessed and utilized by identified users over Network Systems. Resources provided by the third party service provider can be centrally located and/or distributed at various geographic locations. For example, the third party service provider can include any number of data center machines that provide resources. The data center machines can be utilized for storing/retrieving data, effectuating computational tasks, rendering graphical outputs, routing data, and so forth.

In one embodiment, the third party service provider can provide any number of resources such as servers, CPU's, data storage services, computational services, word processing services, electronic mail services, presentation services, spreadsheet services, web syndication services (e.g., subscribing to a RSS feed), and any other services or applications that are conventionally associated with personal computers and/or local servers. Further, utilization of any number of third party service providers similar to the third party service provider is contemplated. According to an illustration, disparate third party service providers can be maintained by differing off-premise parties and a user can employ, concurrently, at different times, and the like, all or a subset of the third party service providers.

By leveraging resources supported by the third party service provider 120, limitations commonly encountered with respect to hardware associated with clients and servers within proprietary intranets can be mitigated. Off-premises parties, instead of users of clients or network administrators of servers within proprietary intranets, can maintain, troubleshoot, replace and update the hardware resources. Further, for example, lengthy downtimes can be mitigated by the third party service provider utilizing redundant resources; thus, if a subset of the resources are being updated or replaced, the remainder of the resources can be utilized to service requests from users. According to this example, the resources can be modular in nature, and thus, resources can be added, removed, tested, modified, etc. while the remainder of the resources can support servicing user requests. Moreover, hardware resources supported by the third party service provider can encounter fewer constraints with respect to storage, processing power, security, bandwidth, redundancy, graphical display rendering capabilities, etc. as compared to conventional hardware associated with clients and servers within proprietary intranets.

The cloud based system can include a client device that employs resources of the third party service provider. Although one client device is depicted, it is to be appreciated that the cloud based system can include any number of client devices similar to the client device, and the plurality of client devices can concurrently utilize supported resources. By way of illustration, the client device can be a desktop device (e.g., personal computer), motion/movement/gesture detection device, and the like. Further, the client device can be an embedded system that can be physically limited, and hence, it can be beneficial to leverage resources of the third party service provider.

Resources can be shared amongst a plurality of client devices subscribing to the third party service provider. According to an illustration, one of the resources can be at least one central processing unit (CPU), where CPU cycles can be employed to effectuate computational tasks requested by the client device. Pursuant to this illustration, the client device can be allocated a subset of an overall total number of CPU cycles, while the remainder of the CPU cycles can be allocated to disparate client device(s). Additionally or alternatively, the subset of the overall total number of CPU cycles allocated to the client device can vary over time. Further, a number of CPU cycles can be purchased by the user of the client device. In accordance with another example, the resources can include data store(s) that can be employed by the client device to retain data. The user employing the client device can have access to a portion of the data store(s) supported by the third party service provider, while access can be denied to remaining portions of the data store(s) (e.g., the data store(s) can selectively mask memory based upon user/device identity, permissions, and the like). It is contemplated that any additional types of resources can likewise be shared.

The third party service provider can further include an interface component that can receive input(s) from the client device and/or enable transferring a response to such input(s) to the client device (as well as perform similar communications with any disparate client devices). According to an example, the input(s) can be request(s), data, executable program(s), etc. For instance, request(s) from the client device can relate to effectuating a computational task, storing/retrieving data, rendering a user interface, and the like via employing one or more resources. Further, the interface component can obtain and/or transmit data over a network connection. According to an illustration, executable code can be received and/or sent by the interface component over the network connection. Pursuant to another example, a user (e.g. employing the client device) can issue commands via the interface component.

Moreover, the third party service provider includes a dynamic allocation component that apportions resources (e.g., hardware resource(s)) supported by the third party service provider to process and respond to the input(s) (e.g., request(s), data, executable program(s) and the like) obtained from the client device.

Although the interface component is depicted as being separate from the dynamic allocation component, it is contemplated that the dynamic allocation component can include the interface component or a portion thereof. The interface component can provide various adaptors, connectors, channels, communication paths, etc. to enable interaction with the dynamic allocation component.

Figure 39:
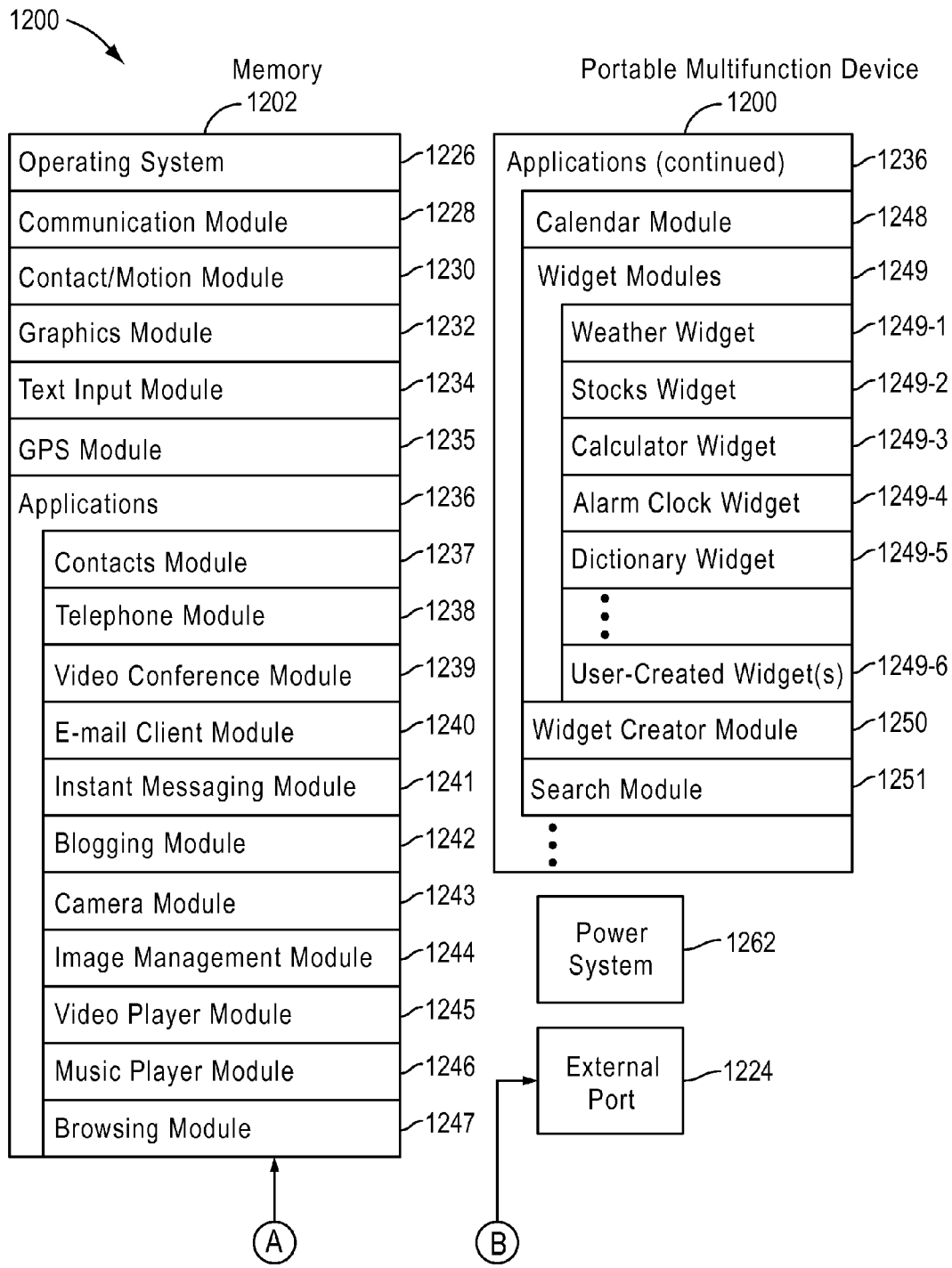
FIGS. 39-41 illustrate one embodiment of a mobile device that can be used with the present invention.
Figure 40:
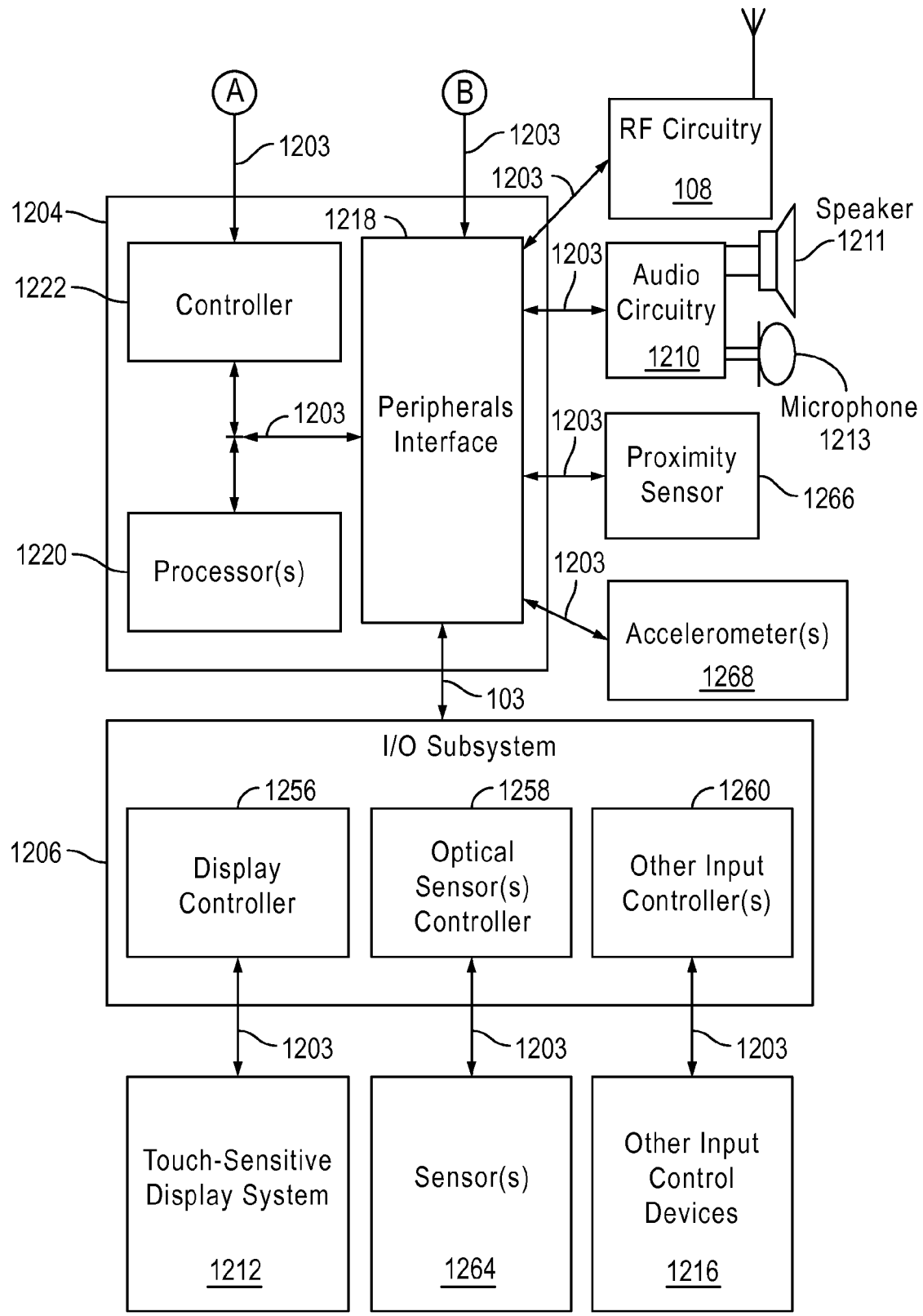
Figure 41:
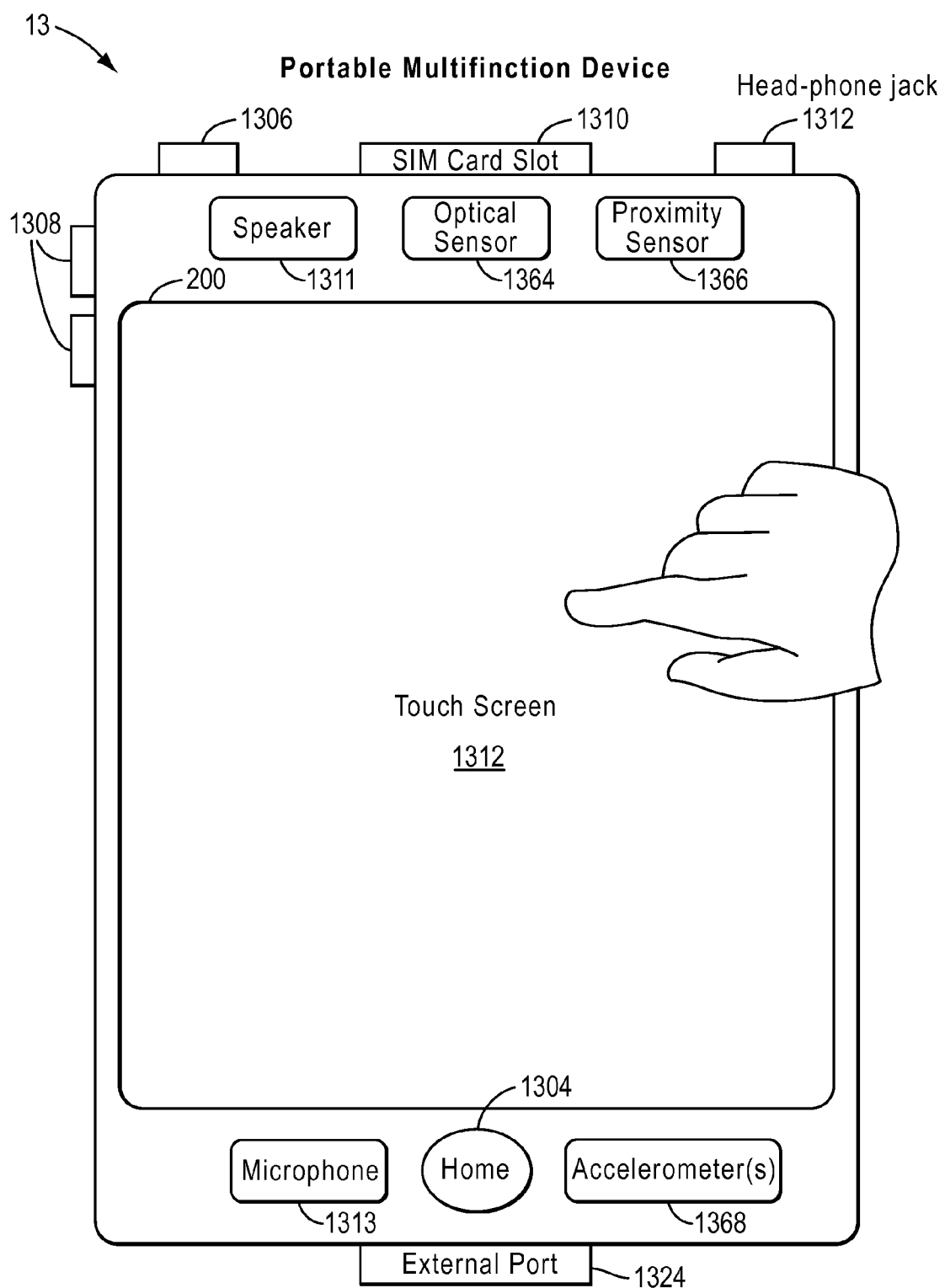

FIGS. 39-41 illustrate one embodiment of a mobile device that can be used with the present invention.

The mobile or computing device can include a display that can be a touch sensitive display. The touch-sensitive display is sometimes called a "touch screen" for convenience, and may also be known as or called a touch-sensitive display system. The mobile or computing device may include a memory (which may include one or more computer readable storage mediums), a memory controller, one or more processing units (CPU's), a peripherals interface, Network Systems circuitry, including but not limited to RF circuitry, audio circuitry, a speaker, a microphone, an input/output (I/O) subsystem, other input or control devices, and an external port. The mobile or computing device may include one or more optical sensors. These components may communicate over one or more communication buses or signal lines.

It should be appreciated that the mobile or computing device is only one example of a portable multifunction mobile or computing device, and that the mobile or computing device may have more or fewer components than shown, may combine two or more components, or a may have a different configuration or arrangement of the components. The various components may be implemented in hardware, software or a combination of hardware and software, including one or more signal processing and/or application specific integrated circuits.

Memory may include high-speed random access memory and may also include non-volatile memory, such as one or more magnetic disk storage devices, flash memory devices, or other non-volatile solid-state memory devices. Access to memory by other components of the mobile or computing device, such as the CPU and the peripherals interface, may be controlled by the memory controller.

The peripherals interface couples the input and output peripherals of the device to the CPU and memory. The one or more processors run or execute various software programs and/or sets of instructions stored in memory to perform various functions for the mobile or computing device and to process data.

In some embodiments, the peripherals interface, the CPU, and the memory controller may be implemented on a single chip, such as a chip. In some other embodiments, they may be implemented on separate chips.

The Network System circuitry receives and sends signals, including but not limited to RF, also called electromagnetic signals. The Network System circuitry converts electrical signals to/from electromagnetic signals and communicates with communications Network Systems and other communications devices via the electromagnetic signals. The Network Systems circuitry may include well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. The Network Systems circuitry may communicate with Network Systems and other devices by wireless communication.

The wireless communication may use any of a plurality of communications standards, protocols and technologies, including but not limited to Global System for Mobile Communications (GSM), Enhanced Data GSM Environment (EDGE), high-speed downlink packet access (HSDPA), wideband code division multiple access (W-CDMA), code division multiple access (CDMA), time division multiple access (TDMA), BLUETOOTH®, Wireless Fidelity (Wi-Fi) (e.g., IEEE 802.11a, IEEE 802.11b, IEEE 802.11g and/or IEEE 802.11n), voice over Internet Protocol (VoIP), Wi-MAX, a protocol for email (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), and/or Instant Messaging and Presence Service (IMPS)), and/or Short Message Service (SMS)), or any other suitable communication protocol, including communication protocols not yet developed as of the filing date of this document.

The audio circuitry, the speaker, and the microphone provide an audio interface between a user and the mobile or computing device. The audio circuitry receives audio data from the peripherals interface, converts the audio data to an electrical signal, and transmits the electrical signal to the speaker. The speaker converts the electrical signal to human-audible sound waves. The audio circuitry also receives electrical signals converted by the microphone from sound waves. The audio circuitry converts the electrical signal to audio data and transmits the audio data to the peripherals interface for processing. Audio data may be retrieved from and/or transmitted to memory and/or the Network Systems circuitry by the peripherals interface. In some embodiments, the audio circuitry also includes a headset jack. The headset jack provides an interface between the audio circuitry and removable audio input/output peripherals, such as output-only headphones or a headset with both output (e.g., a headphone for one or both ears) and input (e.g., a microphone).

The I/O subsystem couples input/output peripherals on the mobile or computing device, such as the touch screen and other input/control devices, to the peripherals interface. The I/O subsystem may include a display controller and one or more input controllers for other input or control devices. The one or more input controllers receive/send electrical signals from/to other input or control devices. The other input/control devices may include physical buttons (e.g., push buttons, rocker buttons, etc.), dials, slider switches, and joysticks, click wheels, and so forth. In some alternate embodiments, input controller(s) may be coupled to any (or none) of the following: a keyboard, infrared port, USB port, and a pointer device such as a mouse. The one or more buttons may include an up/down button for volume control of the speaker and/or the microphone. The one or more buttons may include a push button. A quick press of the push button may disengage a lock of the touch screen or begin a process that uses gestures on the touch screen to unlock the device, as described in U.S. patent application Ser. No. 11/322,549, "Unlocking a Device by Performing Gestures on an Unlock Image," filed Dec. 23, 2005, which is hereby incorporated by reference in its entirety. A longer press of the push button may turn power to the mobile or computing device on or off. The user may be able to customize a functionality of one or more of the buttons. The touch screen is used to implement virtual or soft buttons and one or more soft keyboards.

The touch-sensitive touch screen provides an input interface and an output interface between the device and a user. The display controller receives and/or sends electrical signals from/to the touch screen. The touch screen displays visual output to the user. The visual output may include graphics, text, icons, video, and any combination thereof (collectively termed "graphics"). In some embodiments, some or all of the visual output may correspond to user-interface objects, further details of which are described below.

A touch screen has a touch-sensitive surface, sensor or set of sensors that accepts input from the user based on haptic and/or tactile contact. The touch screen and the display controller (along with any associated modules and/or sets of instructions in memory) detect contact (and any movement or breaking of the contact) on the touch screen and converts the detected contact into interaction with user-interface objects (e.g., one or more soft keys, icons, web pages or images) that are displayed on the touch screen. In an exemplary embodiment, a point of contact between a touch screen and the user corresponds to a finger of the user.

The touch screen may use LCD (liquid crystal display) technology, or LPD (light emitting polymer display) technology, although other display technologies may be used in other embodiments. The touch screen and the display controller may detect contact and any movement or breaking thereof using any of a plurality of touch sensing technologies now known or later developed, including but not limited to capacitive, resistive, infrared, and surface acoustic wave technologies, as well as other proximity sensor arrays or other elements for determining one or more points of contact with a touch screen.

A touch-sensitive display in some embodiments of the touch screen may be analogous to the multi-touch sensitive tablets described in the following U.S. Pat. No. 6,323,846 (Westerman et al.), U.S. Pat. No. 6,570,557 (Westerman et al.), and/or U.S. Pat. No. 6,677,932 (Westerman), and/or U.S. Patent Publication 2002/0015024A1, each of which is hereby incorporated by reference in their entirety. However, a touch screen displays visual output from the portable mobile or computing device, whereas touch sensitive tablets do not provide visual output.

A touch-sensitive display in some embodiments of the touch screen may be as described in the following applications: (1) U.S. patent application Ser. No. 11/381,313, "Multipoint Touch Surface Controller," filed May 12, 2006; (2) U.S. patent application Ser. No. 10/840,862, "Multipoint Touchscreen," filed May 6, 2004; (3) U.S. patent application Ser. No. 10/903,964, "Gestures For Touch Sensitive Input Devices," filed Jul. 30, 2004; (4) U.S. patent application Ser. No. 11/048,264, "Gestures For Touch Sensitive Input Devices," filed Jan. 31, 2005; (5) U.S. patent application Ser. No. 11/038,590, "Mode-Based Graphical User Interfaces For Touch Sensitive Input Devices," filed Jan. 18, 2005; (6) U.S. patent application Ser. No. 11/228,758, "Virtual Input Device Placement On A Touch Screen User Interface," filed Sep. 16, 2005; (7) U.S. patent application Ser. No. 11/228,700, "Operation Of A Computer With A Touch Screen Interface," filed Sep. 16, 2005; (8) U.S. patent application Ser. No. 11/228,737, "Activating Virtual Keys Of A Touch-Screen Virtual Keyboard," filed Sep. 16, 2005; and (9) U.S. patent application Ser. No. 11/367,749, "Multi-Functional Hand-Held Device," filed Mar. 3, 2006. All of these applications are incorporated by reference herein in their entirety.

The touch screen may have a resolution in excess of 1000 dpi. In an exemplary embodiment, the touch screen has a resolution of approximately 1060 dpi. The user may make contact with the touch screen using any suitable object or appendage, such as a stylus, a finger, and so forth. In some embodiments, the user interface is designed to work primarily with finger-based contacts and facial expressions, which are much less precise than stylus-based input due to the larger area of contact of a finger on the touch screen. In some embodiments, the device translates the rough finger-based input into a precise pointer/cursor position or command for performing the actions desired by the user.

In some embodiments, in addition to the touch screen, the mobile or computing device may include a touchpad (not shown) for activating or deactivating particular functions. In some embodiments, the touchpad is a touch-sensitive area of the device that, unlike the touch screen, does not display visual output. The touchpad may be a touch-sensitive surface that is separate from the touch screen or an extension of the touch-sensitive surface formed by the touch screen.

In some embodiments, the mobile or computing device may include a physical or virtual click wheel as an input control device. A user may navigate among and interact with one or more graphical objects (henceforth referred to as icons) displayed in the touch screen by rotating the click wheel or by moving a point of contact with the click wheel (e.g., where the amount of movement of the point of contact is measured by its angular displacement with respect to a center point of the click wheel). The click wheel may also be used to select one or more of the displayed icons. For example, the user may press down on at least a portion of the click wheel or an associated button. User commands and navigation commands provided by the user via the click wheel may be processed by an input controller as well as one or more of the modules and/or sets of instructions in memory. For a virtual click wheel, the click wheel and click wheel controller may be part of the touch screen and the display controller, respectively. For a virtual click wheel, the click wheel may be either an opaque or semitransparent object that appears and disappears on the touch screen display in response to user interaction with the device. In some embodiments, a virtual click wheel is displayed on the touch screen of a portable multifunction device and operated by user contact with the touch screen.

The mobile or computing device also includes a power system for powering the various components. The power system may include a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

The mobile or computing device may also include one or more sensors, including not limited to optical sensors. In one embodiment an optical sensor is coupled to an optical sensor controller in I/O subsystem. The optical sensor may include charge-coupled device (CCD) or complementary metal-oxide semiconductor (CMOS) phototransistors. The optical sensor receives light from the environment, projected through one or more lens, and converts the light to data representing an image. In conjunction with an imaging module (also called a camera module); the optical sensor may capture still images or video. In some embodiments, an optical sensor is located on the back of the mobile or computing device, opposite the touch screen display on the front of the device, so that the touch screen display may be used as a viewfinder for either still and/or video image acquisition. In some embodiments, an optical sensor is located on the front of the device so that the user's image may be obtained for videoconferencing while the user views the other video conference participants on the touch screen display. In some embodiments, the position of the optical sensor can be changed by the user (e.g., by rotating the lens and the sensor in the device housing) so that a single optical sensor may be used along with the touch screen display for both video conferencing and still and/or video image acquisition.

The mobile or computing device may also include one or more proximity sensors. In one embodiment, the proximity sensor is coupled to the peripherals interface. Alternately, the proximity sensor may be coupled to an input controller in the I/O subsystem. The proximity sensor may perform as described in U.S. patent application Ser. No. 11/241,839, "Proximity Detector In Handheld Device," filed Sep. 30, 2005; Ser. No. 11/240,788, "Proximity Detector In Handheld Device," filed Sep. 30, 2005; Ser. No. 13/096,386, "Using Ambient Light Sensor To Augment Proximity Sensor Output"; Ser. No. 13/096,386, "Automated Response To And Sensing Of User Activity In Portable Devices," filed Oct. 24, 2006; and Ser. No. 11/638,251, "Methods And Systems For Automatic Configuration Of Peripherals," which are hereby incorporated by reference in their entirety. In some embodiments, the proximity sensor turns off and disables the touch screen when the multifunction device is placed near the user's ear (e.g., when the user is making a phone call). In some embodiments, the proximity sensor keeps the screen off when the device is in the user's pocket, purse, or other dark area to prevent unnecessary battery drainage when the device is a locked state.

In some embodiments, the software components stored in memory may include an operating system, a communication module (or set of instructions), a contact/motion module (or set of instructions), a graphics module (or set of instructions), a text input module (or set of instructions), a Global Positioning System (GPS) module (or set of instructions), and applications (or set of instructions).

The operating system (e.g., Darwin, RTXC, LINUX, UNIX, OS X, WINDOWS, or an embedded operating system such as VxWorks) includes various software components and/or drivers for controlling and managing general system tasks (e.g., memory management, storage device control, power management, etc.) and facilitates communication between various hardware and software components.

The communication module facilitates communication with other devices over one or more external ports and also includes various software components for handling data received by the Network Systems circuitry and/or the external port. The external port (e.g., Universal Serial Bus (USB), FIREWIRE, etc.) is adapted for coupling directly to other devices or indirectly over Network System. In some embodiments, the external port is a multi-pin (e.g., 30-pin) connector that is the same as, or similar to and/or compatible with the 30-pin connector used on iPod (trademark of Apple Computer, Inc.) devices.

The contact/motion module may detect contact with the touch screen (in conjunction with the display controller) and other touch sensitive devices (e.g., a touchpad or physical click wheel). The contact/motion module includes various software components for performing various operations related to detection of contact, such as determining if contact has occurred, determining if there is movement of the contact and tracking the movement across the touch screen, and determining if the contact has been broken (i.e., if the contact has ceased). Determining movement of the point of contact may include determining speed (magnitude), velocity (magnitude and direction), and/or an acceleration (a change in magnitude and/or direction) of the point of contact. These operations may be applied to single contacts (e.g., one finger contacts) or to multiple simultaneous contacts (e.g., "multitouch"/multiple finger contacts). In some embodiments, the contact/motion module and the display controller also detect contact on a touchpad. In some embodiments, the contact/motion module and the controller detects contact on a click wheel.

Examples of other applications that may be stored in memory include other word processing applications, JAVA-enabled applications, encryption, digital rights management, voice recognition, and voice replication.

In conjunction with touch screen, display controller, contact module, graphics module, and text input module, a contacts module may be used to manage an address book or contact list, including: adding name(s) to the address book; deleting name(s) from the address book; associating telephone number(s), e-mail address(es), physical address(es) or other information with a name; associating an image with a name; categorizing and sorting names; providing telephone numbers or e-mail addresses to initiate and/or facilitate communications by telephone, video conference, e-mail, or IM; and so forth.

The foregoing description of various embodiments of the claimed subject matter has been provided for the purposes of illustration and description. It is not intended to be exhaustive or to limit the claimed subject matter to the precise forms disclosed. Many modifications and variations will be apparent to the practitioner skilled in the art. Particularly, while the concept "component" is used in the embodiments of the systems and methods described above, it will be evident that such concept can be interchangeably used with equivalent concepts such as, class, method, type, interface, module, object model, and other suitable concepts. Embodiments were chosen and described in order to best describe the principles of the invention and its practical application, thereby enabling others skilled in the relevant art to understand the claimed subject matter, the various embodiments and with various modifications that are suited to the particular use contemplated.

What is claimed is:

1. A method for monitoring a person's sleep parameters, sleep activities, sleep state, or awake status sleep, comprising:

providing a monitoring device that includes a microphone, a transmitter and sensors to determine air quality, sound level/quality, light quality and ambient temperature near the person;

an accelerometer or other motion detection apparatus configured to record movement information of the person;

using the accelerometer, or other motion detection apparatus, and the monitoring device configured to assist in determining sleep information and sleep behavior information of the person, the microphone configured to record movement sounds of the person;

providing that the recording of the microphone is disabled to stop recording person movement sounds that are detected by the accelerometer or other motion detection apparatus when the movement sounds are not directed to asleep related parameter;

in response to information from the monitoring device and the accelerometer or other motion detection apparatus detecting at least one of a person's motion, movement and gesture for determining a person's sleep parameters, sleep activities, sleep state, or awake status; and communicating the at least one of a person's motion, movement and gesture to the monitoring device that includes at least two elements selected from: a proximity sensor; a temperature sensor/humidity sensor; a particulate sensor; a light sensor; a microphone; a speaker; two RF transmitters (BLE/ANT+WIFI); a memory card; and LED's.

2. The method of claim 1, wherein the person's sleep parameters, sleep activities, sleep state, or awake status sleep are selected from at least one of: sleep-related breathing disorders, sleep apnea, sleep-related seizure disorders, sleep-related movement disorders including periodic limb movement disorder, restless legs syndrome (RLS), problems sleeping at night (insomnia), sleep disorders that cause extreme daytime tiredness including narcolepsy, problems with nighttime behaviors including sleepwalking, night terrors, or bed-wetting, bruxism or grinding of the teeth during sleep, problems sleeping during the day because of working at night or rotating shift work and determine stages of sleep.

3. The method of claim 1, further comprising:
utilizing a plurality of ports selected from at least one of a port that: (i) allows light to be transmitted from an interior of the monitor device to the person for visual feedback, (ii) a port for a proximity sensor and (iii) one or more ports that allows for the introduction of air.

4. The method of claim 1, further comprising:
detecting particulates with a particulate sensor.

5. The method of claim 1, further comprising:
providing feedback to a person.

6. The method of claim 1, further comprising:
detecting at least one of motion, movement and gestures of a person over a certain threshold.

7. The method of claim 1, further comprising:
waking up a CPU in response to detection of motion, movement or a gesture.

8. The method of claim 1, further comprising:
processing data in response to the at least one of motion, movement and gesture detection.

9. The method of claim 1, further comprising:
transmitting data collected through an RF transmitter.

10. The method of claim 1, wherein the at least one of motion, movement and gesture detection is achieved with an accelerometer detection device.

11. The method of claim 1, further comprising:
determining X, Y, and X axis information in response to the at least one of motion, movement and gesture.

12. The method of claim 1, further comprising:
communicating with the monitor device over an ANT protocol.

* * * * *